(12) United States Patent
Beaumont et al.

(10) Patent No.: US 9,732,151 B2
(45) Date of Patent: Aug. 15, 2017

(54) BIOMARKERS FOR TSLP TREATMENT

(71) Applicant: Merck Sharp & Dohme Corp., Rahway, NJ (US)

(72) Inventors: Maribel Beaumont, San Mateo, CA (US); Jeanine D. Mattson, San Francisco, CA (US); Jennifer R. Louten, Marietta, GA (US); Terrill K. McClanahan, Sunnyvale, CA (US); Rene de Waal Malefyt, Sunnyvale, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 21 days.

(21) Appl. No.: 14/356,029

(22) PCT Filed: Oct. 31, 2012

(86) PCT No.: PCT/US2012/062856
§ 371 (c)(1),
(2) Date: May 2, 2014

(87) PCT Pub. No.: WO2013/067051
PCT Pub. Date: May 10, 2013

(65) Prior Publication Data
US 2014/0302061 A1 Oct. 9, 2014

Related U.S. Application Data

(60) Provisional application No. 61/555,129, filed on Nov. 3, 2011.

(51) Int. Cl.
*C07K 16/24* (2006.01)
*G01N 33/543* (2006.01)
*G01N 33/68* (2006.01)
*C12Q 1/68* (2006.01)

(52) U.S. Cl.
CPC ............ *C07K 16/24* (2013.01); *C12Q 1/6883* (2013.01); *G01N 33/54306* (2013.01); *G01N 33/6863* (2013.01); *C12Q 2600/106* (2013.01); *C12Q 2600/158* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | |
|---|---|---|
| 2004/0166521 A1 | 8/2004 | Boyd |
| 2009/0068685 A1* | 3/2009 | Streeper ........... G01N 33/57423 435/7.23 |
| 2009/0186022 A1 | 7/2009 | Bardroff |
| 2009/0221444 A1* | 9/2009 | Borlak et al. .................. 506/16 |
| 2009/0238823 A1* | 9/2009 | Comeau ............... C07K 16/244 424/133.1 |
| 2009/0325176 A1* | 12/2009 | O'Toole ............... C12Q 1/6883 435/6.16 |
| 2010/0098659 A1 | 4/2010 | Watson |
| 2010/0098687 A1 | 4/2010 | Watson |
| 2010/0136003 A1 | 6/2010 | De Waal Malefyt |
| 2011/0123530 A1* | 5/2011 | Arron et al. ............... 424/134.1 |

FOREIGN PATENT DOCUMENTS

WO 2009124090 A1 10/2009

OTHER PUBLICATIONS

Waiker et al (J Am Soc Nephrol. Jan. 2012; 23(1): 13-21).*
Ardern-Jones et al (British Journal of Dermatology (2014) 171, pp. 207-208).*
Wadworth et al (Journal of Asthma and Allergy 2011:4 77-86).*
Cole et al., The Role of Defensins in Lung Biology and Therapy, Am. J. Respir. Med., 2002, 249-259, 1-4.
Long et al., Gob-5 Contributes to Goblet Cell Hyperplasia and Modulates Pulmonary Tissue Inflammation, Am. J. Respir. Cell Mol. Biol., 2006, vol. 35, 357-365.
Mishra et al., Resistin-like molecule-beta is an allergen-induced cytokine with inflammatory and remodeling activity in the murine lung, Am. J. Physiol Lung Cell Mol. Physiol., Jun. 1, 2007, vol. 293, L305-L313.
Renigunta et al., Human RELMbeta is a mitogenic factor in lung cells and induced in hypoxia, FEBS Letters, 2006, vol. 580, 900-903.
Phalipon et al., Novel functions of the polymeric Ig receptor: well beyond transport of immunoglobulins, Trends in Immunology, Feb. 2003, vol. 24, No. 2, 55-58.
Zhou et al., Thymic stromal lymphopoietin as a key initiator of allergic airway inflammation in mice, Nature Immunology, Oct. 2005, vol. 6, No. 10, 1047-1053.
Blanchard et al., Biology of the Eosinophil, Advance in Immunology, 2009, vol. 101, 81-121.
Liu et al., Mammalian Peptidoglycan Recognition Protein Binds Peptidoglycan with High Affinity, is Expressed in Neutrophils, and Inhibits Bacterial Growth, The Journal of Biological Chemistry, Aug. 11, 2000, vol. 275, No. 32, 24490-24499.
Lee et al., Role of breast regression protein 39 (BRP-39)/Chitinase 3-like-1 in TH2 and IL-13-induced tissue responses and apoptosis, The Journal of Experimental Medicine, May 4, 2009, vol. 206, No. 5, 1149-1166.
Hartl et al., Acidic Mammalian Chitinase is Secreted via an ADAM17/Epidermal Growth Factor Receptor-dependent Pathway and Stimulates Chemokine Production by Pulmonary Epithelial Cells, The Journal of Biological Chemistry, vol. 283, No. 48, 33472-33482, Nov. 28, 2008.

(Continued)

*Primary Examiner* — Brian J Gangle
*Assistant Examiner* — Andrea McCollum
(74) *Attorney, Agent, or Firm* — Gloria M. Fuentes; Li Su

(57) ABSTRACT

The present invention relates to biomarker responsive to treatment with an anti-Thymic Stromal Lymphopoietin (TSLP) antibody.

9 Claims, 35 Drawing Sheets

(56) References Cited

OTHER PUBLICATIONS

Di Valentin et al., New asthma biomarkers: lessons from murine models of acute and chronic asthma, Am. J. Physiol.Lung Cel Mol. Physiol., 2009, vol. 296 L185-L197.

Chupp et al., A Chitinase-like Protein in the Lung and Circulation of Patients with Severe Asthma, The New England Journal of Medicine, 2007, vol. 357, 2016-2017.

Jeong et al., Proteomic Analysis of Differently Expressed Proteins in a Mouse Model for Allergic Asthma, J. Korean Med. Sci., 2005, vol. 20, 579-585.

Fajardo et al., Increased Levels of Hypoxia-sensitive Proteins in Allergic Airway Inflammation, Am. J. Respir. Crit. Care Med., 2004, vol. 170, 477-484.

Lauredo et al., Leukocytic cell sources of airway tissue kallikrein, Am. J. Physiol. Lung Cell Mol. Physiol, Dec. 5, 2003, vol. 286, L734-L740.

Elias, M.D., Chitinases and chitinase-like proteins in TH2 inflammation and asthma, J. Allergy Clin. Immunol., 2005, vol. 116, 497-500.

Zhao et al., Dexamethasone Alters Bronchoalveolar Lavage Fluid Proteome in a Mouse Asthma Model, International Archives of Allergy and Immunology, 2007, vol. 142, 219-229.

Zhao et al., Increased lungkine and chitinase levels in allergic airway inflammation: A proteomics approach, Proteomics, 2005, vol. 5., 2799-2807.

Clements et al., The Tissue Kallikrein Family of Serine Proteases: Functional Roles in Human Diseases and Potential as Clinical Biomarkers, Critical Reviews in Clinical Laboratory Sciences, 2004, vol. 41, No. 3, 265-312.

Greenlee et al., Matrix Metalloproteinases in Lung: Multiple, Multifarious, and Multifaceted, Physiol. Rev., 2007, vol. 87, 69-98.

Zhang et al., Oxidative Stress and Asthma: Proteome Analysis of Chitinase-like Proteins and FIZZ1 in Lung Tissue and Bronchoalveolar Lavage Fluid, Journal of Proteome Research, 2009, vol. 8., 1631-1638.

Shuhui et al., Role of Mammalian Chitinases in Asthma, International Archives of Allergy and Immunology, Mar. 17, 2009, vol. 149, 369-377.

Rothernberg et al., The Eosinophil, Annu. Rev. Immunol., 2006, vol. 24, 147-174.

Harada et al., Human IgGFc Binding Protein (FcyBP) in Colonic Epithelial Cells Exhibits Mucin-like Structure, The Journal of Biological Chemistry, Jun. 13, 1997, vol. 272, No. 24, 15332-15241.

Novershtern et al., A Functional and Regulatory Map of Asthma, Am. J. Respir. Cell Mol. Biol., 2008, vol. 38, 324-336.

Salvi et al., Could the airway epithelium play an important role in mucosal imunoglobulin A production?, Clinical and Experimental Allergy, 1999, vol. 29, 1597-1605.

Lanone et al., Overlapping and enzyme-specific contribution of matrix metalloproteinases-9 and-12 in IL-13-induced inflammation and remodeling, Journal of Clinical Investigation, Aug. 2002, vol. 110, 463-474.

Wong, et al., Proteome Analysis of Chronically Inflamed Lungs in a Mouse Chronic Asthma Model, International Archives of Allergy and Immunology, 2008, vol. 147,179-189.

Kim et al., Histamine Induces MUC5AC Expression via a hCLCA1 Pathway, Pharmacology, 2007, vol. 80, 219-226.

Liu et al., TSLP: An Epithelial Cell Cytokine that Regulates T Cell Differentiation by Conditioning Dendritic Cell Maturation, Ann. Rev. Immunol., 2007, vol. 25, 193-219.

Chan et al., Lipocalin 2 is Required for Pulmonary Host Defense against Klebsiella Infection, The Journal of Immunology, 2009, vol. 182, 4947-4956.

Zafra M. et al., Profiling of genes expressed in lungs of chronic asthmatic mice treated with galectin-3: down-regulation of inflammatory and regulatory genes, Allergy, Jun. 1, 2011, vol. 66, No. Suppl. 94, Spec. Issue, 445-446.

Woodruff et al., Genome-wide profiling identities elpithelial cell genes associated with asthma and with treatment response to corticosteroids, Proceedings of the National Academy of Sciences, National Academy of Sciences, Oct. 1, 2007 vol. 104, No. 40, 15858-15863.

Edwards et al., Therapy directed against thymic stromal lymphopoietin (TSLP), Progress in Respiratory Research, Jan. 1, 2010, vol. 39, 55-59.

Shikotra et al., Increased expression of immunoreactive thymic stromal lymphopoietin in patients with severe asthma, Journal of Allergy and Clinical Immunology, Aug. 29, 2011, vol. 129, No. 1, 104-111.

Yu et al., Effect of a matrix metalloproteinase-12 inhibitor, S-1, on allergic airway disease phenotypes in mice, Inflammation Research; Official Journal of: the International Association of Inflammation Societies the European Histamine Research Society, Jan. 12, 2010, vol. 59, No. 6, 419-428.

Cheng et al., Thymic stromal lymphopoietin receptor blockade reduces allergic inflammation in a cynomolgus monkey model of asthma, Journal of Allergy and Clinical Immunology, Aug. 1, 2013, vol. 132, No. 2, 455-462.

Louten et al., Biomarkers of Disease and Treatment in Murine and Cynomolgus Models of Chronic Asthma, Biomarker Insights, Jul. 1, 2012, 87.

Nguyen et al., TSLP directly impairs pulmonary Treg function; association with aberrant tolerogenic immunity in asthmatic airway. Allergy Asthma Clin. Immunol., 2010, vol. 6(1):4.

Boehme et al., A small molecule CRTH2 antagonist inhibits FITC-induced allergic cutaneous inflammation, Int. Immunol. , 2009, vol. 21(1), p. 81-83.

\* cited by examiner

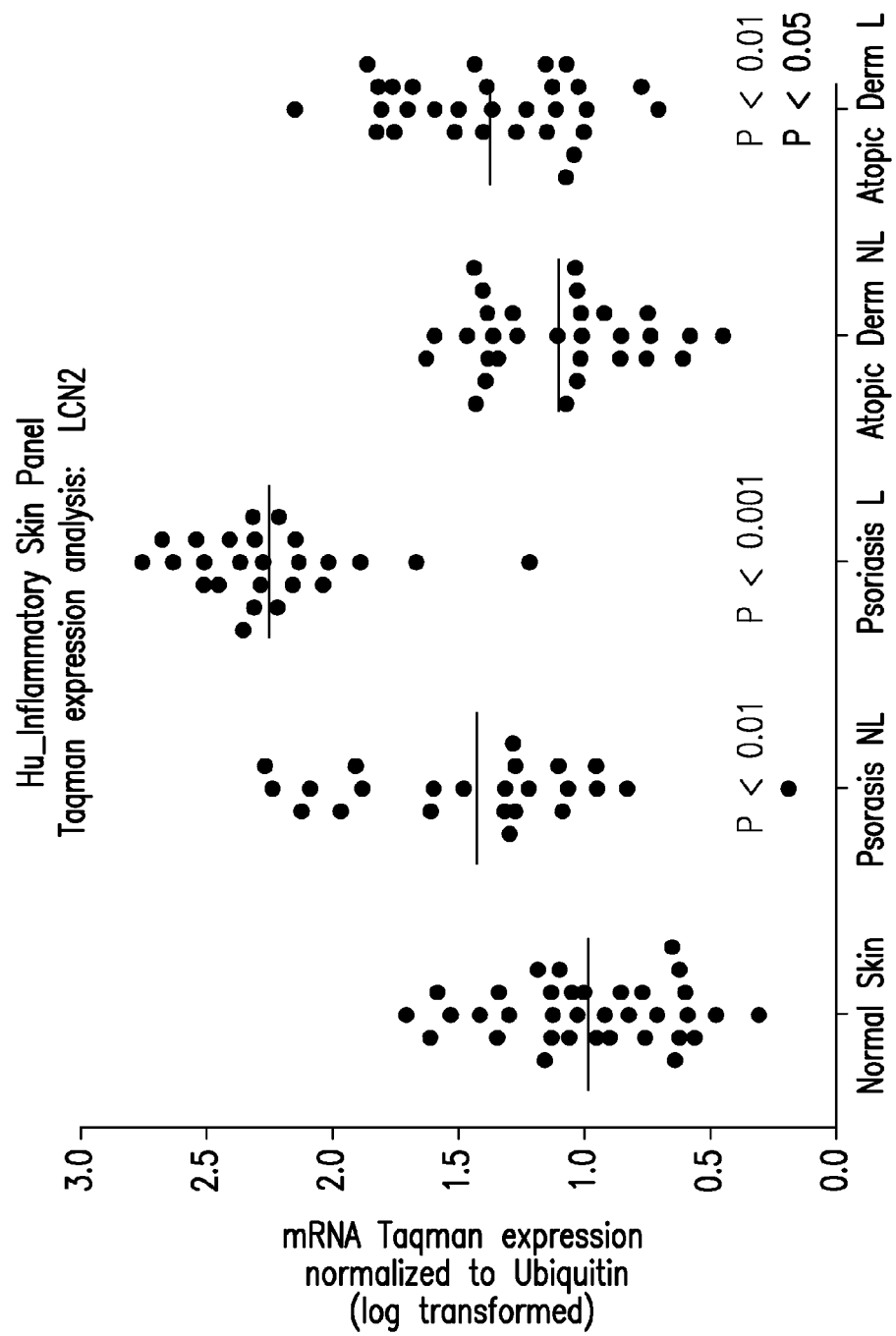

BIOMARKERS FOR TSLP TREATMENT

FIELD OF THE INVENTION

The present invention relates to biomarkers of treatment with a TSLP antagonist.

BACKGROUND OF THE INVENTION

TSLP is an immune cytokine that induces dendritic cell-mediated CD4$^+$ T cell responses with a proallogenic phenotype. Dendritic cells activated by TSLP play crucial role in the induction and maintenance of allergic inflammatory Th2 by production of proallergenic cytokines, chemokines and costimulatory molecules that direct naïve T cells to become Th2 cells, producing IL-4, IL-5 and IL-13. Overexpression of TSLP in Atopic Dermatitis (AtD), Netherton Syndrome and asthma indicates a crucial role of this cytokine in the pathogenesis of these allergic inflammatory diseases. The use of TSLP antagonists for the treatment of allergic disease is under clinical investigation. The need exists for methods for monitoring the efficacy of treatment with TSLP antagonists. Such methods would preferably allow objective determination of a subject's disease state and/or response to treatment with a TSLP antagonist.

A "biomarker" is an objectively measured indicator that reflects the presence, progression, or successful treatment of a particular condition. Biomarkers have long been used in drug development, and the discovery and validation of new efficacy biomarkers is expected to improve the predictive disease models, reduce the time and cost associated with drug development, and increase the success rate of translating experimental drugs into clinical therapeutics. In addition, biomarkers are valuable in early detection of disease development, changes in disease status, and effectiveness of behavioral modifications and therapeutics in disease control.

The collection of proteins expressed during a disease (i.e., the disease proteome) is particularly useful for detection of disease, monitoring disease status, and evaluating effectiveness of therapeutics. Analysis of plasma for biomarkers is common due to the ease of accessibility, but biological fluids or tissues from the local site of pathology, known as "proximal fluids," are often represent a more accurate state of the condition. Accordingly, there is a need for methods of monitoring the efficacy of treatment with a TSLP antagonist using a biomarker that is preferably detectable in proximal fluids.

SUMMARY OF THE INVENTION

The present invention meets these needs in the art by providing various biomarkers whose level reflects response to treatment with a TSLP antagonist, and by providing various biomarkers whose level reflects allergic disease state. These biomarkers can be used in improved methods of treatments using TSLP antagonists.

In one embodiment, the invention relates to a method for detecting the expression of a biomarker in a sample from a subject treated with a TSLP antagonist, comprising: measuring expression of one or more biomarkers in a sample from the subject; wherein at least one biomarker is selected from the group consisting of: MMP12, LCN2, PGLYRP1, CHI3L1/YKL-40, CHI3L1/YKL-40, REG3G, CD44, RNASE3, RNASE2, RNASE7, CHIA, and CHIAP2; wherein decreased expression of the biomarker compared to a control is indicative of the presence of a beneficial response in the subject; or wherein unchanged or increase expression of the biomarker compared to a control is indicative of the absence of a beneficial response in the subject. In one embodiment, the biomarker is MMP-12. In one embodiment, the biomarker is LCN2. In one embodiment, the biomarker is YKL-40. In one embodiment, the subject is a human subject suffering from an allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

The invention also comprises a method for monitoring TSLP blockade in a mammalian subject treated with a TSLP antagonist comprising: measuring expression of one or more biomarkers in a sample from the subject; wherein at least one biomarker is selected from the group consisting of: MMP12, LCN2, PGLYRP1, CHI3L1/YKL-40, CHI3L1/YKL-40, REG3G, CD44, RNASE3, RNASE2, RNASE7, CHIA, and CHIAP2; wherein decreased expression the biomarker compared to a control is indicative of TSLP blockade in the subject and suitability of the subject for treatment with a TSLP antagonist; or wherein unchanged or higher expression of the biomarker compared to a control is indicative of a lack of TSLP blockade in response to a TSLP antagonist in the subject and a lack of suitability of the subject for treatment with a TSLP antagonist. In one embodiment, the biomarker is MMP-12. In one embodiment, the subject is a human subject suffering from an allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

The invention also comprises a method treating a mammalian subject with a TSLP antagonist comprising: obtaining a baseline biological sample from the subject prior to administering a dose of a TSLP antagonist; measuring the level of one or more biomarkers in the baseline biological sample by gene expression analysis or immunoassay, wherein at least one biomarker is selected from the group consisting of: MMP12, LCN2, PGLYRP1, CHI3L1/YKL-40, REG3G, CD44, RNASE3, RNASE2, RNASE7, CHIA, and CHIAP2; administering the TSLP antagonist to the subject; obtaining from the subject at least one subsequent biological sample; measuring the level of the biomarker in the subsequent sample by gene expression analysis or immunoassay; comparing the level of the biomarker in the subsequent biological sample with the level of the biomarker in the baseline biological sample, and determining whether treatment with the TSLP antagonist should be continued, discontinued or modified. In one embodiment, the biomarker is MMP-12. In one embodiment, the biomarker is LCN2. In one embodiment, the biomarker is YKL-40. In one embodiment, the biomarker is LCN2. In one embodiment, the biomarker is YKL-40. In one embodiment, the subject suffers from allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

The invention also comprises a method of treating an a mammalian subject in need thereof, the method comprising the steps of: administering an effective amount of a TSLP antagonist to the subject; measuring expression of one or more biomarkers in a sample from the subject, wherein at least one biomarker is selected from the group consisting of: MMP12, LCN2, PGLYRP1, CHI3L1/YKL-40, REG3G, CD44, RNASE3, RNASE2, RNASE7, CHIA, and CHIAP2; and determining whether treatment with the TSLP antagonist should be continued, discontinued or modified. In one embodiment, the subject suffers from allergic disease. In one embodiment, the biomarker is MMP-12. In one embodiment, the biomarker is LCN2. In one embodiment, the biomarker is YKL-40. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

The invention also comprises a method of treating a mammalian subject in need thereof, the method comprising the steps of: administering an effective amount of a TSLP antagonist to the subject; wherein the subject prior to the administration of the TSLP antagonist has been tested for the expression of a biomarker selected from the group consisting of: MMP12, LCN2, PGLYRP1, CHI3L1/YKL-40, REG3G, CD44, RNASE3, RNASE2, RNASE7, CHIA, and CHIAP2; and wherein the expression level of the biomarker relative to a control guides the decision to continue, discontinue or modify treatment. In one embodiment, the biomarker is MMP-12. In one embodiment, the biomarker is LCN2. In one embodiment, the biomarker is YKL-40. In one embodiment, the subject suffers from allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

In one embodiment, the invention comprises a method of treating a mammalian subject in need thereof with a TSLP antagonist comprising: measuring expression of one or more biomarkers in a sample from said subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2 and, if biomarker levels in the sample are higher than a control, administering a therapeutically effective amount of a TSLP antagonist to the subject. In one embodiment, the biomarker is MMP-12. In one embodiment, the biomarker is LCN2. In one embodiment, the biomarker is YKL-40. In one embodiment, the subject suffers from allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

A method for treating a subject in need thereof with a TSLP antagonist comprising: obtaining a first biological sample from the subject prior to administering a dose of a TSLP antagonist; measuring the expression of one or more biomarkers in the baseline biological sample, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2; administering the TSLP antagonist to the subject; obtaining from the subject a second biological sample; measuring the expression of the biomarker in the second sample; comparing the expression of the biomarker in the second biological sample with the expression of the biomarker in the first biological sample, and, if the biomarker levels are reduced in the second biological sample as compared to the first biological sample, administering a therapeutically effective amount of a TSLP antagonist to the subject. In one embodiment, the subject suffers from allergic disease. In one embodiment, the biomarker is MMP-12. In one embodiment, the biomarker is LCN2. In one embodiment, the biomarker is YKL-40. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

A method for selecting a subject from treatment with a TSLP antagonist comprising measuring expression of one or more biomarkers in a sample from said subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2, and, if the biomarker levels in the sample are higher than the levels of a control, then administering a therapeutically effective amount of a TSLP antagonist to the subject. In one embodiment, the subject suffers from allergic disease. In one embodiment, the biomarker is MMP-12. In one embodiment, the biomarker is LCN2. In one embodiment, the biomarker is YKL-40. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

A method for monitoring progress of treatment of a subject with a TSLP antagonist comprising: a) measuring expression of one or more biomarker in a sample from said subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2 and, if the biomarker levels in the sample are higher than the levels of a control, then administering a therapeutically effective amount of a TSLP antagonist to the subject. In one embodiment, the biomarker is MMP-12. In one embodiment, the biomarker is LCN2. In one embodiment, the biomarker is YKL-40. In one embodiment, the subject suffers from allergic disease. In one embodiment, the allergic disease is asthma. In another embodiment, the allergic disease is atopic dermatitis. In one embodiment, the method further comprises measuring the expression of the one or more biomarkers selected from the group consisting of: MDC/CCL22, CCL17/TARC, CD40, CD80 and IL-19.

In some embodiments, any of the above described methods could comprise measuring two, three, four, five or six biomarkers. In some embodiments, any of the above described methods comprise measuring two or more biomarkers selected from the group consisting of: MMP12, LCN2, PGLYRP1, CHI3L 1/YKL-40, REG3G, CD44, RNASE3, RNASE2, RNASE7, CHIA, and CHIAP2.

In some embodiments, the TSLP antagonist is an anti-TSLP antibody or an anti-TSLPR antibody. In other embodiments, the TSLP antagonist is a soluble TSLPR. In other embodiments, the TSLP antagonist is a TSLPR-Ig fusion protein.

In some embodiments, the sample is tissue sample. In other embodiments, the sample is a lung biopsy. In other embodiments, the sample is a blood sample. In other embodiments, the sample is serum. In other embodiments, the sample is plasma. In one embodiment, the sample is sputum fluid or sputum cells. In another embodiment, the sample is BAL fluid or BAL cells. In another embodiment, the sample is skin.

In some embodiments, the expression of the biomarker is determined by gene expression analysis or immunoassay. In other embodiments, the expression of the biomarker is determined by an immunoassay selected from the group consisting of ELISA, RIA, Western blot, luminescent immunoassay, fluorescent immunoassay. In other embodiments, the expression of the biomarker is determined by gene expression analysis, wherein said gene expression analysis is selected from the group consisting of is selected from the group consisting of Northern blotting, PCR-based, SAGE, flow cytometry-based, and DNA microarray.

In some embodiments, the control is a sample from the subject prior to treatment with a TSLP antagonist. In other embodiments, the control is one or more samples from samples from subjects that do not suffer from allergic disease. In other embodiments, the control is one or more samples from samples from subjects that do not suffer from allergic disease and are not treated with a TSLP antagonist.

The invention also comprises an ELISA kit comprising antibodies (or antigen binding fragments thereof) that specifically bind to two or more biomarkers selected from the group consisting of: MMP12, LCN2, PGLYRP1, CHI3L1/YKL-40, REG3G, CD44, RNASE3, RNASE2, RNASE7, CHIA, and CHIAP2. In one embodiment, the ELISA kit further comprises antibodies (or antigen binding fragments thereof) that specifically bind one or more biomarkers selected from the group consisting of: MDC/CCL22, CCL17/TARC, CD40, CD80 and IL-19. In one embodiment, the ELISA kit further comprises instructions for the use of the kit in monitoring TSLP blockage. In another embodiment, the kit further comprises instructions for using the kit in monitoring asthma progression.

The invention also comprises a method for diagnosing asthma or atopic dermatitis comprising: measuring expression of a biomarker in a sample from the subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2; wherein increased expression of the biomarker compared to a control is indicative of the disease. In one embodiment, the method further comprises measuring the expression of the one or more biomarkers selected from the group consisting of: MDC/CCL22, CCL17/TARC, CD40, CD80 and IL-19.

The invention also comprises a method for monitoring asthma or atopic dermatitis (disease state) comprising: measuring expression of a biomarker in a sample from the subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2; wherein increased expression of the biomarker compared to a control is indicative of disease progression and decreased expression of the biomarker compared to a control is indicative of disease regression. In one embodiment, the method further comprises measuring the expression of the one or more biomarkers selected from the group consisting of: MDC/CCL22, CCL17/TARC, CD40, CD80 and IL-19.

The invention also comprises a method for determining whether a treatment for asthma or atopic dermatitis is effective comprising: (a) obtaining a baseline biological sample from a subject prior to treatment; (b) measuring the level of a biomarker in the baseline biological sample by gene expression analysis or immunoassay, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2; (c) administering the treatment; (d) obtaining from the subject at least one subsequent biological sample; (e) measuring the level of the biomarker in the subsequent sample by gene expression analysis or immunoassay; (f) comparing the level of the biomarker in the subsequent biological sample with the level of the biomarker in the baseline biological sample, and (g) determining whether the treatment is effective. In one embodiment, step (b) further comprises measuring the level of a biomarker selected from the group consisting of: MDC/CCL22, CCL17/TARC, CD40, CD80 and IL-19. A decrease in the expression of the biomarker relative to a control indicates that the disease treatment is effective.

The invention also comprises a method for determining whether a treatment for asthma or atopic dermatitis is effective comprising: (a) administering an treatment to the subject; (b) measuring expression of a biomarker in a sample from said subject, wherein the biomarker is selected from the group consisting of: MMP12, LCN2, PGLYRP1, CHI3L1/YKL-40, REG3G, CD44, RNASE3, RNASE2, RNASE7, CHIA, and CHIAP2; and (c) determining whether the treatment is effective. In one embodiment, step (b) further comprises measuring the level of a biomarker selected from the group consisting of: MDC/CCL22, CCL17/TARC, CD40, CD80 and IL-19. A decrease in the expression of the biomarker relative to a control indicates that the treatment is effective.

DETAILED DESCRIPTION

Figure 1A:
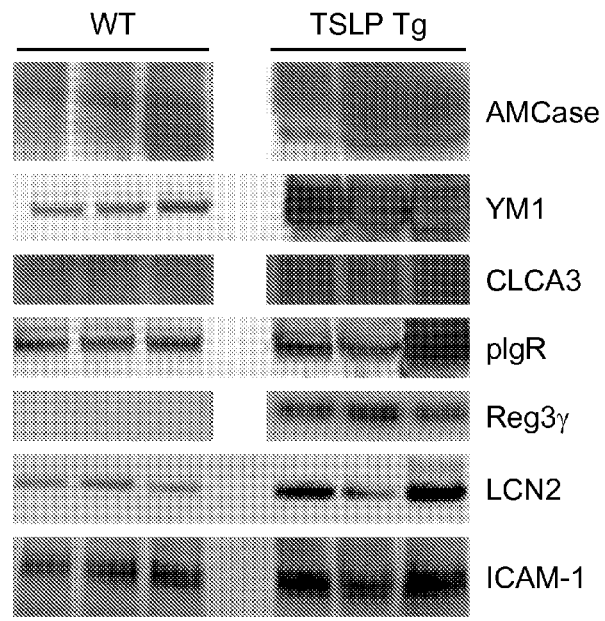
FIG. 1: Verification of putative asthma biomarkers in TSLP Tg mice. BAL fluid and lung tissue were collected from control WT and asthmatic TSLP Tg mice for further biomarker evaluation. Western blot analysis was performed on the BAL fluid of WT or TSLP Tg mice for assessment of AMCase, YM1, CLCA3, pIgR, Reg3γ, LCN2, and ICAM-1 (A), and ELISAs were used to quantify the amount of GP-39, LCN2, and ICAM-1 in BAL fluid (B). Results are representative of 3-5 independent experiments. ***, $P<0.001$.

As used herein, including the appended claims, the singular forms of words such as "a," "an," and "the," include their corresponding plural references unless the context clearly dictates otherwise.

All references cited herein are incorporated by reference to the same extent as if each individual publication, database entry (e.g. GENBANK® sequences (Computerized storage and retrieval services dealing with information relating to nucleic acid sequence data sequences) or GENEID® (scientific research in the field of genetics and genetic engineering entries), patent application, or patent, was specifically and individually indicated to be incorporated by reference. GENBANK® (Computerized storage and retrieval services dealing with information relating to nucleic acid sequence data sequences) accession numbers for nucleic acid and protein sequences referenced herein refer to the contents of the database as of the filing date of this application. Although such database entries may be subsequently modified, GENBANK® (Computerized storage and retrieval services dealing with information relating to nucleic acid sequence data sequences) maintains a public record of all prior versions of the sequences as a function of date, making such database entries an unambiguous reference to a specific sequence.

This statement of incorporation by reference is intended by Applicants, pursuant to 37 C.F.R. §1.57(b)(1), to relate to each and every individual publication, database entry (e.g. GENBANK® (computerized storage and retrieval services dealing with information relating to nucleic acid sequence data sequences) sequences or GENEID® (scientific research in the field of genetics and genetic engineering entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

I. Definitions

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell.

"Administration" and "treatment" also means in vitro and ex vivo treatments, e.g., of a cell, by a reagent, diagnostic, binding composition, or by another cell. "Treatment," as it applies to a human, veterinary, or research subject, may refer to therapeutic treatment, prophylactic or preventative measures, to research and diagnostic applications. For a relapsing/remitting-type disease like IBD, a treatment that prevents, delays or reduces severity of a relapse can be said to either "treat" the overall disease or to prophylactically "prevent" the relapse, and as such the distinction between treatment and prophylaxis is difficult. As use herein, "treatment" refers to reduction of signs or symptoms, or reduction of duration or severity, of an IBD episode active during the start of therapy, whereas "prevention" refers to the prevention, delay or reduction of severity of an IBD episode beginning after the start of therapy, although any given therapeutic regimen may be constitute both treatment and prevention as used herein. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts TSLP or its receptor, e.g., in the fluid phase or colloidal phase.

As used herein, "subject" refers to a specific individual, usually a human, of interest. A "subject" may be a human subject who is diagnosed with, or suspected of having, a disease or disorder and/or is under treatment for a disease or disorder. The term "subject" and "patient" are used interchangeably in this application.

As used herein, "biological sample" may comprise any sample obtained from a subject, including but not limited to whole blood, plasma, serum, tissue biopsy (e.g., lung or skin), sputum, bronchoalveolar lavages (BAL) cells, nasal exudate, nasal scrape or urine.

As used herein, the "expression" or "level" of a biomarker relates to the amount of biomarker polypeptide present in a sample or the amount of mRNA encoding the biomarker present in a sample.

As used herein "monitoring" refers to measuring and/or recording changes in a varying parameter.

As used herein, the term "antibody" may refer to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, antibody fragments, etc. so long as they exhibit the desired biological activity.

Antibody fragments include Fab, Fab', F(ab')$_2$, and Fv fragments; diabodies; linear antibodies; single-chain antibody molecules, e.g., sc-Fv; domain antibodies; and multispecific antibodies formed from antibody fragments. Typically, an antibody fragment or derivative retains at least 10% of its affinity for its target, e.g. no more than a 10-fold change in the dissociation equilibrium binding constant ($K_d$). Preferably, an antibody fragment or derivative retains at least 25%, 50%, 60%, 70%, 80%, 90%, 95%, 99% or 100% (or more) of its binding affinity, although any binding fragment with sufficient affinity to exert the desired biological effect will be useful. It is also intended that, when specified, an antibody fragment can include sequence variants with conservative amino acid substitutions that do not substantially alter its biologic activity.

A "TSLP antagonist" is a molecule that inhibits the activity of TSLP in any way. In some embodiments, a TSLP antagonist is an antibody or antigen binding fragment that inhibits TSLP signaling via the TSLP receptor, for example by binding to TSLP or its receptor. In other embodiments a TSLP antagonist is a small molecule or a polynucleotide, such as an antisense nucleic acid or siRNA. In another embodiment, the TSLP antagonist is a soluble TSLP receptor or a TSLP-Fc fusion protein.

Monoclonal antibodies specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies (although these same designations, depending on the context, may also indicate the human form of a particular protein). The humanized forms of rodent antibodies will generally comprise the same CDR sequences of the parental rodent antibodies, although certain amino acid substitutions may be included to increase affinity, increase stability of the humanized antibody, or for other reasons.

Antibodies also include antibodies with modified (or blocked) Fc regions to provide altered effector functions. See, e.g., U.S. Pat. No. 5,624,821; WO 2003/086310; WO 2005/120571; WO 2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies. A longer half-life may result in less frequent dosing, with the concomitant increased convenience and decreased use of material. See Presta (2005) *J. Allergy Clin. Immunol.* 116:731 at 734-35.

Antibodies also include antibodies with intact Fc regions that provide full effector functions, e.g. antibodies of human isotype IgG1, which induce complement-dependent cytotoxicity (CDC) or antibody dependent cellular cytotoxicity (ADCC) in a targeted cell.

The antibodies of the present invention also include antibodies conjugated to cytotoxic payloads, such as cytotoxic agents or radionuclides. Exemplary cytotoxic agents include ricin, vinca alkaloid, methotrexate, *Pseudomonas* exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{177}$Lu, $^{143}$Pr and $^{213}$Bi. See, e.g., U.S. Patent Application Publication No. 2006/0014225.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods.

"Effective amount" encompasses an amount sufficient to ameliorate or prevent a symptom or sign of the medical condition. Such an effective amount need not necessarily completely ameliorate or prevent such symptom or sign. Effective amount also means an amount sufficient to allow or facilitate diagnosis. An effective amount for a particular patient or veterinary subject may vary depending on factors such as the condition being treated, the overall health of the patient, the method route and dose of administration and the severity of side effects. See, e.g., U.S. Pat. No. 5,888,530. An effective amount can be the maximal dose or dosing protocol that avoids significant side effects or toxic effects. An effective amount will typically result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Allergic disease" refers to any disease caused by a hypersensitivity disorder of the immune system. It includes, without limitation, such as asthma, atopic dermatitis, Ichtyosis Prematurity Syndrome, allergic rhinitis, eosinophilic esophagitis, and Netherton Syndrome.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR Technology (Stockton Press, N.Y.). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence if it binds to polypeptides comprising the polypeptide sequence but does not bind to proteins lacking the polypeptide sequence.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

II. General

The present invention provides biomarkers for chronic asthma and TSLP treatment. The biomarkers of the invention are well known in the art, and their sequences can be found in GENBANK® (computerized storage and retrieval services dealing with information relating to nucleic acid sequence data sequences). For example, the GENBANK® (computerized storage and retrieval services dealing with information relating to nucleic acid sequence data sequences) Accession Numbers for the biomarkers of the invention are as follows:

| Gene | Human Ortholog | Genbank Accesion No. (human ortholog) |
|---|---|---|
| MMP-12 | MMP-12 | NM_002426.4 |
| LCN2 | LCN2 | NM_005564.3 |
| PGLYRP1 | PGLYRP1 | NM_005091.2 |
| CHI3L1 (YKL-40) | CHI3L1 (YKL-40) | NM_001276.2 |
| CHI3L1/YKL-40, REG3G | CHI3L1/YKL-40, REG3G | NM_198448.3 (variant 1) NM_001008387.2 (variant 2) NM_001270040.1 (variant 3) |
| CD44 | CD44 | NM_000610.3 (variant 1) NM_001001389.1 (variant 2) NM_001001390.1 (variant 3) NM_001001391.1 (variant 4) NM_001001392.1 (variant 5) NM_001202555.1 (variant 6) NM_001202556.1 (variant 7) NM_001202557.1 (variant 8) |
| EAR11 | RNASE3 (ECP; eosinophil cationic protein) | NM_002935.2 |
|  | RNASE2 (EDN; eosinophil derived neurotoxin) | NM_002934.2 |
|  | RNASE7 | NM_032572.3 |
| CHI3L3 (YM1) | CHIA (AMCASE; CHIT2; YNL0) | NM_001040623.2 NM_001258001.1 |
|  | RP11-165H20.1 | NR_003928.1 |

| Gene | Human Ortholog | Genbank Accesion No. (human ortholog) |
|---|---|---|
| CHI3L4 (YM2) | (CHIAP2 chitinase, acidic pseudogene 2) CHIA; AMCASE; CHIT2; YNL | NM_001040623.2 NM_001258001.1 |

The biomarkers of the invention can find use in several contexts. A biomarker of the invention can be used in diagnosing of asthma, in staging subjects for disease severity, and in determining treatment efficacy. In the experiments described herewith, the proximal fluids and tissues from murine and nonhuman primate (NHP) models of chronic asthma were studied to identify and qualify predictive markers of disease progression and treatment efficacy. TSLP Transgenic (Tg) mice, which express thymic stromal lymphopoietin (TSLP) under the lung-specific surfactant protein C promoter (SPC), develop hallmark features of human asthma over 12 weeks. Zhou et al., Nat. Immunol. 6:1047-53 (2005). BAL fluid, lung tissue, and sputum from TSLP Tg mice were assessed for protein and/or mRNA levels to identify putative biomarkers associated with early and chronic stages of asthma pathogenesis. Dexamethasone was administered to TSLP Tg mice with chronic disease to characterize which biomarkers are modulated with treatment. Putative disease and treatment biomarkers were then evaluated in OVA-sensitive mouse and house dust mite allergen (HDMA)-sensitive cynomologus macaque models of chronic allergic asthma before and after corticosteroid treatment. The results comprise a comprehensive study of biomarkers expressed in proximal fluids and tissues across multiple established models of asthma and at different stages of disease progression and treatment.

The biomarkers of the invention can also find use as a biomarker to select patient subpopulations likely to respond to treatment with a TSLP antagonists. The present invention demonstrates that the biomarkers of the invention levels are reverted toward non-disease levels when animals are treated with a TSLP antagonist antibody. Accordingly, allergic subjects having elevated levels of the biomarkers of the invention may be considered likely candidates for therapy with a TSLP antagonist to revert the levels of the biomarkers to non-disease levels. Conversely, allergic subjects without elevated levels of the biomarkers of the invention may be poor candidates for treatment with a TSLP antagonist.

The biomarkers of the invention can be used in subjects undergoing treatment with a TSLP antagonist, to confirm blockade of the TSLP pathway, to assess the efficacy of treatment (and modification of therapeutic regimen if necessary), and to monitor patient progress generally. If results demonstrate that a given therapeutic regimen effectively engages the target pathway in a patient, and yet fails to provide a therapeutic benefit, then it may be that TSLP signaling is of relatively little practical significance in the patient.

The biomarkers of the invention may also find in management of patients in the clinic, for example to inform modification of therapeutic regimen if necessary. A clinician may monitor the level of one or more biomarkers of the invention to help decide whether dosing with a TSLP antagonist should be increased, decreased, or made more or less frequent, depending on the degree to which the patient is responding to existing therapy. Note that reduction of the frequency of administration may constitute a reduced "dose" in that the subject will receive less drug over a given period of time, when the timeframe is longer than a single dosing interval. By measuring the levels of one or more of the biomarkers of the invention it may be possible to determine which subjects are responding favorably to treatment with a TSLP antagonist at an earlier time (i.e. sooner after treatment) than would be possible using standard clinical disease measures, some of which rely at least in part on symptomatic relief. Early discrimination of responders from non-responders allows for earlier modification of dosing or discontinuation. Early modifications of the therapeutic regimen can reduce the time to successful treatment, or reduce the risk of unnecessary exposure to an ineffective drug (with concomitant reduction in expense and side-effects).

Assessment of the efficacy of a given therapeutic regiment is important for management of patient care, and essential for evaluation of potential therapeutic agents, as in clinical trials.

III. TSLP Antagonists

Allergic diseases may be treated using antagonists of TSLP. Antagonists of TSLP include agents, such as antibodies or fragments thereof, which bind to TSLP or its receptor. The sequence of human TSLP is found, for example, at GENBANK® (computerized storage and retrieval services dealing with information relating to nucleic acid sequence data sequences) Accession No: CBX74361.

The TSLP receptor is composed of two subunits: TSLPR (CRLF2) and IL7Ralpha subunits. Reche et al., J. Immun. 167: 336-343 (2001).

In one embodiment, the TSLP antagonist is an anti-human TSLP antibody comprises the heavy and light chain variable domains of the humanized antibodies disclosed in commonly assigned International Pat. Appl. Pub. No. WO 2008/076321 or WO2011/056772.

In various embodiments the TSLP antagonists of the present invention comprise antigen binding fragments of antibodies, such as fragments of any of the TSLP antagonist antibodies referred to herein. Such fragments include, but are not limited to, Fab, Fab', Fab'-SH, Fv, scFv, F(ab')$_2$, nanobody and a diabody.

In another embodiment, the TSLP antagonist is a soluble TSLPR receptor. See, e.g., Al-Shami et al., JEM 202:829-839 (2005).

In another embodiment, the TSLP antagonist is a TSLPR-Fc fusion protein. See, e.g., Zhang et al., Clin. Exp. Immunol. 164:256-264 (2011).

IV. Determination Of Expression Levels Of Biomarkers

The methods described herein are generally applicable to determining the expression levels of biomarkers.

In one aspect, the invention involves determining whether a sample from a subject exhibits increased or decreased levels of a biomarker compared with control levels. Biomarker levels can be quantitated by any method known in the art, including but not limited to, mass spectrometry, Western blot, IHC or ELISA. Means for determining the level of the biomarker of the present invention include, but are not limited to, the methods disclosed herein, and their equivalents.

In one embodiment, biomarker protein levels are determined by Western blot (immunoblot), for example as follows. A biological sample is electrophoresed on 10% sodium dodecyl sulfate polyacrylamide gel (SDS-PAGE) and transferred (e.g. electroblotted) onto nitrocellulose or polyvinylidene fluoride (PVDF) some other suitable membrane. The membrane is then incubated with a primary antibody that binds to the biomarker protein being evaluated, washed, and optionally incubated with a detectably labeled secondary antibody that binds to the primary antibody, and optionally washed again. The presence of the secondary antibody is then detected (or primary antibody if it is detectably labeled), for example by radioactivity, fluorescence, luminescence, enzymatic activity (e.g. alkaline phosphatase or horseradish peroxidase) or other detection or visualization technique known to those of skill in the art. In one embodiment, the detectable label is used to produce an autoradiograph, which is scanned and analyzed. In other embodiments, the gel is imaged directly without the use of an autoradiograph. Observed biomarker band intensity may optionally be normalized to a control protein present in the sample, such as actin or tubulin.

In yet another embodiment, biomarker levels are determined by ELISA. In one embodiment, the sandwich ELISA, a first antibody specific for the biomarker of interest (the "capture antibody") is coated in the well of a plate (e.g. a 96-well microtiter plate), and the plate is then blocked with, e.g., bovine serum albumin (BSA) or casein. Standards or samples are pipetted into the wells so that biomarker polypeptide present in the samples can bind to the immobilized antibody. The wells are washed and a (second) biotinylated anti-biomarker antibody is added. This second anti-biomarker antibody must be able to bind to the biomarker even while the biomarker is bound to the first antibody. In other embodiments, the second antibody is the same as the first antibody, for example if the biomarker forms a multimer. In some embodiments the second antibody is a distinct, non-crossreacting antibody. In yet other embodiments the second antibody binds to an entirely separate polypeptide chain, for example when the biomarker to be detected is present as a heterodimeric complex (e.g. calprotectin). After washing away unbound biotinylated antibody, HRP-conjugated streptavidin (or some functionally equivalent detection reagent) is pipetted to the wells. Alternatively, the biotinylated antibody can be replaced with an antibody having a directly detectable label, obviating the need for the streptavidivn step. The wells are again washed, a TMB substrate solution is added to the wells, and color develops in proportion to the amount of biomarker bound. Stop solution is added to the reaction, which changes the color from blue to yellow, and the intensity of the color is measured at 450 nm. See e.g., Human IGF-BP-2 ELISA Kit from RayBiotech, Inc.; Norcross, Ga., USA; and Angervo et al., (1992) *Biochem. Biophys. Res. Comm.* 189: 1177; Kratz et al. (1992) *Exp. Cell Res.* 202: 381; and Frost et al. (1991) *J. Biol. Chem.* 266: 18082. A standard curve using known concentrations of biomarker can be used to determine the concentration of biomarker in the sample.

Other ELISA formats familiar to those in the art may also be used, such as using direct adsorption to the plate, rather than a capture antibody, to immobilize the biomarker in the microtiter well. Competitive ELISA may also be used, in which a biomarker in a sample is detected by its ability to compete with labeled biomarker molecules present in the assay solution for binding to the plate. The higher the concentration of biomarker polypeptide in the sample of interest, the more it will block the binding of labeled biomarkers, thus lowering the observed signal.

Lateral flow format immunoassays (immunochromatographic assay) may also be used, in which an aqueous sample is drawn over a surface by capillary action. The surface has a first zone in which is deposited a detection reagent (such as a detectably labeled antibody) and a second zone comprising an immobilized capture reagent (e.g. an antibody). Both the capture reagent and detection reagent specifically bind to the biomarker of interest. As the sample flows across the first zone the detection reagent is solubilized and binds to any analyte (biomarker) present in the sample to form a complex. As the sample continues to flow it contacts the second zone, where any complexes are bound to the capture reagent and concentrated. When a colored particle is used as the detectable label, the concentration of particles at the second zone results in a visible color signal. The level of analyte (biomarker) may then be assessed qualitatively or quantitatively by the intensity of the signal at the second zone.

Biomarker levels may also be determined by Radioimmunoassay (RIA). RIA involves mixing known quantities of radioactive analyte (e.g., labeled with $^{131}$I and $^{125}$I-tyrosine) with antibody to that analyte, in the presence or absence of unlabeled or "cold" analyte from a sample of interest, and measuring the amount of labeled analyte displaced. In this case the analyte is a biomarker of the present invention. Analyte in the sample will compete with labeled analyte and reduce its binding to the antibody. Unbound analyte is removed, and labeled bound analyte is quantitated. Unbound analyte can be removed, for example, by precipitating the analyte-antibody complexes with a secondary antibody directed against the primary antibody. In another embodiment, the analyte-specific antibodies can be immobilized on the walls of a test tube or microtiter well or to some other solid substrate, so that unbound analyte can be simply washed away.

Any other suitable assay format may be used to detect the biomarker of interest, such as nephelometry/turbidimetry, specifically immunoturbidimetry, which involves measurement of light scattering caused by suspended insoluble antigen (biomarker)/antibody complexes. See, e.g. U.S. Pat. No. 4,605,305. Other methods include radial immunodiffusion (RID), which is observation of a precipitin ring generated by complex formation between an antigen (biomarker) and an antibody, e.g. in an agar/agarose slab. See, e.g. U.S. Pat. No. 3,947,250. Such formats are commonly used in clinical assays.

In other embodiments, the biomarker may be detected by mass spectrometric methods. Mass spectrometric methods include time-of-flight, magnetic sector, quadrupole filter, ion trap, ion cyclotron resonance, electrostatic sector analyzer and hybrids of these. In such embodiments, the biomarker in the sample can be identified and quantified using isotope labeled identical synthetic peptides spiked into the sample. In one embodiment, the mass spectrometer is a laser desorption/ionization mass spectrometer. In laser desorption/ionization mass spectrometry, analytes are placed on the surface of a mass spectrometry probe, which presents an analyte for ionization. A laser desorption mass spectrometer employs laser energy, typically from an ultraviolet or infrared laser, to volatilize and ionize analytes for detection by the ion optic assembly. In another mass spectrometric embodiment, the sample is optionally chromatographically fractionated, and biomarker is then captured on a bio-affinity resin, e.g. a resin derivatized with an antibody. The biomarker is then eluted from the resin and analyzed by MALDI, electrospray, or another ionization method for mass spectrometry. In yet another embodiment, the sample is fractionated on an anion exchange resin and detected directly by MALDI or electrospray mass spectrometry.

In other embodiments, the level of gene expression of biomarker genes may be determined. Gene expression at the nucleic acid level can be quantitated by any method known in the art, including but not limited to, Northern blot analysis, gene chip expression analysis, or RT-PCR (real-time polymerase chain reaction). See e.g., Smith et al.

(1993) *J. Clin. Endocrin. Metab.* 77(5): 1294; Cohen et al. (1993) *J. Clin. Endocrin. Metab.* 76(4): 1031; Dawczynski et al. (2006) *Bone Marrow Transplant.* 37:589; and Clemmons et al. (1991) *J. Clin. Endocrin. Metab.* 73:727.

Northern blot analysis is a standard method for detection and quantitation of mRNA. RNA is isolated from a sample to be assayed (e.g., colonic mucosa). RNA is separated by size by electrophoresis in an agarose gel under denaturing conditions, transferred to a membrane, crosslinked, and hybridized with a labeled probe. In one embodiment of the invention, Northern blot analysis involves radiolabeled or nonisotopically detectably labeled nucleic acids as hybridization probes. In one embodiment of the invention, the membrane holding the RNA sample is prehybridized, or "blocked," prior to probe hybridization to reduce nonspecific background. Unhybridized probe is removed by washing. The stringency of the wash may be adjusted as is well understood in the art. If a radiolabeled (or luminescent) probe is used, the blot can be exposed to film for autoradiography e.g, in the presence of a scintillant. If a nonisotopic probe is used, the blot must typically be treated with nonisotopic detection reagents to develop the detectable probe signal prior to film exposure. The relative levels of expression of the genes being assayed can be quantified using, for example, densitometry or visual estimation. The observed expression level may be normalized to the expression level of an abundantly expressed control gene (e.g. ubiquitin).

In another embodiment, biomarker expression is determined using a gene chip (probe array). A biological sample of interest is prepared and hybridized to the chip, which is subsequently washed, stained and scanned. The data are then processed. Target preparation may entail preparing a biotinylated target RNA from the sample to be tested. The target hybridization step may involve preparing a hybridization cocktail, including the fragmented target, probe array controls, BSA, and herring sperm DNA. In one embodiment, the target is hybridized to the probe array for 16 hours, which probe is washed, stained with streptavidin phycoerythrin conjugate and scanned for light emission at 570 nm. The amount of light emitted at 570 nm is proportional to the target bound at each location on the probe array. Computer analysis using commercially available equipment and software is possible (Affymetrix, Santa Clara, Calif., USA).

In a different embodiment, biomarker expression is determined using real time PCR (RT-PCR). Design of the primers and probes required for RT-PCR of the biomarkers of the present invention is within the skill in the art, in light of the sequences provided herein. In one embodiment, RNA is isolated under RNAse free conditions and converted to DNA using reverse transcriptase, as is well known in the art. RT-PCR probes depend on the 5'-3' nuclease activity of (e.g., Taq) DNA polymerase to hydrolyze an oligonucleotide hybridized to the target amplicon (biomarker gene). RT-PCR probe oligonucleotides have a fluorescent reporter dye attached to the 5' end and a quencher moiety coupled to the 3' end (or vice versa). These probes are designed to hybridize to an internal region of a PCR product. During amplification, the 5'-3' nuclease activity of the polymerase cleaves the probe, decoupling the fluorescent dye from the quencher moiety. Fluorescence increases in each cycle as more and more probe is cleaved. The resulting fluorescence signal is monitored in real time during the amplification on standard, commercially available equipment. The quantity of biomarker RNA in a sample being evaluated may be determined by comparison with standards containing known quantities of amplifiable RNA.

Biomarkers or biomarker gene expression may be detected using commercially available kits, or using custom assays with commercially available anti-biomarker antibodies obtained from suppliers well known in the art, or using custom assays and antibodies raised by the investigator.

One of skill in the art would recognize that the detection means disclosed herein inherently involve the transformation of an article from one state into another state. Typically the detection means disclosed herein involve transforming an analyte (i.e. the substance to be detected, such as a biomarker polypeptide or an mRNA encoding that polypeptide) into a complex with a detection reagent (e.g. an antibody or complementary nucleic acid). For example, immunological detection means like ELISA, Western blot, etc. involve transformation of biomarker polypeptides into antigen-antibody complexes, which complex formation is essential to the detection. In another example, hybridization-based detection means like amplification (e.g. TAQMAN® (kit consisting of reagents for use in polymerase chain reaction (PCR) to quantitate the amount of initial target in nucleic acid amplification reaction), Southern/Northern blotting and gene chip-based methods involve transformation of an mRNA encoding the biomarker from a single stranded state to a double stranded state, which complex formation is essential to the detection.

In some embodiments of the present invention the samples to be compared will be obtained from the same subject, and thus will be to some degree "internally controlled." In such embodiments, the ability to discern changes in protein or gene expression levels will be limited only by the inherent precision of the assay, and will not include individual-to-individual variation. Accordingly, small differences between samples from a single subject may be statistically significant even when similar data that include individual-to-individual variation would not be.

V. Data Analysis

Expression levels of the biomarkers of the present invention may be used, depending on the samples being compared, for various purposes, including but not limited to, diagnosing disease, staging patients, monitoring disease status, selecting patients for treatment with an TSLP antagonist, confirming target engagement, and monitoring therapeutic efficacy. Typically, such methods involve comparing the level of biomarkers in sample obtained from a subject of interest (the "subject") to the level in a "control". As used herein, "level of biomarkers in a subject" and similar phrases refer to levels determined in samples obtained from the subject, e.g. skin, tissue, serum, blood, urine, feces, etc.

In light of the identification of the biomarkers provided herein, it would be within the skill in the art for medical practitioners to determine the levels of the biomarkers of the invention in a number of human subjects, both with and without allergic disease. Such data would likely be accumulated in the course of clinical trials assessing the safety and efficacy of a drug (e.g. a TSLP antagonist antibody) in question. Such biomarker data are often collected in the course of clinical trials, and represent no more than the usual level of effort expended in the art. These baseline data would also be analyzed for variability using standard statistical approaches to determine the precision of the assay(s) in question. Armed with the difference in biomarker level, and the statistical variability in the assay used to measure the biomarker, a skilled medical practitioner would be able to judge whether the level of the biomarker in a given sample was consistent with TSLP blockade.

The broad scope of this invention is best understood with reference to the following examples, which are not intended to limit the inventions to the specific embodiments.

EXAMPLE 1

Expression of Chronic Asthma Biomarkers in TSLP Transgenic Mice

Materials and Methods

Mice and In Vivo Protocols:

TSLP Tg mice, on the BALB/c background, were obtained from the laboratory of Steven Ziegler. Zhou et al., *Nat. Immunol.* 6:1047-53 (2005). Non-transgenic littermates served as control mice. BALB/c mice (for ovalbumin (OVA)-induced asthma experiments) were purchased from the Jackson Laboratory. The standard model of OVA-induced asthma described below was used. In dexamethasone-treatment experiments, 12 week-old TSLP Tg mice were injected i.p. daily for 2 weeks with 2 mg/kg dexamethasone 21-phosphate disodium salt (Sigma) in sterile PBS, or with sterile PBS alone as a control. Colonies were maintained in a specific pathogenic-free environment.

Standard model of OVA-induced asthma in mice: For the standard model of OVA-induced asthma, mice were sensitized i.p. with 50 ug of ovalbumin from chicken egg white (Sigma-Aldrich) complex to 2 mg of IMJECT® (reagents used in connection with enhancing immune responses) Alum (Pierce) in 0.15M saline (Sigma-Aldrich) on day 0 and day 14, and primed 2 times on Day 27 and 28 with saline or nebulized OVA (10 mg/mL) for 45 min per session. Mice were given a final challenge of saline or OVA (25 mg/mL) on day 29, and tissues were harvested 1 day following OVA challenge.

Pulmonary Function (Plethysmography) of Dexamethasone-Treated Mice:

Murine pulmonary responses to the non-specific bronchoconstrictor methacholine chloride were measured using Whole Body Plethysmography (WBP) (Buxco Electronics). Unrestrained mice were placed in individual chambers and exposed to nebulized methacholine (5 mg/mL) for 1 minute, and responses were recorded for the following 3 minutes. Penh was calculated to quantify lung function.

Harvest of murine BAL fluid, BAL cells, and lung tissue: BAL fluid was isolated by washing the lung (through the trachea) with 1mL of PBS. Lavage fluid was kept on ice and centrifuged at 400g for 5 min. The supernatant was frozen for cytokine analysis, and the cell pellet was resuspended in 1mL of PBS for total viable cell count by Vi-CELL (Perkin-Elmer) and cell differentials by cytospin. Slides were air-dried, fixed with 95% ethanol, and stained with Wright-Giemsa (Sigma-Aldrich). A minimum of 200 cells were counted under the microscope per slide for cell differentials. The postcaval lung lobe and BAL cells were collected and snap-frozen in liquid nitrogen for qRT-PCR analysis as described previously for tissue (Chan et al., *J. Exp. Med.* 203:2577-87 (2006)) and below for BAL cells. The single left lung lobe was excised for histology and clinical scoring as described below.

Murine Lung Histology and Clinical Scoring: Murine lungs were perfused with 10 mL of PBS via the right ventricle of the heart. The single left lung lobe was excised, fixed in 10% neutral buffered formalin, paraffin-embedded, sectioned, and stained with hematoxylin and eosin. Lung tissue was scored for hypertrophy of the airway epithelium and peribronchiolar/pervascular celluar inflammation on a scale of 0-5 by a board-certified pathologist.

mRNA isolation from BAL cells and qRT-PCR: Total RNA was isolated from BAL cells using the RNeasy method (Qiagen, Valencia, Calif.) and reverse-transcribed using WT-OVATION ® (chemicals, assays, and reagents for nucleic acid sequence amplification, sequencing and sequence analysis and detection) Pico System (NuGen Technologies, San Carlos Calif.). Primers were designed using Primer Express software (Applied Biosystem, Foster City, Calif.) or obtained commercially from Applied Biosystems (ABI). qRT-PCR was performed on 10 ng of cDNA from each sample as described previously. Chan et al., *J. Exp. Med.* 203:2577-87 (2006).

LC-MS/MS analysis of BAL fluid proteins: An equal volume of murine or cynomolgus BAL fluid was separated on a preparative 4-12% NUPAGE® (chemical preparations used for life sciences research) gel and stained with GELCODE® (kits for protein staining for use in scientific research) Coomassie Blue (Pierce). Each lane was sliced into an equal number of bands and digested with sequencing-grade modified trypsin using a PROGEST® (Odor and solid reduction powder comprised of microorganisms and enzymes to be dissolved in water to digest organic waste) (Genomic Solutions). Mass spectrometry was performed as described below. LC-MS/MS raw files were searched using the Mascot v2.1.6 software package (Matrix Sciences) against the mouse subset of the National Center for Biotechnology Information (NCBI) non-redundant protein database (updated as of August 2006) for murine BAL fluid and against the entire database (including all species, updated as of December 2007) for monkey BAL fluid. Additional detail on search methods is provided in an Online Repository. Categorization of proteins by function was performed using INGENUITY® (life science research of chemical and biological systems) Pathway Analysis (INGENUITY® (life science research of chemical and biological systems) Systems).

Mass Spectrometry: Mass spectrometry was performed using a LCQ Deca Ion Trap (ThermoElectron), a 48-well Paradigm AS1 autosampler (Michrom bioresources), and a Paradign MS4 HPLC system (Michrom Bioresources). The column was packed with Vydac C18 resin (5 micron beads, 300 Å pores), 10 cm long with a 15 micron tip (New Ojectives). The chromatographic separation was performed using a linear gradient elution. Search parameters included no restriction on molecular weight or pI, fixed modification of cysteine residues (carbamidomethylation), variable modification of methionine residues (oxidation), a peptide mass tolerance of +/−1.5 Daltons, a fragment mass tolerance of +/−0.8 Dlatons, and one missed tryptic cleavage. Protein identification was based on at least two matching peptides. Protein hits with only one matching peptide were reviewed manually and included as positive identifications when a stretch of at least 4 b or y ions present.

Western blot analysis of BAL fluid samples: Western blot analysis was performed on BAL fluid samples. 200 uL of each BAL fluid sample was acetone precipitated in 4 volumes of cold acetone overnight and resuspended in 1× NUPAGE® (chemical preparations used for life sciences research) LDS sample loading buffer. An equal amount was separated on a 4-12% NUPAGE® (chemical preparations used for life sciences research) gels, and gels were electroblotted onto PVDF membranes overnight at 10V in NUPAGE® (chemical preparations used for life sciences research) transfer buffer. Membranes were blocked in 5% fat-free milk in TBS/T (10mM TrisHC1 pH 7.5, 100 mM NaC1, 0.1% TWEEN® 20 (polysorbate 20)) for 1 hour and incubated with specific antibodies according to the manufacturer's instructions in 1% milk in TBS/T for another 2 hours. Blots were incubated with HRP-labeled secondary antibodies (chicken anti-goat) IgG, R&D Systems, Minneapolis, Minn. or donkey anti-rabbit Ig-G, GE Healthcare, Piscataway, N.J.) in 1% milk in TB S/T for another hour and detection was performed with ECL+(GE Healthcare). Primary antibodies used included anti-mouse LCN2, anti-mouse sICAM-1, anti-human sICAM-1 (for monkey studies), anti-mouse GP-39, anti-mouse YM1, and anti-mouse pIgR (all from R&D Systems); and anti-mouse UG, anti-mouse AMCase, anti-human AMCase (for monkey studies), anti-mouse CLCA3, and anti-human CLCA1 (for monkey studies) (all from Santa Cruz Biotechnology, Santa Cruz, Calif.). Polyclonal anti-mouse Reg3γ was generated at Schering-Plough Biopharma. After autoradiography visualization, membranes were dried and scanned on a Typhoon 9400 (GE Healthcare) for ECL+(457 nm excitation and 520BP40 emission). Image analysis was conducted using ImageQuant v5.2 (GE Healthcare) and band intensity reported as sum of pixel values above background.

ELISAs: Mouse LCN2, GP-39, sICAM-1, and YM1 proteins were quantified using QUANTIKINE® (in vitro immunoassay kits) or DUOSET® (biological reagents for use in research applications to identify cytokines by immunoassay) ELISA kits (R&D Systems) using a Vmax spectrophotometer with SoftMax Pro software (Molecular Devices); mouse IL-4, IL-5, and IL-13 were measured using a Luminex 100 machine with LINCOPLEX® (panels for taking immunoassay measurements and testing cytokine and endocrine hormones) multiplex kits (Millipore) and analyzed with MasterPlex software (Miraibio). Monkey YKL-40 was quantified via ELISA (Quidel), analyzed as above.

Statistical Analysis: The unpaired or paired two-tailed t test was performed using GraphPad Prism version 4.02 (GraphPad Software) to determine average±standard error of the mean. P<0.05 was considered statistically significant. *, P<0.05; , P<0.01; *, P<0.001.

Protein in BAL Fluid of TSLP Tg Mice

As murine BAL cells, a surrogate for human induced-sputum cells, had not previously been examined for their utility in disease and treatment biomarker identification, we examined the gene expression profiles of BAL cell mRNA for biomarker and chemokine/chemokine receptor genes indicative of a chronic asthma phenotype.

TSLP Tg mice begin to develop pathophology characteristic of asthma at 5 weeks of age. By 9 weeks of age, all of the hallmarks of chronic human asthma, including pulmonary eosinophilia, production of Th2 cytokines, airway fibrosis, and hyperplasia of airway epithelium are present. Bronchoalveolar lavages (BAL) was performed on the lungs of 9-week old control or TSLP Tg mice, the cellular fraction of the BAL was removed, and the BAL fluid phase was analyzed by mass spectrometry. Using INGENUITY® (life science research of chemical and biological systems) Pathway Analysis, proteins were categorized by known function into enzymes (30%), transporters (10%), peptidases (6%), transcription regulators (2%), cytokines (2%), kinases (2%), phosphatases (1%), growth factors (1%), transmembrane receptors (1%), or ion channels (1%). Proteins that did not fall into a specific functional group were termed "other" (44%) and consisted of a variety of proteins with uncharacterized or unclassified functions. Forty-four proteins were found to be upregulated in the BAL fluid, compared to non-Tg wild-type littermate controls. See Table IA.

Figure 1B:
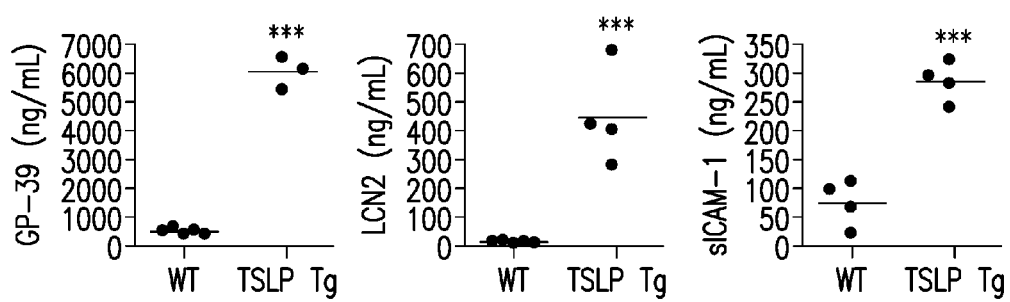

Mass spectrometry is semi-quantitative, and a subset of 18 putative biomarkers was further analyzed by more quantitative approaches: acidic mammalian chitinase (AMCase; gene name Chia), YM1 (YM1; Chi3l3), chloride channel regulator 3 (CLCA3; Clca3), the polymeric immunoglobulin receptor (pIgR; Pigr), regenerating islet-derived 3 gamma (Reg3γ; CHI3L1/YKL-40, REG3G), lipocalin 2 (LCN2; Lcn2), and intercellular adhesion molecule 1 (ICAM-1; Icam1), cartilage glycoprotein 39 (GP-39; Chi3l1), YM2 (YM2; Chi3l4), eosinophil cationic protein (ECP; Ear11), resistin-like beta (RETNLβ; Retnlb), eosinophil major basic protein (EMBP; Prg2), eosinophil peroxidase (EPX; Epx), matrix metallopeptidase 12 (MMP12; Mmp12), the Fc fragment of IgG binding protein (FCGBP; Fcgbp), lactoferrin (Ltf), Peptidoglycan recognition protein (Pglyrp1), kallikrein 1 (KLK1; Klk1). The proteins were chosen based upon availability of reagents and their previous association or lack of association with pulmonary diseases. Protein levels in BAL fluid were verified by western blot or ELISA. In western blots of BAL fluid, expression of AMCase, YM1, CLCA3, pIgR, Reg3γ, LCN2, and ICAM-1 was increased by (FIG. 1A), and LCN2, GP-39, and sICAM-1 were all highly upregulated as measured by ELISA (FIG. 1B).

qRT-PCR Validation of Biomarkers in BAL Cells

BAL cells were collected from 9 week old TSLP Tg mice, and expression of the 18 targets analyzed by western blot and ELISA along with four additional putative biomarkers (Scgb1a1 (Secretoglobin family 1A member 1, i.e. uteroglobin (UG) or Clara Cell-specific 10 kD protein (CC-10)), Egfr (Epidermal growth factor receptor, EGFR), Itln2 (Intelectin-2, ITLN2), and Ctsh (Cathepsin H, CTSH)) were evaluated using qRT-PCR (Table II). qRT-PCR analysis showed a large range of relative expression and fold change that could generally be divided into "High" (>6-fold increase) and "Intermediate" (1.5- to 6-fold change) expression groups. Eosinophil activation genes Prg2 (EMBP), Epx, and Ear11 (ECP) were all highly upregulated in BAL cells, not surprising as eosinophils constitute over 80% of the BAL cells of TSLP Tg mice. Chi3l4 (YM2), Clca3, Ear11 (ECP), and Retnlb mRNA were also over 100-fold upregulated in BAL cells. Expression of Mmp12, Fcgbp, CHI3L1/YKL-40, REG3G, and Klk1 were also highly expressed. Scgb1a1 (UG) exhibited high expression levels in WT mice, and was further increased 8.55-fold in BAL cells from CSP-TSLP Tg mice. The majority of targets exhibited an intermediate level of expression, and Chia (AMcase) was not upregulated.

qRT-PCR Validation of Biomarkers in Lung Tissue

Proteins in BAL fluid could originate from lung tissue, as well as BAL cells, and therefore expression of the 18 putative biomarkers detected by protein analysis were examined in the lung tissue of age-matched control versus TSLP Tg mice using qRT-PCR (Table VI). Chi3l4, Ear11, Retnlb, and Clca3 showed the highest upregulation at the mRNA level (fold-change >100); Prg2, Epx, Mmp12, Chia, Chi3l3, Fcgbp, and CHI3L1/YKL-40, REG3G also fell into the "High" category, whereas Ltf, Pglyrp1, Pigr, Klk1, Lcn2, and Chi3l1 displayed "Intermediate" upregulation. It was surprising that Chi3l1 (GP-39) and Lcn2 (LCN2) were only 1.85- and 2.22-fold upregulated at the mRNA level, as average protein concentrations of GP-39 and LCN2 were 11- and 30-fold increased, respectively, in TSLP Tg mouse BAL fluid (FIG. 1B). Interestingly, although sICAM-1 was highly upregulated at the protein level via ELISA (FIG. 1B), Icam1 was not modulated at the mRNA level (data not shown). Taken together, these results show that the 18 selected proteins all function as biomarkers of chronic asthma. They also indicate that qRT-PCR analysis of lung tissue mRNA is effective in assessing certain biomarkers such as Chi3l4, Ear11, Retnlb, and Clca3, but that protein assays may be more valuable in ascertaining differences in proteins such as GP-39, LCN2, or ICAM-1 that exhibit more discernable separations at the protein rather than mRNA level.

Biomarker Expression in OVA Sensitized and Challenged Mice

Putative biomarkers identified in SPc-TSLP Tg mice were verified in wild-type mice sensitized and challenged with ovalbumin (OVA). The putative biomarkers were similarly upregulated in the two different murine models of asthma. See Table III and Table IV.

Biomarker Induction in Early Asthma

TSLP Tg mice begin to develop asthma at 5 weeks of age and develop characteristics of chronic asthma over the subsequent 4 weeks. At 5 weeks of age, the mice exhibit mucus production and minor cellular inflammation around airways and vasculature but lack the massive inflammation, tissue remodeling, airway hypertrophy, and eosinophilia present at 9 weeks. Lung tissue was therefore collected from five (5) and nine (9) week-old mice, and qRT-PCR was performed for the set of 18 biomarkers to assess expression during early and chronic stages of the disease progression (Table V). 9 week old mice had 11 biomarkers in the "High" category, only 5 biomarkers assigned to the "High" category in 5 week old mice (Table III). Clca3, Chi3l4 (YM2), and Ear11 (ECP) were increased over 100-fold at 5 weeks. The relative expression of Retnlb was increased 16-fold at 5 weeks, but increased 212-fold at 9 weeks. Upregulation of Fcgbp was similar at both ages (14- or 11-fold increased). The results indicate that CLCA3, YM2, ECP, RETNLβ, and FCGBP are expressed early in asthma pathogenesis.

Chemokine and Chemokine Receptor Signature of BAL Cells

As BAL cells are a representation of the cellular constituents of the asthmatic lung, we reasoned that further examination of the chemokine and chemokine receptor genes present in the BAL cells of TSLP Tg mice would help us identify a "cellular signature" that could prove valuable in characterizing the type of cellular inflammation present in the lung and thus the best course of treatment. Towards this goal, we examined chemokine and chemokine receptor genes that are known to participate in asthmatic responses.

CCR3 (CD193) is highly expressed on eosinophils and also detectable on Th2 cells, binding chemokines CCL5 (RANTES), CCL8 (monocyte chemotactic protein-2), CCL11 (Eotaxin-1), CCL22 (macrophage-derived chemokine), and CCL24 (Eotaxin-2). See Rothenberg et al., *Annu. Rev. Immunol.* 2006; 24:147-74; Blanchard et al., *Adv. Immunol.* 2009; 101:81-121; Heath et al., *J. Clin. Invest.* 1997; 99:178-84; Bochner et al., *J. Allergy Clin. Immunol.* 1999; 103:527-32, Lee et al., *J. Allergy Clin. Immunol.* 2007; 120:1110-7; De Lucca et al., *Curr. Opin. Drug Discov. Devel.* 2006; 9:516-24; Pease et al., *Curr. Drug Targets* 2006; 7:3-12; Schuh et al., *Cytokine Growth Factor Rev.* 2003; 14:503-10; Bisset et al., *Curr. Opin. Pulm. Med.* 2005; 11:35-42; and Garcia et al., *Curr. Allergy Asthma Rep.* 2005; 5:155-60.

CCR4 is found on memory Th2 cells and binds CCL22, whereas CCR6 is found on eosinophils and memory Th2 cells. See Garcia et al., *Curr. Allergy Asthma Rep.* 2005; 5:155-60; Heijink et al., *Curr. Opin. Pharmacol.* 2005; 5:227-31; Chantry et al., *Curr. Drug Targets Inflamm. Allergy* 2002; 1:109-16; Rothenberg et al., *Annu. Rev. Immunol.* 2006; 24:147-74; and Blanchard et al., *Adv. Immunol.* 2009; 101:81-121.

Consistent with their receptor expression, CCL5, CCL8, CCL11, and CCL24 are important in eosinophil trafficking and activation, whereas CCL22 functions to recruit Th2 cells to the lung. See Rothenberg et al., *Annu. Rev. Immunol.* 2006; 24:147-74; Blanchard et al., *Adv. Immunol.* 2009; 101:81-121; Heath et al., *J. Clin. Invest.* 1997; 99:178-84; Bochner et al., *J. Allergy Clin. Immunol.* 1999; 103:527-32, Pease et al., *Curr. Drug Targets* 2006; 7:3-12; Schuh et al., *Cytokine Growth Factor Rev* 2003; 14:503-10; Bisset et al., *Curr. Opin. Pulm. Med.* 2005; 11:35-42; and Garcia et al., *Curr. Allergy Asthma Rep.* 2005; 5:155-60; Heijink et al., *Curr. Opin. Pharmacol.* 2005; 5:227-31; Chantry et al., *Curr. Drug Targets Inflamm. Allergy* 2002; 1:109-16 and Weber et al., *J. Immunol.* 1995; 154:4166-72.

qRT-PCR expression analysis of BAL cell mRNA from WT and TSLP Tg mice revealed that Ccr3 was over a thousand-fold upregulated in the asthmatic TSLP Tg mice (Table II), depicting the large eosinophil population in the BAL. Although not increased as much as Ccr3, chemokine receptors Ccr4 and Ccr6 were also over 10-fold upregulated. Consistent with the expression of their receptors, chemokines Ccl5, Ccl8, Ccl11, Ccl22, and Ccl24 were also highly upregulated (between 7- and several hundred-fold). In contrast, Cxcr1 and Cxcr2, receptors for neutrophil-attracting chemokines, were not increased (data not shown). These results demonstrate that the chemokine and chemokine receptor profile of BAL cells accurately represents the cellular composition of an asthmatic lung.

Biomarkers Modulated with Dexamethasone Treatment

Having identified a set of disease biomarkers in the BAL fluid, lung tissue mRNA, and BAL cell mRNA of asthmatic mice, we next sought to determine which biomarkers are reduced with treatment. As corticosteroid treatments have been proven highly effective as the standard of care for the disease, we administered systemic dexamethasone daily for two weeks to 12-week old TSLP Tg mice. In contrast to previous studies using dexamethasone to prevent the onset of inflammation associated with OVA-induced asthma, 12 week-old TSLP Tg mice have chronic, extensive asthma-associated inflammation and pathology present for ~3-5 weeks before treatment. Additionally, as these mice express TSLP in the lung constitutively, the underlying cause of the disease continues during treatment. In this manner, TSLP Tg mice can be considered a better surrogate model of human asthma, where therapy is started after symptoms and pathology exist, and the causal sources of the disease continue during treatment.

Figure 2A:
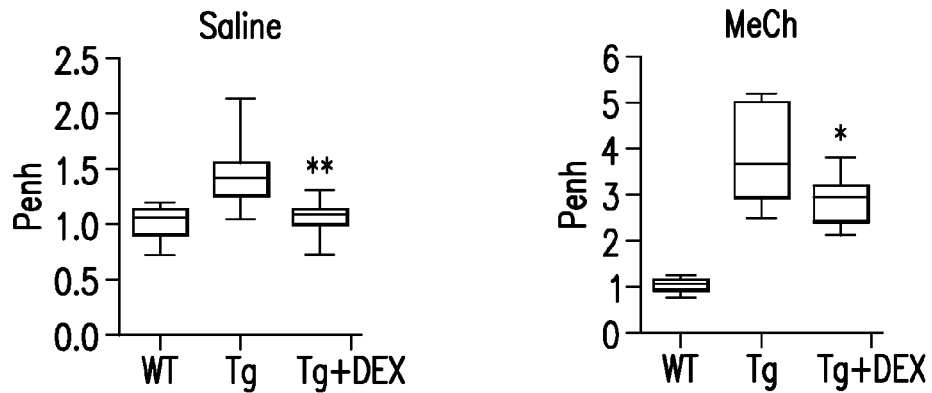
FIG. 2: Reduction of asthma symptoms upon dexamethasone treatment in TSLP Tg mice. TSLP Tg mice were treated daily with 2 mg/kg dexamethasone (DEX) i.p. for 2 weeks. Lung function was measured in WT ("WT"), TSLP Tg ("Tg"), or DEX-treated TSLP Tg mice ("Tg+DEX") by whole body plethysmography upon saline or 5 mg/mL methacholine chloride challenge (A). Lung tissue was harvested and the weight of the superior lung lobe was measured (B). H&E stained lung tissue was scored for hypertrophy of the airway epithelium and peribronchiolar/perivascular cellular inflammation on a scale of 0-5 by a board-certified pathologist (C). The total number of BAL cells was determined using trypan blue exclusion criteria on a Vi-CELL counter, and the proportion of eosinophils in the BAL was enumerated by Wright-Giemsa staining of cytospun cells. A minimum of 200 cells were counted. Results presented are the combined data points of 3 independent experiments with a grand total of 12 mice per group. *, $P<0.05$; , $P<0.01$; *, $P<0.001$.
Figure 2B:
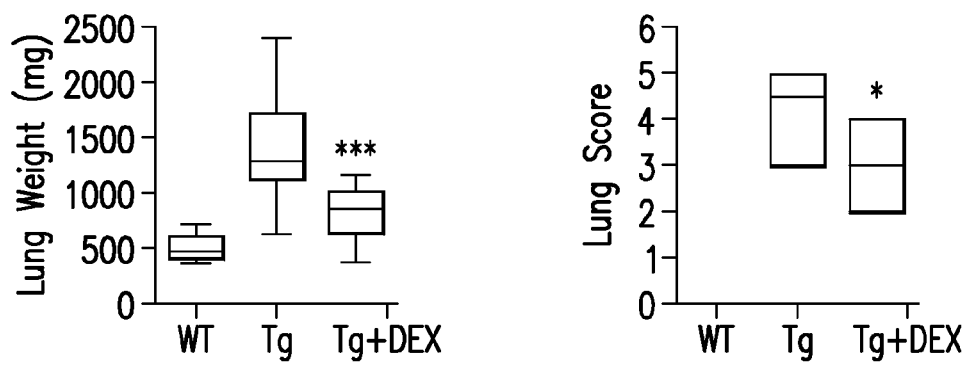
Figure 2C:
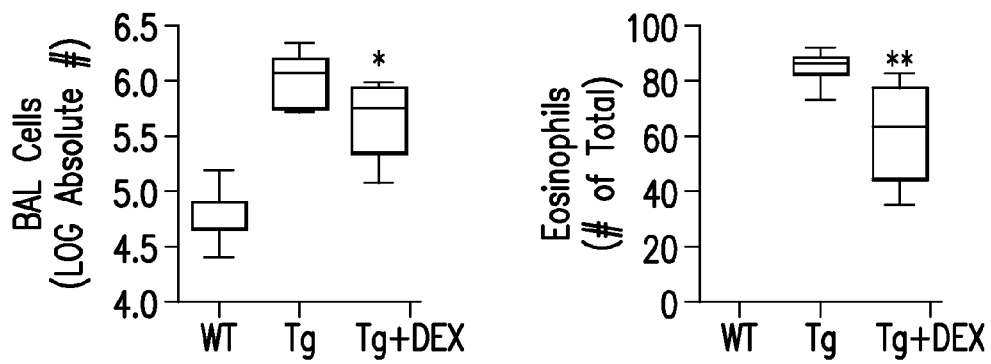

FIGS. 3 and 4 shows the reduction of asthma symptoms upon dexamethasone treatment in TSLP Tg mice. TSLP Tg mice were treated daily with 2 mg/kg dexamethasone (DEX) i.p. for 2 weeks. Lung function was measured in WT ("WT"), TSLP Tg ("Tg"), or DEX-treated TSLP Tg mice ("Tg+DEX") by whole body plethysmography upon saline or 5 mg/mL methacholine chloride challenge (FIG. 2A). Lung tissue was harvested and the weight of the superior lung lobe was measured (FIG. 2B). H&E stained lung tissue was scored for hypertrophy of the airway epithelium and peribronchiolar/perivascular cellular inflammation on a scale of 0-5 by a board-certified pathologist (FIG. 2C). The total number of BAL cells was determined using trypan blue exclusion criteria on a Vicell counter (FIG. 2D), and the proportion of eosinophils in the BAL was enumerated by Wright-Giemsa staining of cytospun cells (FIG. 2E). A minimum of 200 cells were counted.

As shown in FIG. 2A, TSLP Tg mice exhibit worse basal lung function (Penh), as measured by whole body plethysmography, and have high Penh values when challenged with a very small dose (5 ug/mL) of methacholine chloride. Dexamethasone treatment of the TSLP Tg mice significantly improved both basal and challenged lung function. Correspondingly, dexamethasone treatment significantly reduced lung weight (FIG. 2B), lung pathology score (FIG. 2C), total number of BAL cells (FIG. 2D), and percentage of BAL eosinophils (FIG. 2E) in TSLP Tg mice. Although significantly decreased, these parameters were not absent with treatment, allowing us to discern which biomarkers are more quickly modulated with treatment.

Figure 3A:
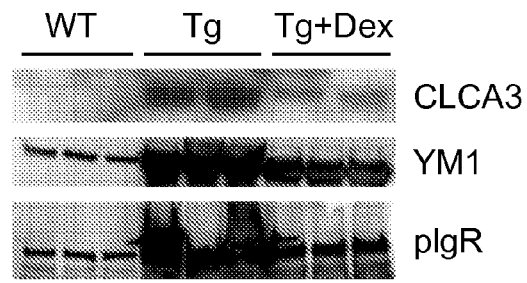
FIG. 3: Downregulation of biomarkers in dexamethasone-treated TSLP Tg mice. TSLP Tg mice were treated with dexamethasone for 2 weeks, at which time BAL fluid was collected for western blot analysis (A) of CLCA3, YM1, and pIgR or ELISA (B) of GP-39, LCN2, sICAM-1, and YM1. qRT-PCR of lung tissue (C) and BAL cells (D) was performed for biomarker genes, and expression of chemokine (E) and chemokine receptor (F) genes was also assayed by qRT-PCR of lung tissue. Percentages indicated represent the % reduction of the respective biomarker in dexamethasone-treated TSLP Tg mice ("Tg+DEX"), compared to control-treated TSLP Tg mice ("Tg"). Results are representative of 3 independent experiments. *, P<0.05; , P<0.01; *, P<0.001.
Figure 3B:
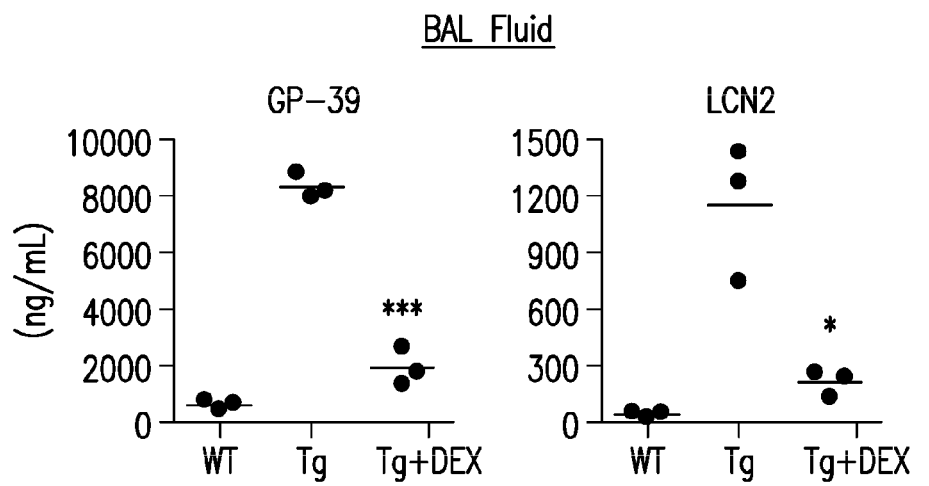
Figure 3B:
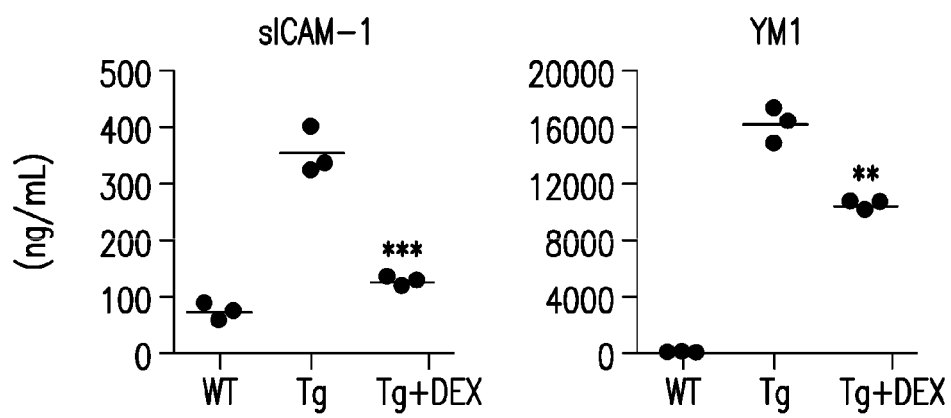
Figure 3C:
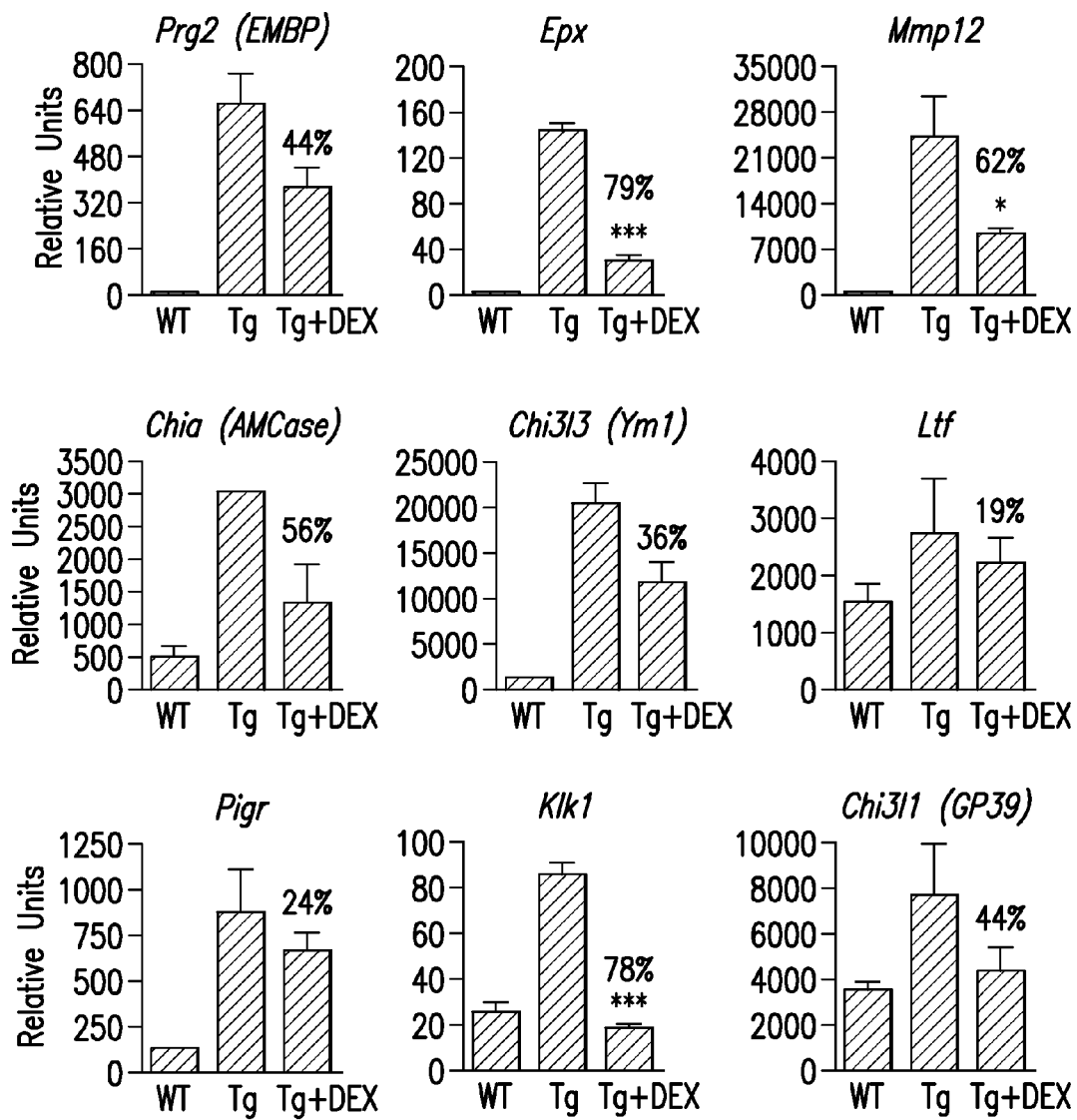

Several biomarkers were downregulated in the BAL fluid of dexamethasone-treated TSLP Tg mice, including CLCA3, YM1, and pIgR (via western blot, FIG. 3A), as shown previously (Zhao et al., Int. Arch. Allergy Immunol. 2007; 142:219-29), and GP-39, LCN2, sICAM-1, and YM1 (via ELISA, FIG. 3B). Interestingly, although Chi3l4 (YM2), Ear11, Retnlb, and Clca3 showed the highest fold-upregulation of any of the biomarkers in lung tissue from TSLP Tg mice (Table I), none of these were modulated with dexamethasone treatment at the mRNA level (data not shown). In contrast, several of the other biomarkers in the "High" lung biomarker category were reduced with treatment: Prg2 (EMBP), Epx, Mmp12, Chia (AMCase), and Chi3l3 (Ym1) were downregulated (FIG. 3C), although expression of Fcgbp and CHI3L1/YKL-40, REG3G—also in the "High" lung biomarker category—was unaffected (data not shown). In the "Intermediate" lung biomarker group, Ltf, Pigr, Klk1, and Chi3l1 (GP-39) were all reduced with dexamethasone (FIG. 3C), whereas expression of Pglyrp1 and Lcn2 were not diminished at the mRNA level (data not shown), despite that LCN2 protein levels were significantly lowered (FIG. 3B).

Figure 3D:
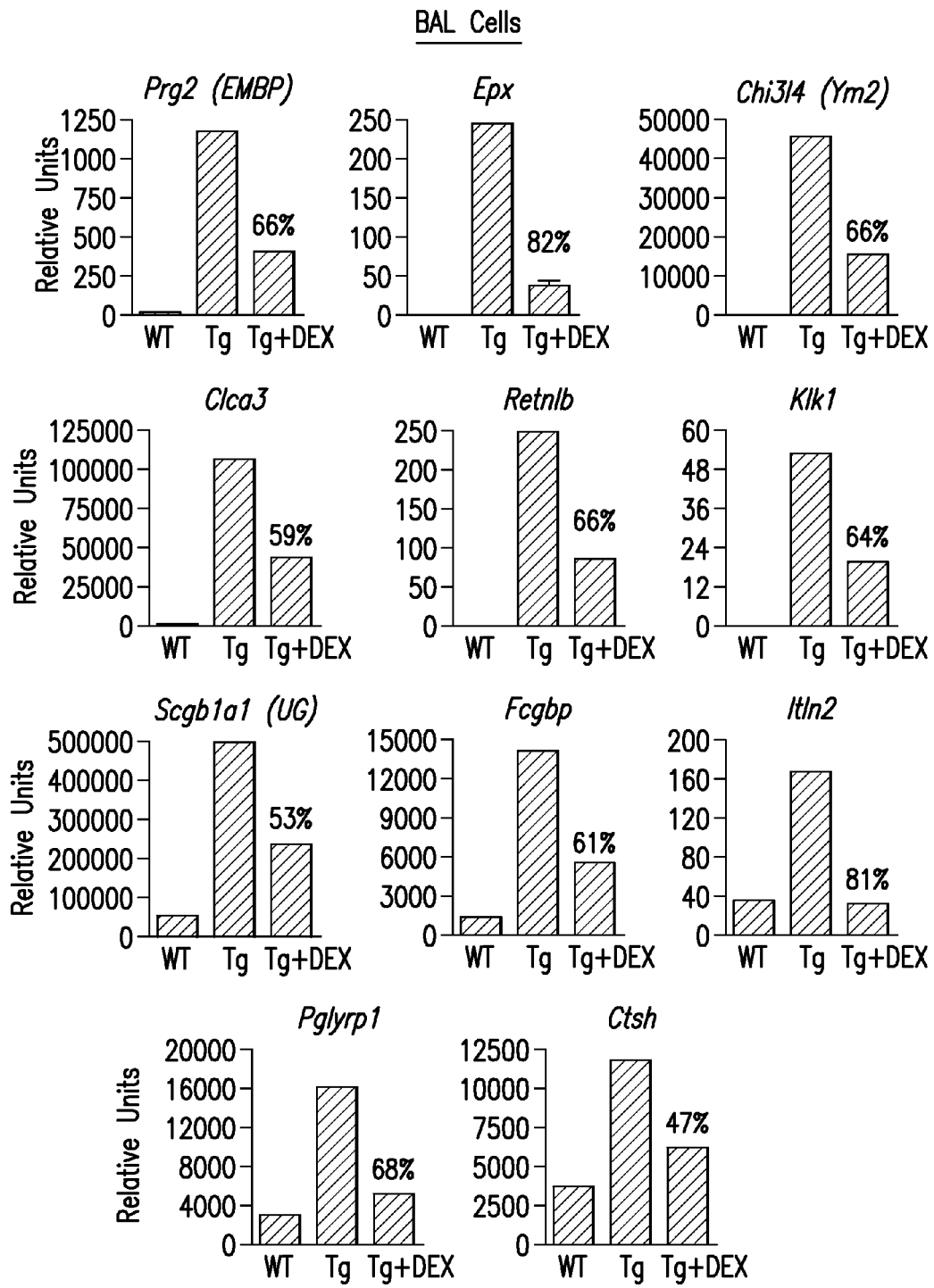

In BAL cell mRNA from dexamethasone-treated mice, the biomarkers with the largest increase (Prg2, Epx, Chi3l4, Clca, Retnlb, and Klk1) were all downmodulated with treatment (FIG. 3D). Ear1 was not reduced, which was surprising as Prg2 and Epx, the other two eosinophil activation genes, were reduced in both lung tissue and BAL cell mRNA. Scgb1a1 (UG), Fcgbp, Itln2, Pglyrp1, and Ctsh were also reduced in BAL cell mRNA upon treatment (FIG. 3D). Together, these results show that corticosteroid treatment quickly reduces the highest upregulated biomarkers in BAL cells but not lung tissue, indicating that BAL cells may be more useful for monitoring asthma treatment biomarkers.

Figure 3E:
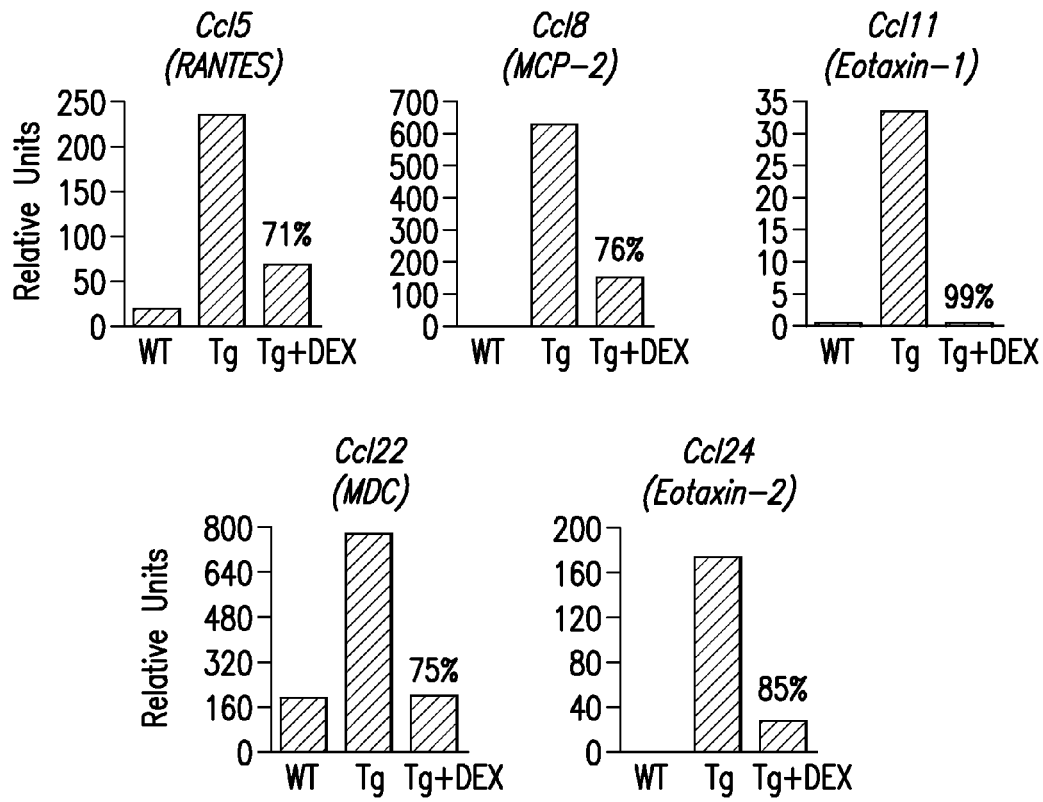
Figure 3F:
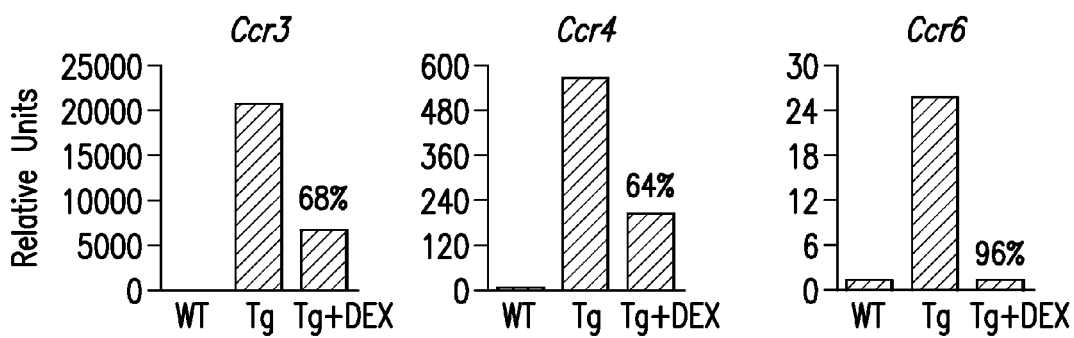

As the percentage of eosinophils and total number of BAL cells were reduced in TSLP Tg mice treated with dexamethasone (FIGS. 2D and E), we next examined chemokine and chemokine receptor genes in BAL cell mRNA. Th2 cell chemokine Ccl22 and eosinophil chemokines Ccl5, Ccl8, Ccl11, and Ccl24 were all reduced with dexamethasone treatment (FIG. 3E). Consistent with the reduction in chemokine genes, chemokine receptors Ccr3, Ccr4, and Ccr6 were all downregulated with treatment (FIG. 3F). Thus, corticosteroid treatment reduces a subset of disease biomarkers in BAL fluid, lung tissue, and BAL cells and affects the expression of eosinophil and lymphocyte chemokine and chemokine receptor genes present in BAL cell mRNA of asthmatic TSLP Tg mice.

Table I: Lists of proteins identified by mass spectrometry in BAL fluid from TSLP Tg mice and WT littermates. Proteins were classified as having greater (Table IA), similar (Table IB), or decreased (Table IC) expression in TSLP Tg mice compared to WT mice.

TABLE IA

| Protein | NCBI GI Protein Accession Number |
| --- | --- |
| 14-3-3 Tau | 38077229 |
| Adipsin | 673431, 7304867 |

TABLE IA-continued

| Protein | NCBI GI Protein Accession Number |
| --- | --- |
| aldo-keto reductase family 1, member B3 | 1351911 |
| annexin A1 | 113945, 6754570 |
| apoH | 231558 |
| biliverdin reductase B | 21450325 |
| cathepsin H | 13905172, 3929819, 7106279 |
| C7 | 38077624 |
| chloride channel calcium activated 3 | 8567336 |
| cyclophilin B | 2118329, 6755142 |
| cyclophilin C | 6679441 |
| enolase 1 | 12963491, 13637776, 8101734 |
| eosinophil-associated, ribonuclease A family, member 2 | 15420983, 6681251 |
| epidermal growth factor receptor | 10880776 |
| factor H | 19072788, 20071242 |
| fatty acid binding protein 4 | 14149635 |
| Fc gamma BP | 26346705 |
| fibronectin 1 | 28479106 |
| GDI 2 | 6679987 |
| GDI 3 | 12841706 |
| glutathione peroxidase 1 | 27807638, 6680075 |
| GP-39 | 13124008, 26341984 |
| Fizz1 | 10048446, 12841171 |
| hypothetical Glyoxalase/Bleomycin resistance protein | 21313080, 12849397 |
| intelectin 2 | 28932914 |
| Lactotransferrin | 202291 |
| L-carnitine dehydratase | 34328352 |
| leucine-rich alpha-2-glycoprotein | 16418335 |
| lipocalin 2 | 34328049 |
| Lungkine | 6755436 |
| Pigment epithelium-derived factor precursor | 1747298, 31981504, 3355888, 46397639 |
| peptidoglycan recognition protein 1 | 6679293 |
| PIGR | 31981570, 8099665 |
| profilin 1 | 26344071, 6755040 |
| regenerating islet-derived 3 gamma | 6755310 |
| S100A8 | 1200246, 7305453 |
| S100A9 | 6677837 |
| serpinB6 | 6678097 |
| transglutaminase 2 | 6678329 |
| tumor endothelial marker 7-related precursor | 15987503 |
| ubiquitin-conjugating enzyme E2 | 42741690 |
| YM1 | 11140877, 6753416 |
| YM2 | 18254403, 21553079 |
| YNL | 6934190 |

TABLE 1B

| | |
| --- | --- |
| 14-3-3 protein beta | 3065925, 3143974, 7106546 |
| 14-3-3 epsilon | 31981925 |
| 14-3-3 zeta | 1526539, 1841387, 26341272, 6756041 |
| abhydrolase domain containing 14b | 27753960 |
| Actin | 12697526, 12852068, 15076949, 15284015, 2724046, 29123076, 30425250, 37653273, 38079974, 38089227, 38089775, 46401542, 49864, 6752952, 71620, 728792, 728796, 728798, 809561, 8850209, 90263 |
| Afamin | 20072386, 21553101 |
| aldehyde dehydrogenase II | 191804 |
| aldo-keto reductase family 1, member A4 | 10946870 |
| annexin A3 | 26354887, 7304887, 71766 |
| annexin A5 | 13277612, 3318923, 4139939, 4139951, 6753060 |
| antithrombin III | 18252782 |
| apo A4 | 29477189, 6680702, 12836356 |

TABLE 1B-continued

| | |
|---|---|
| beta-2 microglobulin | 114775 |
| C3 | 23956044, 28175786 |
| C5 | 13278268, 26348393, 6754164 |
| calmodulin | 12851157 |
| carbonic anhydrase 2 | 12832236, 26344335, 31981657, 33243954 |
| carbonic anhydrase 3 | 31982861 |
| Carboxylesterase | 14331135, 17512488, 2921308, 38089545 |
| Ceruloplasmin | 38614350, 6680997 |
| coagulation factor II (prothrombin) | 6753798 |
| cofilin 1 | 12861068, 6680924 |
| cyclophilin A | 38074758, 38077290, 38078688, 38080301, 6679439 |
| cysteine and glycine-rich protein 1 | 6681069, 6681069 |
| cystatin B | 6681071 |
| delta-aminolevulinic acid dehydratase | 3642647 |
| destrin | 7441446, 9790219 |
| Down syndrome cell adhesion molecule-like protein | 19852058 |
| dnaK-type molecular chaperone Hsc70 | 42542422, 476850 |
| esterase 1 | 10946842, 16716505, 18088156, 22135640, 38089547, 6679689, 92052 |
| factor B | 6996919 |
| fatty acid binding protein 3 | 51267, 6753810 |
| ferritin heavy chain | 111625 |
| ferritin light chain | 12832085 |
| fetuin A | 112459, 2546995, 7304875 |
| fetuin Beta | 112459, 10947006 |
| four and a half LIM domains 1 | 22137390, 25091271, 6753864 |
| FK506 binding protein 1a | 6679803 |
| Gelsolin | 18606238, 26354755 |
| glutathione peroxidase 3 | 15011841 |
| glutathione S-transferase, alpha 4 | 12859131, 12859396, 20141353, 6754082 |
| glutathione S-transferase, mu 1 | 6754084 |
| glutathione S-transferase, mu 2 | 6680121 |
| glutathione S-transferase, mu 6 | 7110613 |
| glutathione S-transferase, M7-7 | 28494710 |
| glutathione S-transferase omega 1 | 6754090 |
| Haptoglobin | 6016254, 8248739, 8850219 |
| heat shock protein 1 | 6754254 |
| Hemoglobin | 122639, 12845853, 12846616, 12852164, 2118940, 92361 |
| Hemopexin | 1881768, 22022646, 23956086 |
| Kininogen | 12963497, 40715898, 40715900, 4071590097, 41235784, 92436, 92471 |
| Lysozyme | 7305247, 8393739 |
| malate dehydrogenase 1 | 31982178, 37589957 |
| nucleoside diphosphate kinase 1 or 2 | 127984, 9852058 |
| murinoglobin 1 | 1168250, 31982171, 38174651 |
| orosomucoid 1 or 2 | 6679182, 6754950 |
| p25 alpha (CGI-38 protein) | 13385968, 38079976 |
| peroxiredoxin 1 | 6754976, 7948999 |
| peroxiredoxin 5 | 26345188, 6746357, 6755114 |
| Peroxiredoxin 6 | 3219774, 3789944, 4139186, 6671549 |
| Plasminogen | 31982113 |
| Pzp | 34785996, 6680608 |
| SAP | 134198, 91294 |
| Secretoglobin | 6755947 |
| serpinaA3K | 34980957 |
| serpin A6 | 15489028, 6680856 |
| serpin C1 | 18252782 |
| serpin F1 | 1747298, 31981504, 3355888, 46397639 |
| superoxide dismutase 1 | 45597447 |
| surfactant associated protein B | 22296601 |
| surfactant associated protein D | 6677921 |
| Thyroglobulin | 2055388, 3319332, 6678335, 69232 |
| Transferring | 18204720 |
| Transgelin 2 | 9910901 |
| triosephosphate isomerase | 68423, 1864018, 6678413 |
| Vitamin D binding protein | 30802101, 38080263, 476569, 111243 |

TABLE IC

| | |
|---|---|
| 14-3-3 gamma | 3065929 |
| Acyl-CoA-binding protein | 6681137 |
| aldehyde dehydrogenase A1 | 1083586, 28386049, 42560536, 7304881, 9755362 |
| aldolase 1 | 27695278 |
| aldose reductase | 1351911, 31981909 |
| Apo A1 | 6753096, 1245804 |
| Rho GDP dissociation inhibitor (GDI) alpha | 13435747, 26344461, 31982030 |
| C9 | 755764, 15375312 |
| carbonyl reductase 2 | 6671688 |
| cytochrome C, somatic | 6681095 |
| D-dopachrome tautomerase | 6753618 |
| fructose-bisphosphate aldolase | 42490830, 6671539, 68186, 7548322 |
| glucose phosphate isomerase 1 | 6680067 |
| Phosphatidylethanolamine-binding protein | 12841975 |
| Phosphoglycerate mutase 1 or 2 | 12844989, 20178035 |
| Prothrombin | 6753798 |
| RAGE | 6671525, 7441748 |
| RNase 4 | 10946868 |
| selenium binding protein 1 or 2 | 18848341, 9507079, 22164798 |
| serpin D1 | 6680183 |
| serpin F2 | 6679383 |
| serpin G1 | 1772998 |
| SH3-binding domain glutamic acid-rich protein like | 9910548 |
| thioether S-methyltransferase | 12850108, 6678281 |
| thioredoxin 1 | 6755911, 12841560 |
| similar to SEC14-like protein 3 | 38091283 |
| TI-225 | 1167510, 38079256, 38083720, 38089459, 38089953 |
| ZAG | 7304911 |

TABLE II qRT-PCR analysis of selected biomarker genes in BAL cells of WT or TSLP Tg mice.

| Gene Name | WT* | TSLP Tg* | Fold Change |
|---|---|---|---|
| High | | | |
| Prg2 (EMBP) | 0.06 | 693.53 | 12002.03 |
| Epx | 0.01 | 158.61 | 10813.69 |
| Chi3l4 (YM2) | 4.42 | 5363.04 | 1212.53 |
| Clca3 | 20.39 | 21345.26 | 1046.82 |
| Retnlb | 0.14 | 47.54 | 336.66 |
| Klk1 | 0.20 | 40.09 | 203.08 |
| Earl1 | 70.06 | 9318.96 | 133.00 |
| Mmp12 | 212.80 | 8432.78 | 39.63 |
| Scgb1a1 (UG) | 465.03 | 5788.91 | 12.45 |
| Fcgbp | 259.87 | 2468.60 | 9.50 |
| CHI3L1/YKL-40, REG3G | 136.93 | 1046.53 | 7.64 |
| Intermediate | | | |
| Itln2 | 83.58 | 352.78 | 4.22 |
| Pglyrp1 | 1293.16 | 5300.36 | 4.10 |
| Egfr | 10.62 | 39.39 | 3.71 |
| Pigr | 1560.77 | 5523.00 | 3.54 |
| Chi3l3 (YM1) | 27002.91 | 95553.46 | 3.54 |
| Chi3l1 (GP-39) | 0.69 | 1.95 | 2.81 |
| Ctsh | 1665.02 | 3950.66 | 2.37 |
| Lcn2 | 1198.03 | 2425.46 | 2.02 |
| Ltf | 591.75 | 1065.15 | 1.80 |
| Chemokine Genes | | | |
| Ccl5 (RANTES) | 193.70 | 1363.41 | 7.04 |
| Ccl8 (MCP-2) | 0.34 | 231.05 | 689.65 |
| Ccl11 (Eotaxin-1) | 0.06 | 9.72 | 164.35 |
| Ccl22 (MDC) | 6.33 | 63.40 | 10.02 |
| Ccl24 (Eotaxin-2) | 0.05 | 28.51 | 609.57 |
| Ccr3 (CD193) | 0.05 | 175.28 | 3748.13 |
| Ccr4 (CD194) | 1.16 | 13.28 | 11.47 |
| Ccr6 (CD196) | 6.56 | 79.27 | 12.09 |

*relative expression units, normalized to ubiquitin

TABLE III

Comparison of biomarker gene upregulation in 9 week old TSLP Tg mice, OVA-challenged mice, and 5-week old TSLP Tg mice (with developing asthma).

| Gene Name | TSLP Tg vs. WT (9 weeks) | Fold Change OVA vs. Saline | TSLP Tg vs. WT (5 weeks) |
|---|---|---|---|
| Chi3l4 (YM2) | 608.31 | 2377.87 | 383.34 |
| Earl1 | 316.71 | 276.77 | 101.52 |
| Retnlb | 212.57 | 270.7 | 16.35 |
| Clca3 | 152.85 | 526.22 | 427.13 |
| Prg2 (EMBP) | 38.45 | 9.05 | 2.16* |
| Epx | 37.31 | 10.33 | 1.09 |
| Mmp12 | 26.81 | 37.67 | 3.04* |
| Chia (AMCase) | 18.6 | 9.76 | 1.68* |
| Chi3l3 (YM1) | 18.06 | 18.03 | 3.41* |
| Fcgbp | 14.28 | 13.33 | 11.09 |
| CHI3L1/YKL-40, REG3G | 13.29 | 2.83* | 1.88* |
| Ltf | 5.71* | -1.37 | 2.16* |
| Pglyrp1 | 5.66* | 2.21* | 1.6* |
| Pigr | 3.24* | 3.97* | 2.32* |
| Klk1 | 2.61* | 4.11* | 1.39 |
| Lcn2 | 2.22* | 2.81* | 1.16 |
| Chi3l1 (GP-39) | 1.85* | 2.17* | 1.03 |

Bold-faced text indicates a value that falls into the "High" expression category (>6-fold upregulated);
asterisks indicate a value that falls into the "Intermediate" expression category (1.5- to 6-fold increased).

TABLE IV qRT-PCR analysis of selected biomarker genes in Saline or OVA-challenge mouse lung tissue.

| Gene Name | Saline* | OVA* | Fold Change |
|---|---|---|---|
| High | | | |
| Chi3l4 (YM2) | 1.5 ± 0.70 | 3566.68 ± 820.67 | 2377.87 |
| Clca3 | 6.52 ± 0.93 | 3428.78 ± 179.39 | 526.22 |
| Earl1 | 20.78 ± 6.36 | 5751.26 ± 303.18 | 276.77 |
| Retnlb | 0.54 ± 0.17 | 144.94 ± 8.95 | 270.7 |
| Mmp12 | 196.34 ± 35.63 | 7396.15 ± 635.09 | 37.67 |
| Chi3l3 (YM1) | 752.3 ± 42.83 | 13566.21 ± 572.54 | 18.03 |
| Fcgbp | 53.65 ± 2.68 | 715.14 ± 41.25 | 13.33 |
| Epx | 2.87 ± 0.32 | 29.66 ± 4.46 | 10.33 |
| Chia (AMCase) | 395.20 ± 42.82 | 3857.7 ± 422.35 | 9.76 |
| Prg2 (EMBP) | 19.11 ± 1.49 | 172.9 ± 26.36 | 9.05 |
| Intermediate | | | |
| Klk1 | 12.89 ± 0.84 | 52.96 ± 3.95 | 4.11 |
| Pigr | 206.56 ± 36.52 | 820.66 ± 69.28 | 3.97 |
| CHI3L1/YKL-40, REG3G | 585.09 ± 152.69 | 1654.29 ± 151.29 | 2.83 |
| Lcn2 | 2440.28 ± 257.78 | 6864.99 ± 365.70 | 2.81 |
| Pglyrp1 | 46.55 ± 3.08 | 103.0 ± 4.413 | 2.21 |
| Chi3l1 (GP-39) | 3324.99 ± 144.23 | 7207.64 ± 221.13 | 2.17 |
| No or Negative Change | | | |
| Icam1 | 3234.65 ± 424.99 | 4096.66 ± 211.15 | 1.27 |
| Ltf | 1631.02 ± 264.83 | 1185.75 ± 113.07 | -1.37 |

*relative expression units, normalized to ubiquitin

TABLE V qRT-PCR analysis of selected biomarker genes in the lung tissue of 5-week old WT or TSLP Tg mice, which exhibit developing asthma.

| Gene Name | WT* | TSLP Tg* | Fold Change |
|---|---|---|---|
| High | | | |
| Clca3 | 4.42 ± 2.17 | 1888.01 ± 712.69 | 427.13 |
| Chi3l4 (YM2) | 0.75 ± 0.22 | 288.25 ± 73.22 | 383.34 |
| Earl1 | 5.14 ± 1.51 | 521.59 ± 128.66 | 101.52 |
| Retnlb | 0.24 ± 0.12 | 3.99 ± 1.50 | 16.35 |
| Fcgbp | 41.83 ± 3.70 | 463.94 ± 138.61 | 11.09 |
| Intermediate | | | |
| Chi3l3 (YM1) | 554.47 ± 46.98 | 1889.16 ± 832.03 | 3.41 |
| Mmp12 | 151.9 ± 7.57 | 461.72 ± 229.31 | 3.04 |
| Pigr | 53.56 ± 11.82 | 124.02 ± 28.81 | 2.32 |
| Ltf | 200.49 ± 49.34 | 433.96 ± 143.91 | 2.16 |
| Prg2 (EMBP) | 13.27 ± 4.48 | 28.67 ± 7.16 | 2.16 |
| CHI3L1/YKL-40, REG3G | 268.07 ± 134.64 | 504.58 ± 135.54 | 1.88 |
| No or Negative Change | | | |
| Chia (AMCase) | 617.32 ± 47.49 | 1038.85 ± 272.26 | 1.68 |
| Pglyrp1 | 54.57 ± 4.06 | 87.08 ± 6.61 | 1.60 |
| Klk1 | 76.84 ± 11.24 | 107.17 ± 24.30 | 1.39 |
| Lcn2 | 1684.04 ± 55.07 | 1947.97 ± 273.07 | 1.16 |
| Epx | 4.77 ± 0.98 | 5.20 ± 0.68 | 1.09 |
| Chi3l1 (GP-39) | 2751.35 ± 185.36 | 2824.22 ± 473.45 | 1.03 |
| Icam1 | 2826.16 ± 198.63 | 1994.37 ± 123.1 | -1.42 |

*relative expression units, normalized to ubiquitin

TABLE VI qRT-PCR analysis of selected biomarker genes in WT or TSLP Tg mouse lung tissue.

| Gene Name | WT* | TSLP Tg* | Fold Change |
|---|---|---|---|
| High | | | |
| Chi3l4 (YM2) | 2.39 ± 1.13 | 1453.11 ± 511.55 | 608.31 |
| Ear11 | 12.19 ± 3.31 | 3860.82 ± 1173.10 | 316.71 |
| Retnlb | 0.32 ± 0.14 | 68.08 ± 34.40 | 212.57 |
| Clca3 | 16.04 ± 8.13 | 1172.93 ± 335.42 | 152.85 |
| Prg2 (EMBP) | 19.09 ± 5.69 | 734.1 ± 181 | 38.45 |
| Epx | 6.25 ± 3.59 | 233.2 ± 64.89 | 37.31 |
| Mmp12 | 193.27 ± 14.53 | 5182.02 ± 1774.17 | 26.81 |
| Chia (AMCase) | 395.56 ± 23.63 | 7358.75 ± 1636.71 | 18.6 |
| Chi3l3 (YM1) | 478.25 ± 39.94 | 8639.59 ± 437.79 | 18.06 |
| Fcgbp | 45.13 ± 0.95 | 644.46 ± 67.23 | 14.28 |
| CHI3L1/YKL-40, REG3G | 55.92 ± 16.52 | 743.43 ± 335.41 | 13.29 |
| Intermediate | | | |
| Ltf | 229.35 ± 62.47 | 1309.18 ± 297.88 | 5.71 |
| Pglyrp1 | 58.59 ± 2.65 | 333.6 ± 28.62 | 5.66 |
| Pigr | 137.32 ± 21.13 | 445.02 ± 42.49 | 3.24 |
| Klk1 | 32.80 ± 5.10 | 85.77 ± 12.95 | 2.61 |
| Lcn2 | 1439.38 ± 161.21 | 3195.21 ± 203.18 | 2.22 |
| Chi3l1 (GP-39) | 2862.49 ± 195.24 | 5300.17 ± 442.57 | 1.85 |

*relative expression units, normalized to ubiquitin

Previous studies identifying murine biomarkers of asthma have mainly relied upon the OVA-induced asthma model. While very fruitful in deciphering the mechanisms of asthma, the model has been criticized for having a few potential shortcomings. The standard or acute model of OVA-induced asthma generally administers aerosolized OVA three times in a one-week period, which induces the cellular activation and goblet cell hypertrophy/activation but not the extensive tissue remodeling characteristic of human asthma. Chronic models of OVA-induced asthma provoke collagen deposition and extensive tissue remodeling but can induce a state of partial tolerance rather than increased cellular inflammation. Thus, we chose to utilize TSLP Tg mice, a different model of chronic asthma. These mice constitutively express TSLP under a lung-specific promoter, and as TSLP sits at the top of a cascade that leads to production of IL-4, IL-5, and IL-13 and activation of eosinophils and Th2 cells, TSLP Tg mice present with all the characteristic properties of asthma. Zhou et al., *Nat. Immunol.* 6:1047-53 (2005); Liu et al., *Annu. Rev. Immunol.* 2007; 25:193-219. In addition, as TSLP is constitutively expressed in the lung, these mice continue to exhibit progressively worse asthma symptoms throughout their lives. In this way, TSLP Tg mice are a better surrogate of human asthma than the OVA-induced asthma model. Using this mouse model, we characterized proteins in BAL fluid that could function as biomarkers of asthma.

The majority of proteins identified in BAL fluid from TSLP Tg mice were enzymes, and several of these and related proteins were selected for follow-up. Acidic mammalian chitinase (AMCase; gene name Chia), cartilage glycoprotein 39 (GP-39; Chi3l1), YM1 (Chi3l3), and YM2 (Chi3l4) are all members of the chitinase or chitinase-like family and have previously been associated with asthma, although YM1 and YM2 do not as yet have an identified human orthologue. See Lee et al., *J. Exp. Med.* 2009; 206(5):1149; Shuhui et al., *Int. Arch. Allergy Immunol.* 2009; 149:369-77; and Chupp et al., *N. Engl. J. Med.* 2007; 357:2016-27.

Matrix metallopeptidase 12 (MMP12; Mmp12) is another enzyme with elastolytic activity involved in the local accumulation of cellular inflammation in the lung. See Lee et al., *J. Exp. Med.* 2009; Shuhui et al., *Int. Arch. Allergy Immunol.* 2009; 149:369-7; Chupp et al., *N. Engl. J. Med.* 2007; 357:2016-27; Greenlee et al., *Physiol Rev.* 2007; 87:69-98; Lanone et al., *J. Clin. Invest.* 2002; 110:463-74.

Mucus production and airway remodeling are two key characteristics of asthma, so proteins representing these processes were also chosen as putative biomarkers: Fc fragment of IgG binding protein (FCGBP; Fcgbp), although not yet characterized in the lung, has a mucin-like structure, and chloride channel regulator 3 (CLCA3; Clca3), the murine homologue of human CLCA1, has been implicated in airway goblet cell hyperplasia and mucus production. See Harada et al., *J. Biol. Chem.* 1997; 272:15232-41; Long et al., *Am. J. Respir. Cell. Mol. Biol.* 2006; 35:357-65; and Kim et al., *Pharmacology* 2007; 80:219-26.

In addition, resistin-like beta (RETNLβ; Retnlb) is thought to play a role in airway fibrosis, and kallikrein 1 (KLK1; Klk1) is a serine protease that may be involved in generating mediators of airway hyperresponsiveness. See Renigunta et al., *FEBS Lett.* 2006; 580:900-3; Mishra et al., *Am. J. Physiol. Lung Cell. Mol. Physiol.* 2007; 293:L305-13; Lauredo et al., *Am. J. Physiol. Lung Cell. Mol. Physiol.* 2004; 286:L734-40; and Clements et al., *Crit. Rev. Clin. Lab. Sci.* 2004; 41:265-312.

The polymeric immunoglobulin receptor (pIgR; Pigr) was also chosen due to its important role in delivering IgA, the major immunoglobulin at mucosal surfaces, across the respiratory epithelium. See Phalipon et al., *Trends Immunol.* 2003; 24:55-8; and Salvi et al., *Clin. Exp. Allergy* 1999; 29:1597-605.

Several proteins involved in the recognition of and defense against microbes were upregulated in the BAL fluid of the asthmatic TSLP Tg mice, and a subset of these (peptidoglycan recognition protein 1 (PGLYRP1; Pglyrp1), regenerating islet-derived 3 gamma (Reg3γ; CHI3L1/YKL-40, REG3G), Lactoferrin (LTF; Ltf), and Lipocalin 2 (LCN2; Lcn2)) was also chosen for further analysis. See Cole et al., *Am. J. Respir. Med.* 2002; 1:249-59; Chan et al., *J. Immunol.* 2009; 182:4947-56; Liu et al., *J. Biol. Chem.* 2000; 275:24490-9; and Brandl et al., *J. Exp. Med.* 2007; 204:1891-900.

Eosinophils are highly involved in the pathophysiology of asthma, and a subset of eosinophil-associated genes was selected. Intercellular adhesion molecule 1 (ICAM-1; Icam1) is expressed on the vascular endothelium and is involved in the adhesion of chemotaxing leukocytes, while eosinophil cationic protein (ECP; Ear11), eosinophil peroxidase (EPX; Epx), and eosinophil major basic protein (EMBP; Prg2) are three eosinophil-associated activation proteins. See Rothenberg and Hogan, *Annu. Rev. Immunol.* 2006; 24:147-74; and Blanchard and Rothenberg, *Adv. Immunol.* 2009; 101:81-121.

Whereas several of these proteins have been well characterized in asthmatic responses, very little is known about the function of others, such as FCGBP, Reg3γ, LCN2, and LTF, in the asthmatic lung. Uteroglobin is an anti-inflammatory protein constitutively produced by airway epithelial cells, and EGFR is a receptor for members of the epithelial growth factor family also expressed by the airway epithelium, although the secreted form of EGFR is thought to act as an antagonist. CTSH is an amino peptidase produced by lung macrophages, and ITLN2 is a secreted protein of unknown function.

Some of the targets chosen have been described in association with asthma (e.g. CLCA3, YM1, YM2, AMCase) but several that had not been characterized as being possible asthma biomarkers (e.g. KLK1, Reg3γ, ITLN2, LTF). See Zhao et al., *Proteomics* 2005; 5:2799-807; Di Valentin et al., *Am. J. Physiol. Lung Cell. Mol. Physiol.* 2009; 296:L185-97; Jeong et al., *J. Korean Med. Sci.* 2005; 20:579-85; Zhang et al., *J. Proteome Res.* 2009 8(4):1631-8; Fajardo et al., *Am. J. Respir. Crit. Care Med.* 2004; 170:477-84; Wong et al., *Int. Arch. Allergy Immunol.* 2008; 147:179-89 and Novershtern et al., *Am. J. Respir. Cell Mol. Biol.* 2008; 38:324-36.

We verified these proteins with western blot assays and ELISAs, when available, and performed qRT-PCR of lung tissue for the entire set of biomarkers, allowing us to examine mRNA versus protein expression. Interestingly, mRNA upregulation did not always mirror results obtained at the protein level: ICAM-1, for instance, was significantly increased at the protein level but not modulated at the mRNA level, while other biomarkers, such as LCN2 or GP-39, were highly upregulated at the protein level but only ~2-fold increased via qRT-PCR analysis (FIG. 2 and Table VI). As such, biomarkers in the "Intermediate" expression category, although only upregulated between 1.8- and 7-fold, should not be overlooked as they could give more discernable differences at the protein rather than mRNA level.

Whereas most studies pertaining to asthma biomarker identification and validation have used BAL fluid and lung tissue as proximal fluids/tissues, we thought that the examination of BAL cell mRNA from TSLP Tg mice could be particularly fruitful in following the expression of asthma biomarkers. As continued patient participation in clinical trials or therapies is closely associated with the invasiveness of the protocol, we reasoned that BAL cells—considered a murine surrogate for human induced-sputum cells—were worth analyzing because human sputum cells are more easily acquired than lung biopsies for biomarker testing. Interestingly, genes in the "High" lung expression category also fell into the same category of BAL cell mRNA expression (Table VI and II), suggesting that the cellular infiltrate in the lung likely contributes to the expression of these biomarkers. As eosinophils constitute over 80% of the cells in the BAL of TSLP Tg mice, it was not surprising that eosinophil activation genes Prg2 (EMBP), Epx, and Ear11 were very highly increased in BAL cell mRNA. However, epithelial-associated genes (such as Clca3 or Retnlb) were also in this category, suggesting possible epithelial cell contamination, although Chia, the gene coding for AMCase, was not expressed in BAL cell mRNA, despite that AMCase is highly expressed in epithelial cells. See Hartl et al., *J. Biol. Chem.* 2008; 283:33472-82; Elias et al., *J. Allergy Clin. Immunol.* 2005; 116:497-500. Taken together, our results suggest that BAL cell analysis may be useful in monitoring disease biomarkers, and that subsets of BAL cells may be a non-traditional source of several proteins during asthma.

We also attempted to show that BAL cell mRNA could be used to generate a "cellular signature" representative of the asthmatic airway constituents through examination of chemokine and chemokine receptor genes. In TSLP Tg mice, neutrophils are quite rare and generally represent <3% of the BAL cell subsets. Correspondingly, Cxcr1 and Cxcr2, receptors present on neutrophils, were not expressed in BAL cell mRNA. Ccr3 and Ccr6, receptors on eosinophils, and Ccr4, present on Th2 cells, were enhanced in asthmatic mice, however, and dexamethasone treatment reduced expression of these receptors. Thus, examination of BAL cell mRNA could function to both identify airway infiltrates and monitor treatment. Our model of chronic asthma is characterized by eosinophilia, but the identification of a BAL "cellular signature" can also be extended to diagnose neutrophilic lung diseases or changes in the BAL cell constituents during the progression or treatment of the disease.

An interesting dichotomy appeared upon comparison of lung tissue and BAL cell mRNA expression in dexamethasone-treated TSLP Tg mice. Treatment reduced symptoms of asthma, but the most-highly upregulated lung biomarker genes were unmodulated. Taken together with the observation that these same genes are highly upregulated in 5 week-old TSLP Tg mice during the early development of asthma, it is likely that Clca3, Chi3l4 (YM2), and Ear11 are the first biomarkers to increase during disease and the last biomarkers to decline in response to therapy. Therefore, these are likely excellent disease biomarkers but poor biomarkers of early response to treatment in lung tissue. On the other hand, biomarkers such as GP-39, LCN2, sICAM-1, and YM1 or Epx, Mmp12, and Klk1, which are significantly downregulated upon treatment in TSLP Tg mouse BAL fluid and lung tissue mRNA, respectively, are good indicators of early therapeutic intervention. Similarly, most of the biomarkers increased in BAL cell mRNA are lessened with treatment and could function in a similar capacity.

EXAMPLE 2

Expression of Chronic Asthma Biomarkers in a Cynomolgus Model of Asthma

Materials and Methods

House mite allergen (HDMA)-induced asthma in nonhuman primates: Juvenile macaques (Cynomolgus fascicularis, 30 to 42 months of age) were purchased from Alphagenesis (Yemassee, S.C.). Animals were sensitized to HDMA over a 7.5 month period by intraperitoneal injection of 312 AU Dermatophagoides pteronyssinus extract (Greer Laboratories, Lenoir, N.C.) absorbed to IMJECT® (reagents used in connection with enhancing immune responses) Alum (Pierce, Rockford, Ill.) administered every two weeks until HDMA-specific IgE titers approached levels in control allergic serum, and then at 4-week intervals until aeroallergen challenge. At this time, animals were challenged with nebulized HDMA (1 to 2500 AU/mL for 4 minutes) at a concentration that induced an early asthmatic response, defined as a 100% increase in lung resistance, 40% decrease in dynamic compliance, or decline in arterial oxygen saturation to ≤70%. Airway inflammation and reactions to nebulized histamine and methacholine 24 hours after allergen challenge were measured periodically to confirm chronic asthmatic responses. Wardle-Fick methods were used to obtain BAL fluid. BAL cells were then separated from the fluid phase. Mass spectrometry compared BAL fluid from sensitized animals before and after HDMA challenge. In corticosteroid treatments experiments, animals were challenged with HDMA and BAL fluid was collected 24 hours later ("Pre"). Animals then received weekly doses of methylprednisolone succinate (4.5 mg/kg intramuscularly) for two weeks, followed by a single dose of methylprednisolone acetate (10 mg/kg i.v.) one week later at the time of allergen challenge. BAL fluid was collected 24 hours following challenge ("Post"). Animal husbandry was conducted under USDA guidelines. All protocols were approved by the Institutional Animal Care and Use Committee of East Carolina University.

Figure 4A:
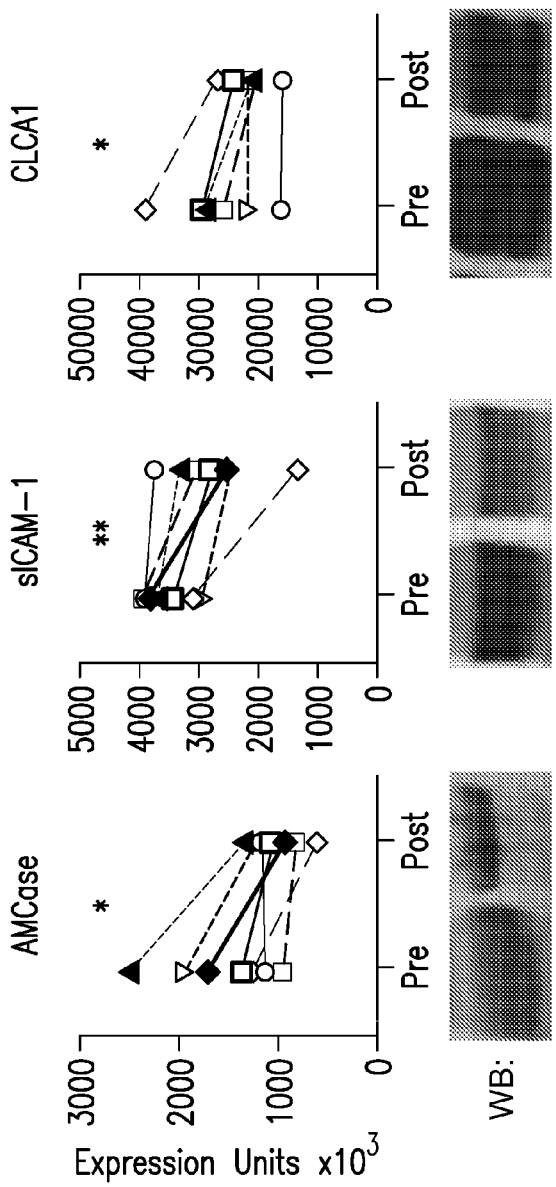
FIG. 4: Reduction of disease biomarkers in HDMA-challenged monkeys following corticosteroid treatment, and final summary of biomarker analyses. BAL fluid was collected from HDMA-challenged monkeys either before ("Pre") or after ("Post") 2 weeks of corticosteroid therapy. Western blot ("WB") for AMCase, sICAM-1, and CLCA1 was performed, and band intensities were quantified using a Typhoon scanner (A). Representative western blot results are also shown. BAL fluid GP-39 was assayed via ELISA (B). Each animal is represented by different symbol. *, P<0.05; , P<0.01; *, P<0.001.

Western blot ("WB") for AMCase, sICAM-1, and CLCA1 was performed as described in Example 1, and band intensities were quantified using a Typhoon scanner (FIG. 4A).

Figure 4B:
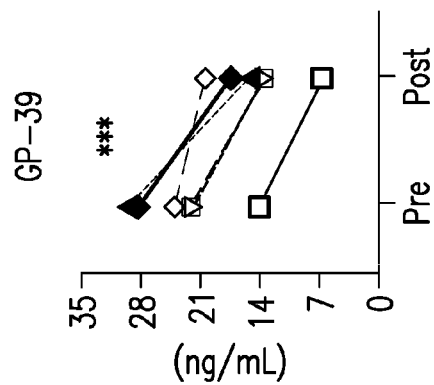
Figure 5A:
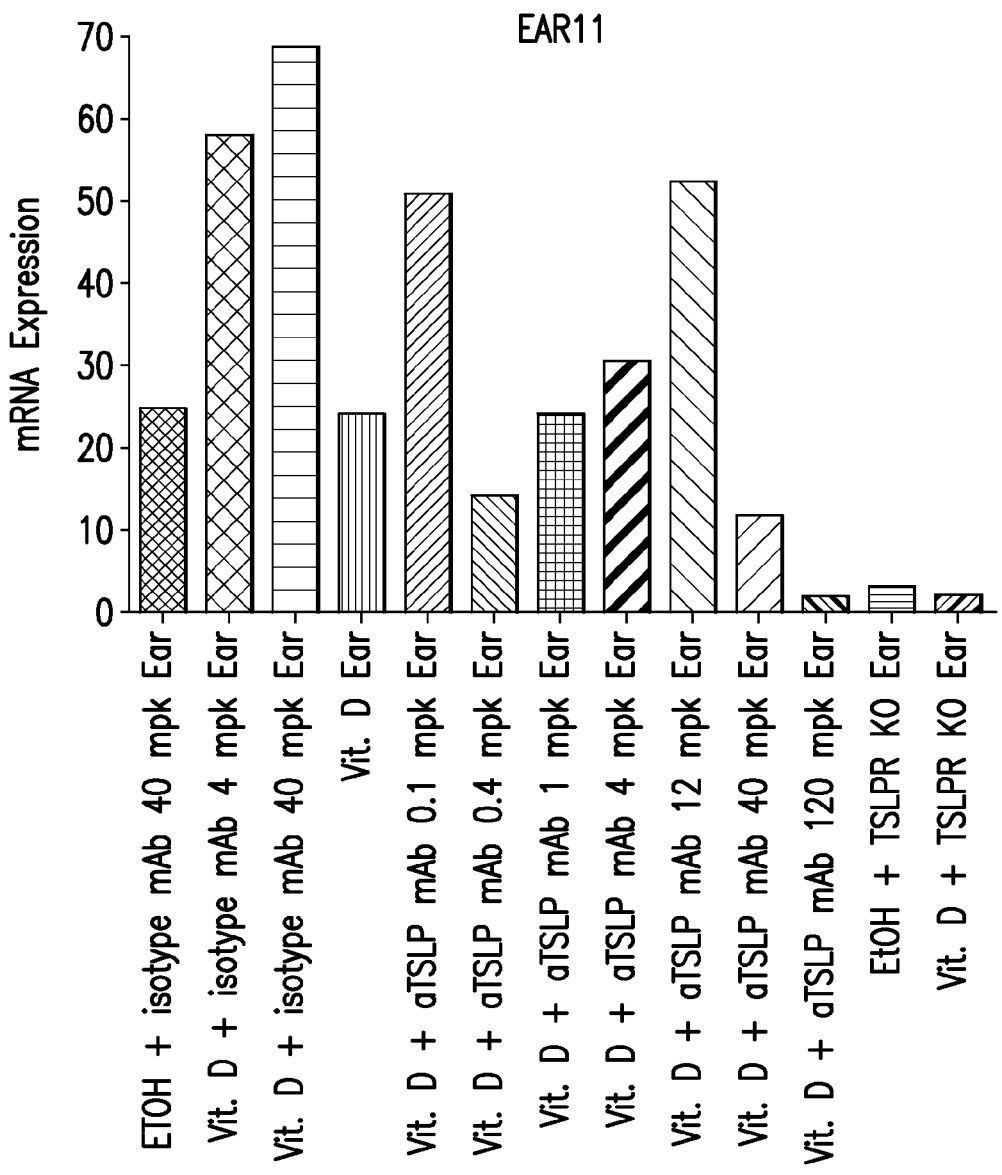
FIG. 5: Relative mRNA abundance of selected proteins EAR11(A), MMP-12 (B), LCN2(C), CHI3L3(D), CHI3L4 (E), CHI3L1(F), REG3G(G), PGYRP1(H), CD44(I) in calcipotriol treated mice. The mRNA expression was measured by real-time PCR in skin from mice treated with calcipotriol +/−anti-TSLP treatment.
Figure 5B:
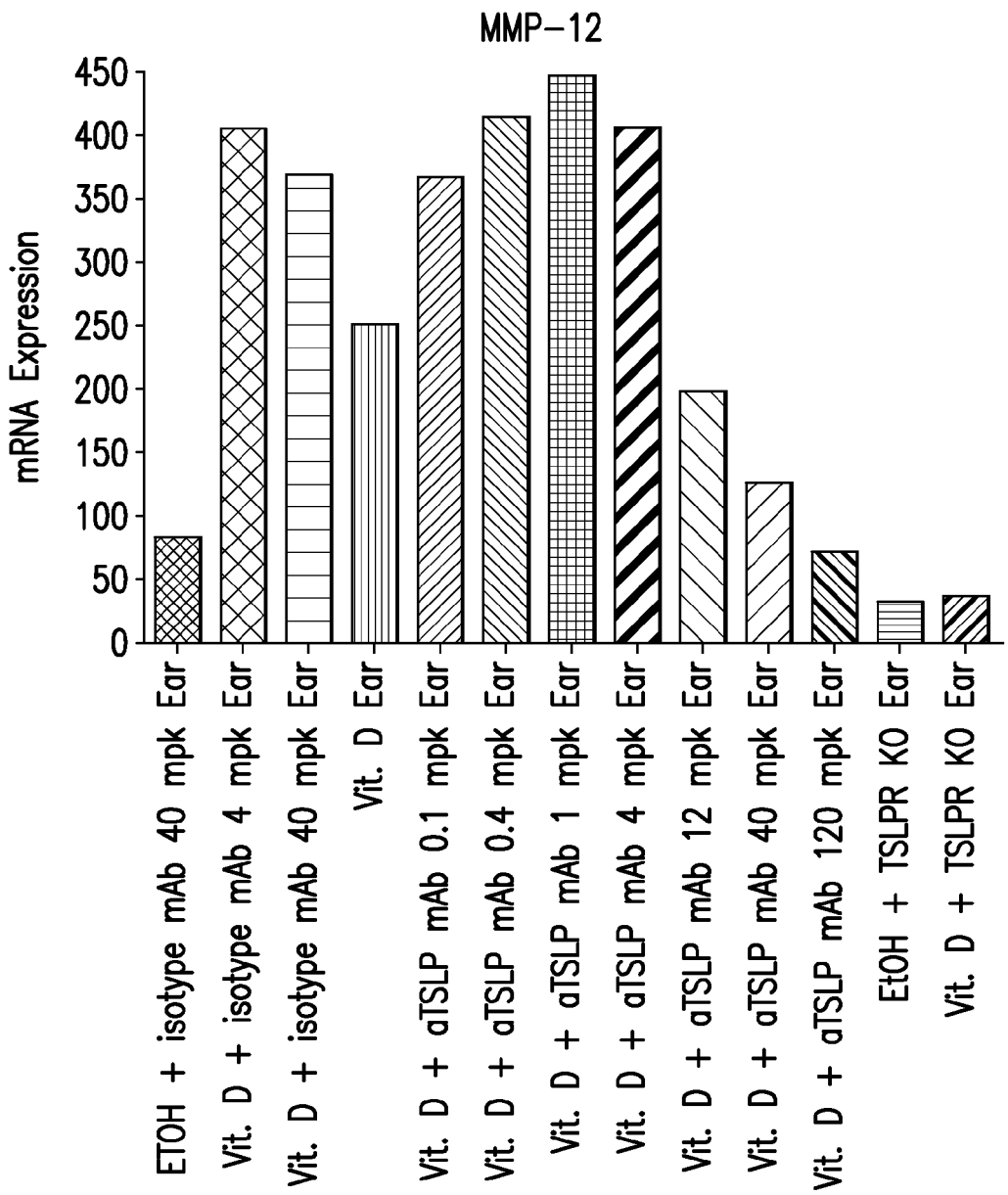
Figure 5C:
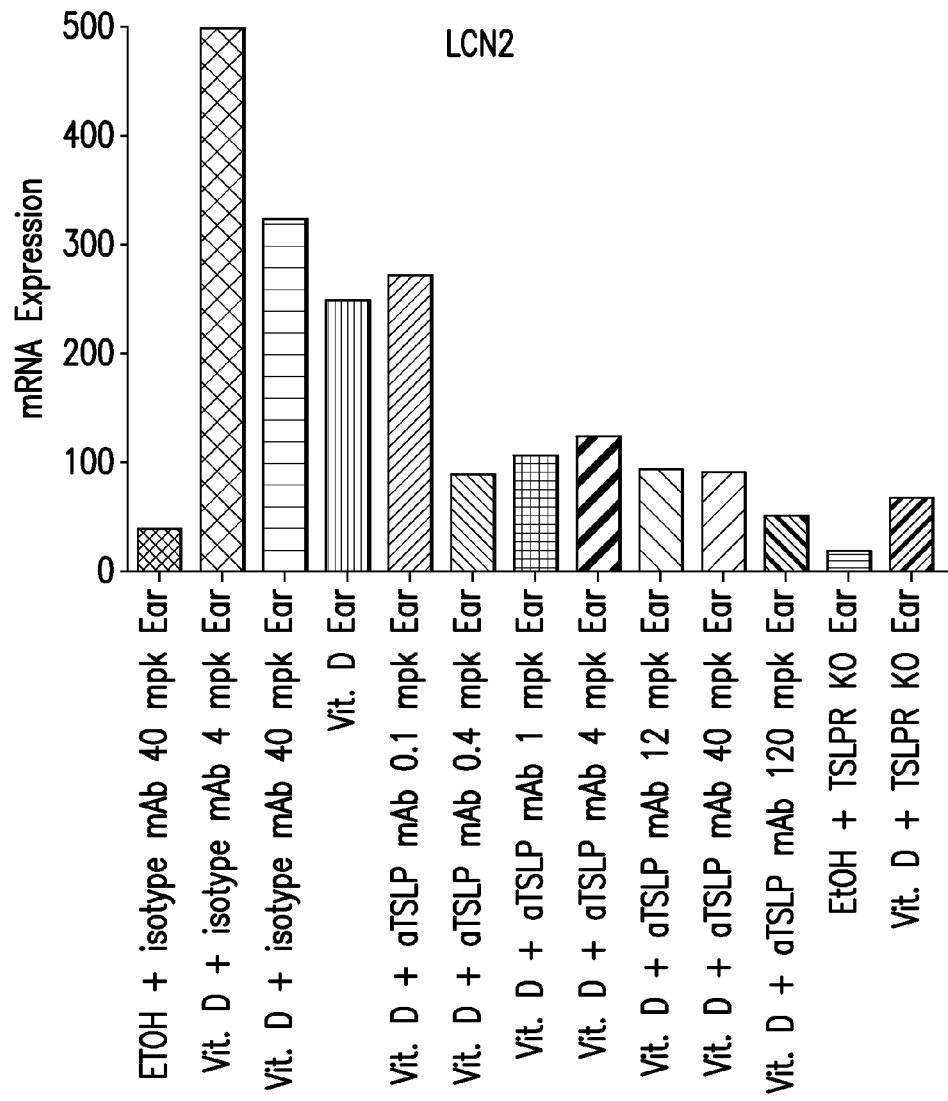
Figure 5D:
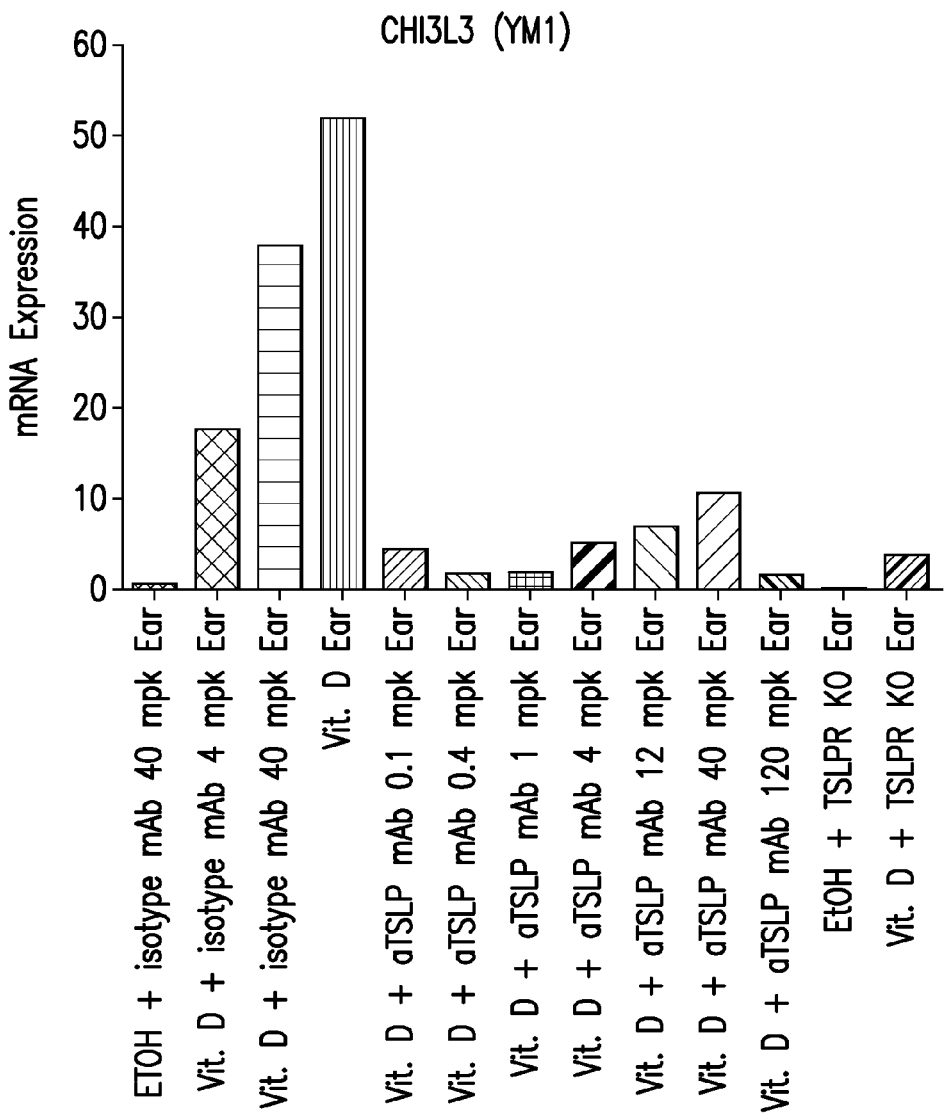
Figure 5E:
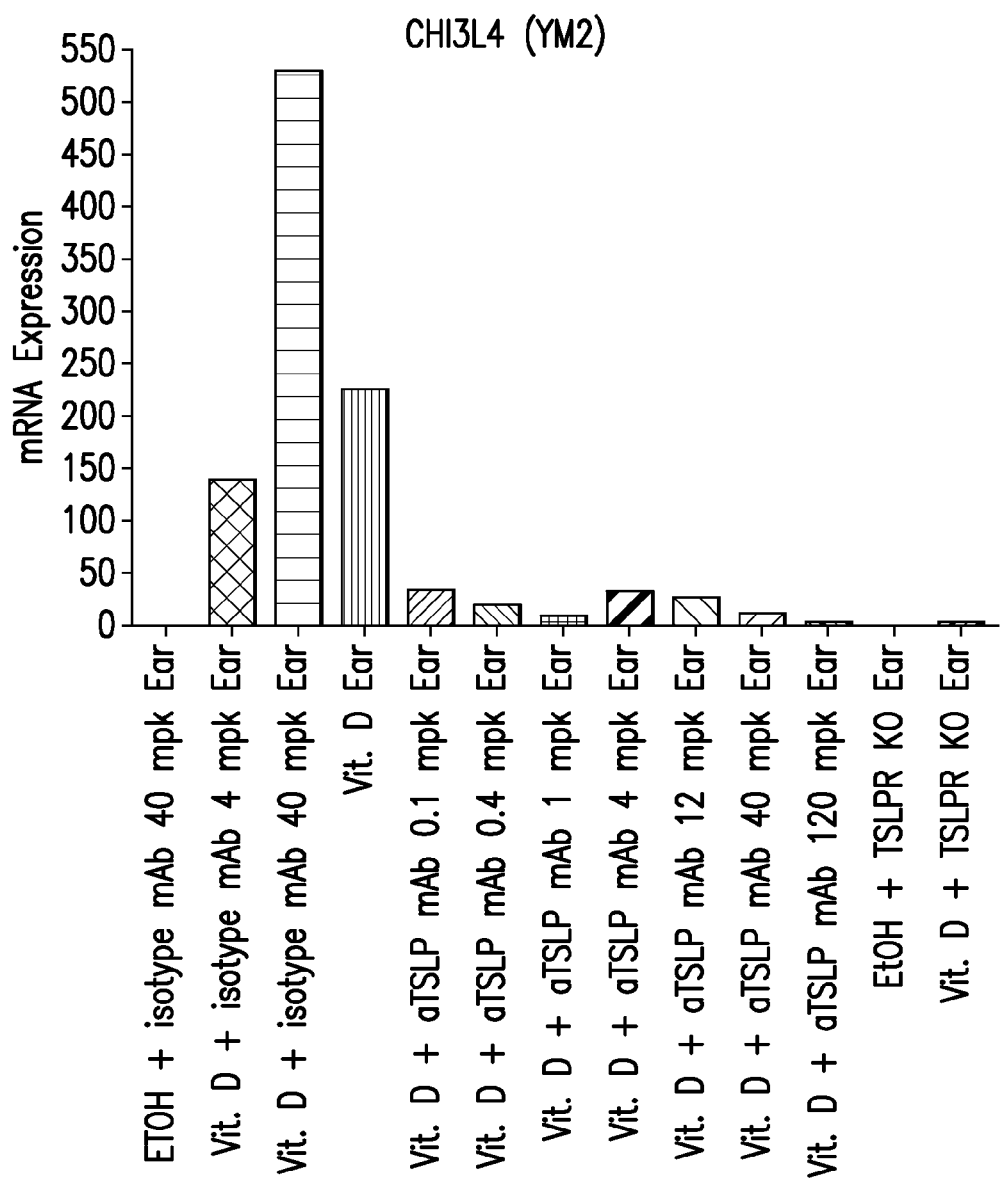
Figure 5F:
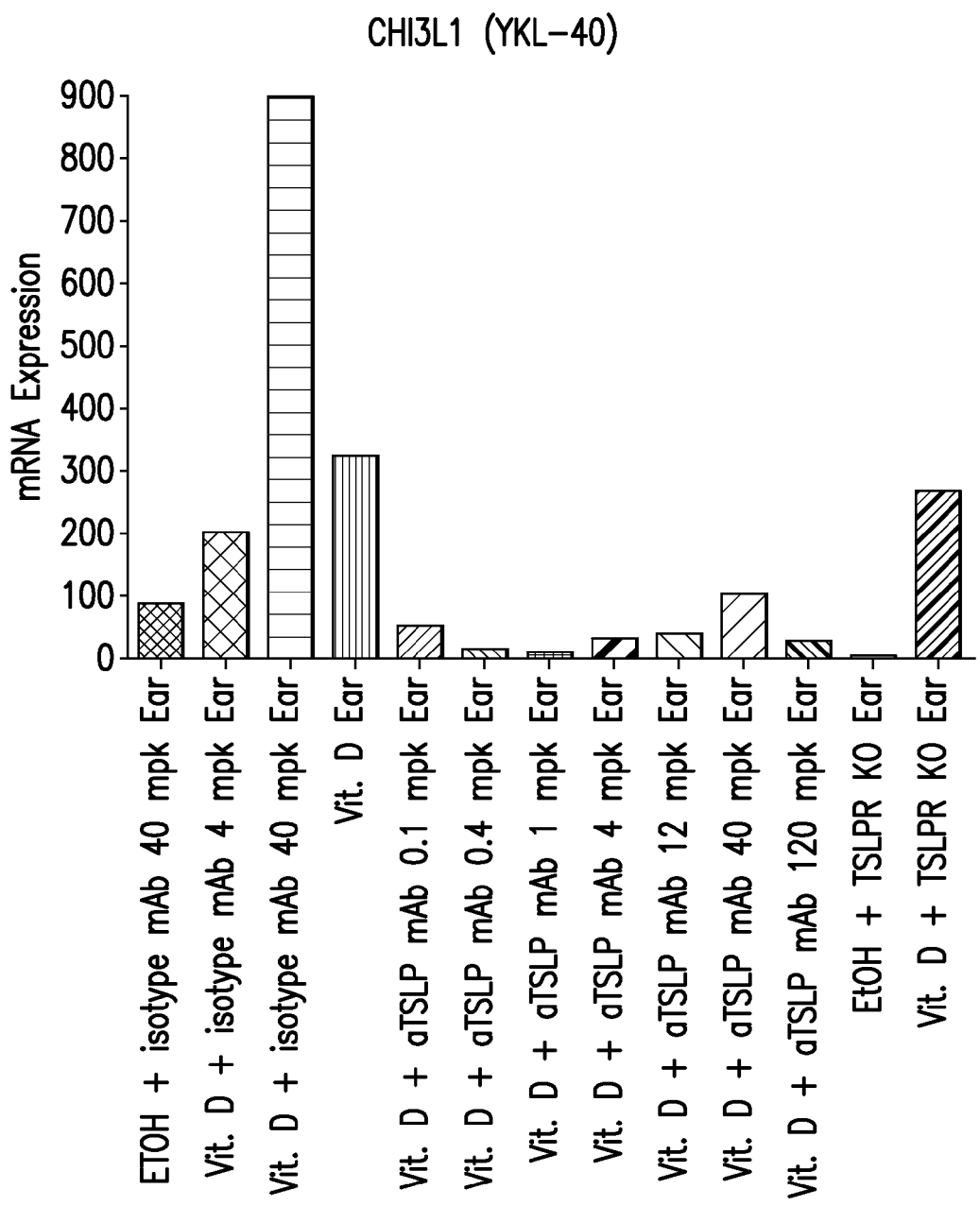
Figure 5G:
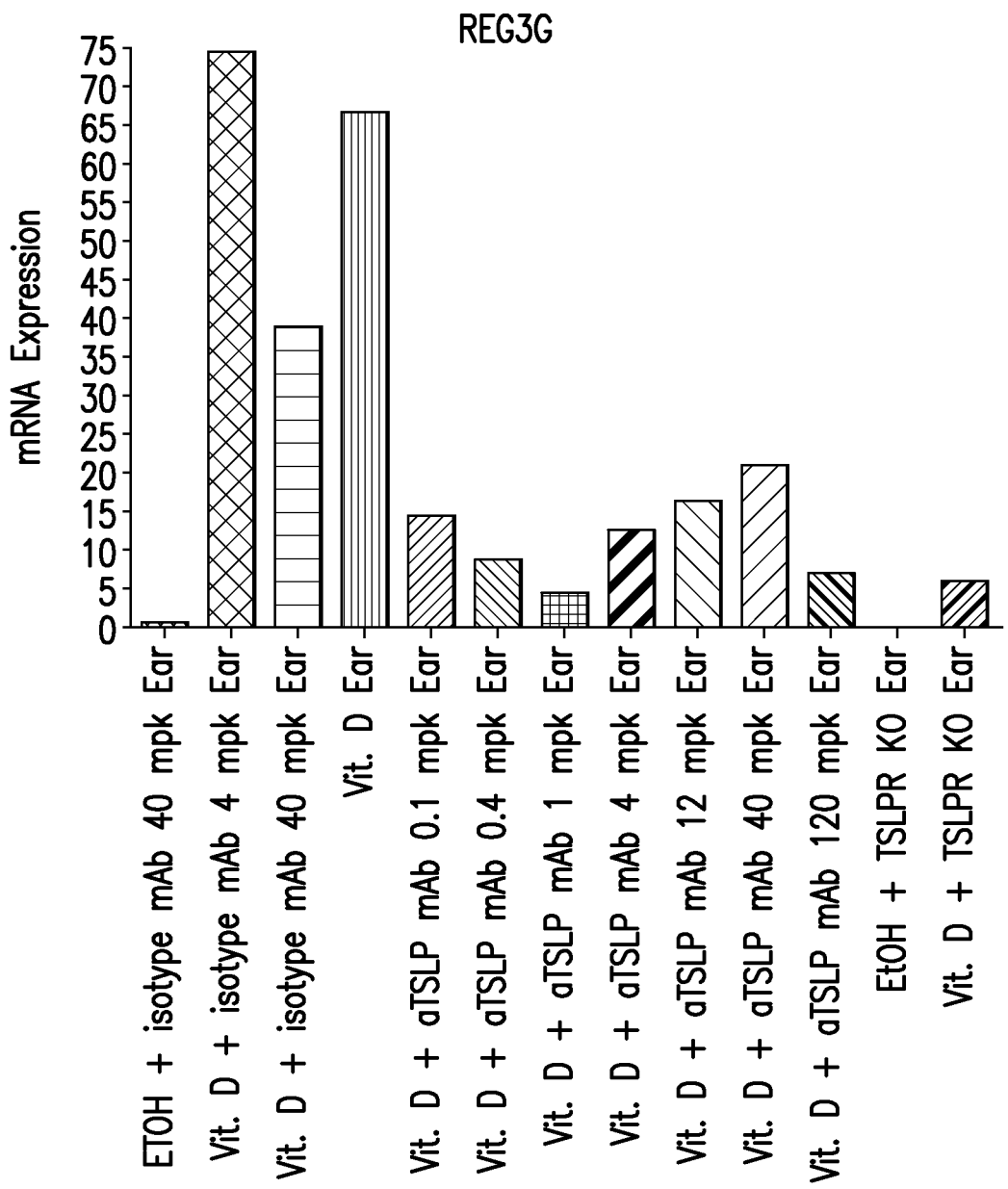
Figure 5H:
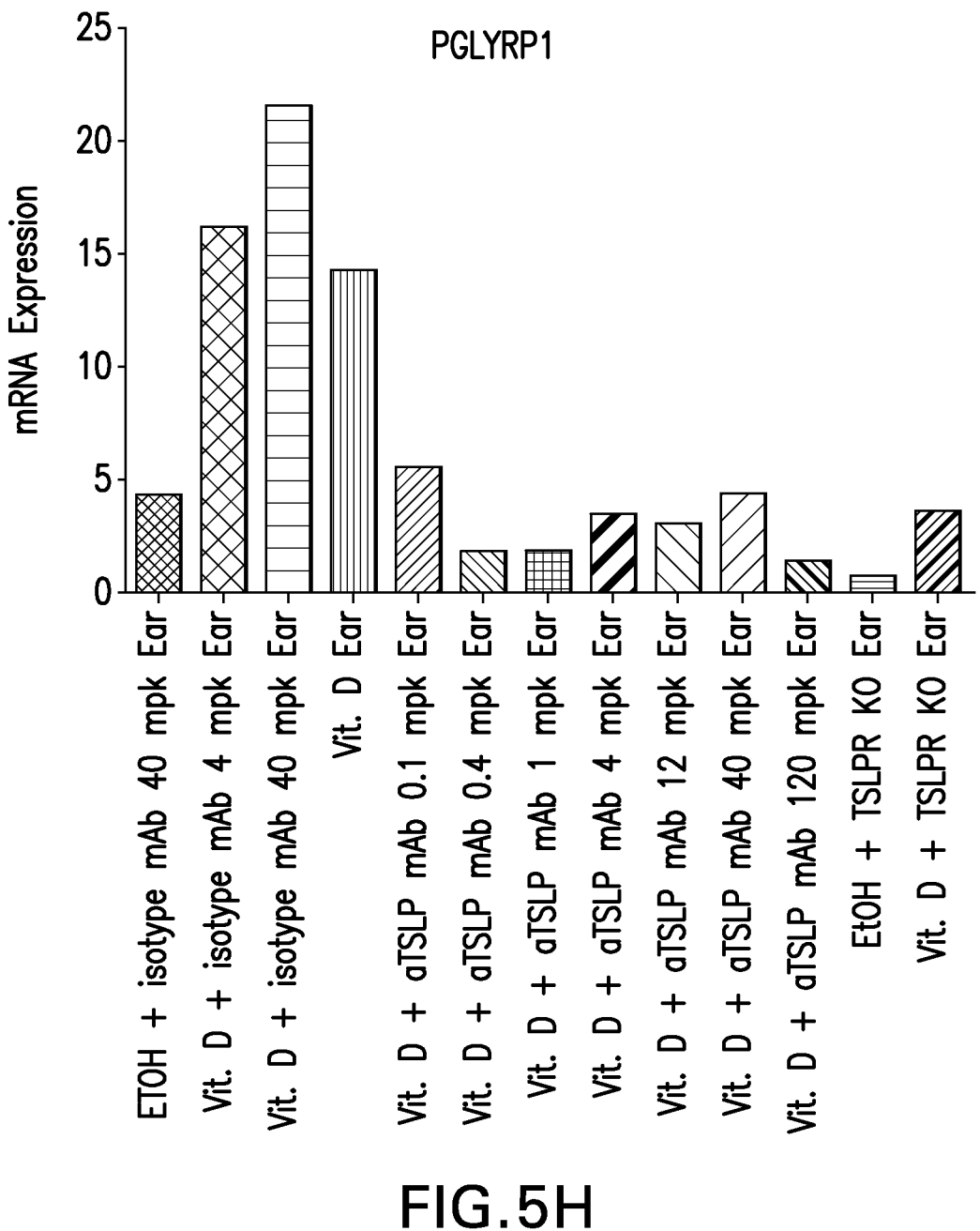
Figure 5I:
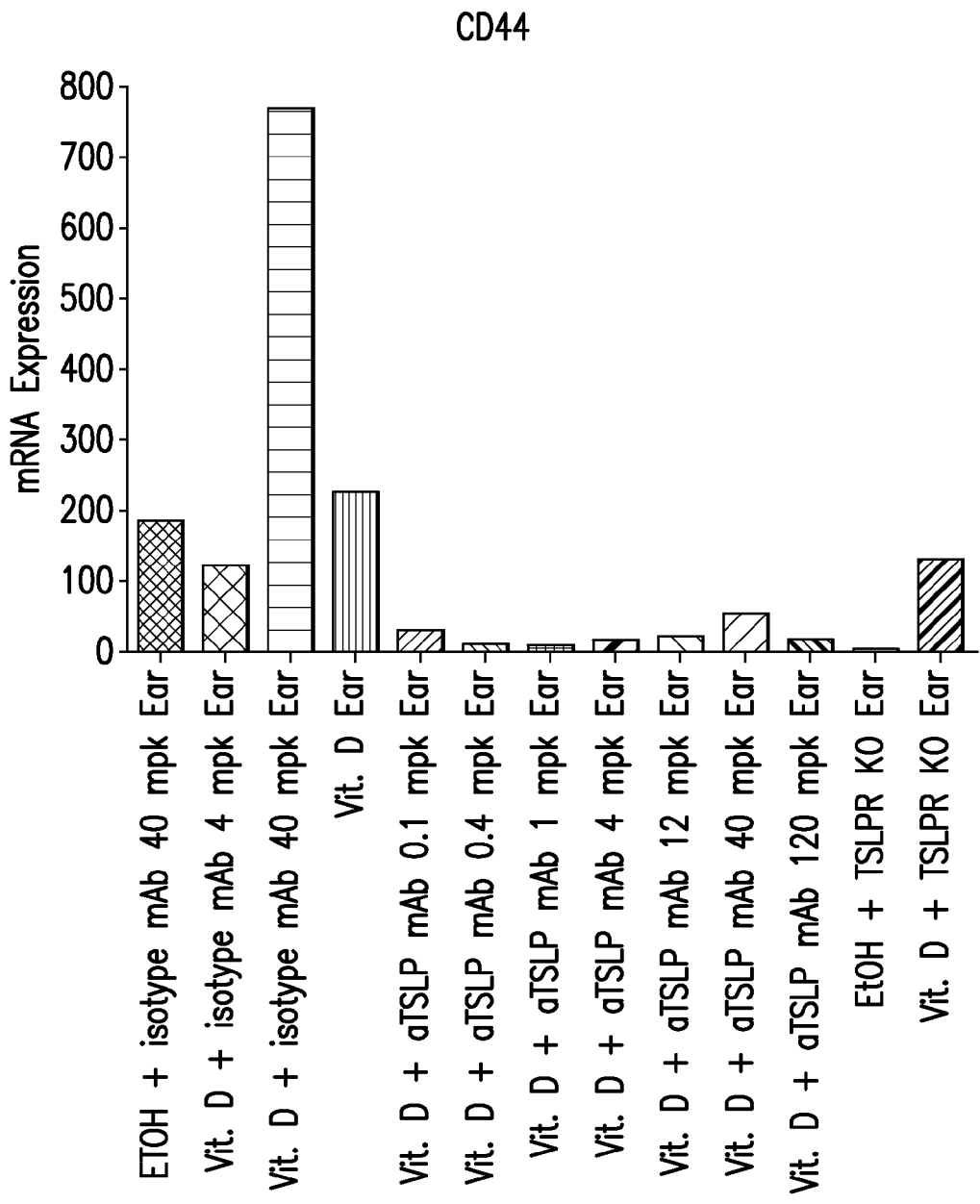
Figure 6A:
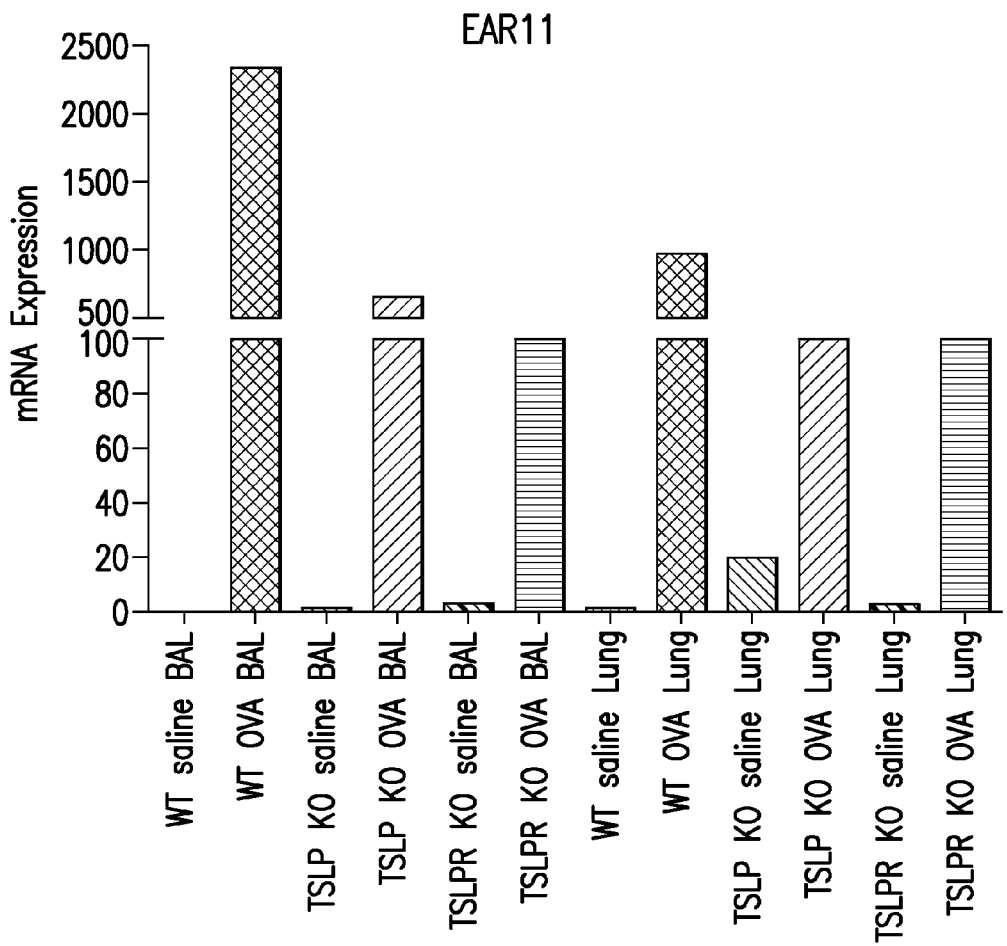
FIG. 6: Relative mRNA abundance of selected proteins EAR11(A), MMP-12(B), CHI3L1(C), YNL(D) in mice having OVA-induced asthma. The mRNA expression was measured by real-time PCR in lung and Bal cells from control mice, TSLP KO mice and TSLPR KO mice +/−challenge with OVA to induce lung inflammation.
Figure 6B:
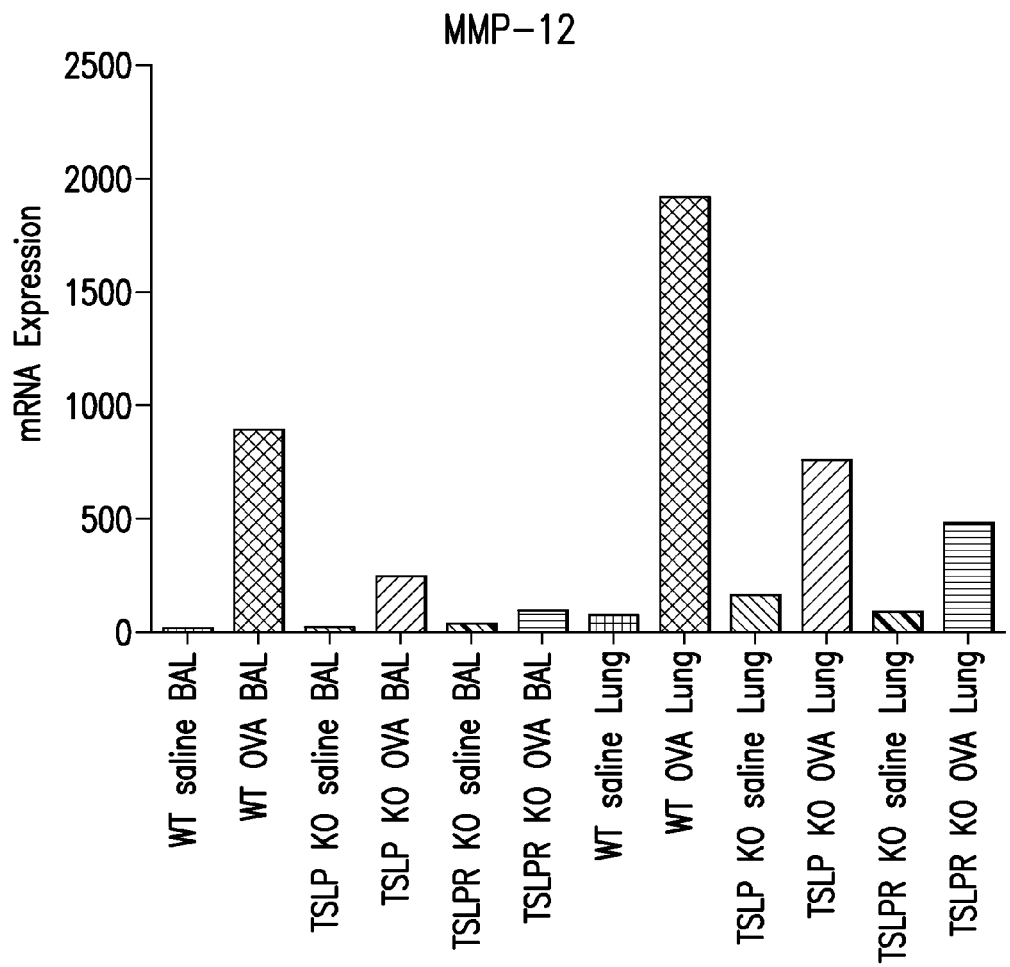
Figure 6C:
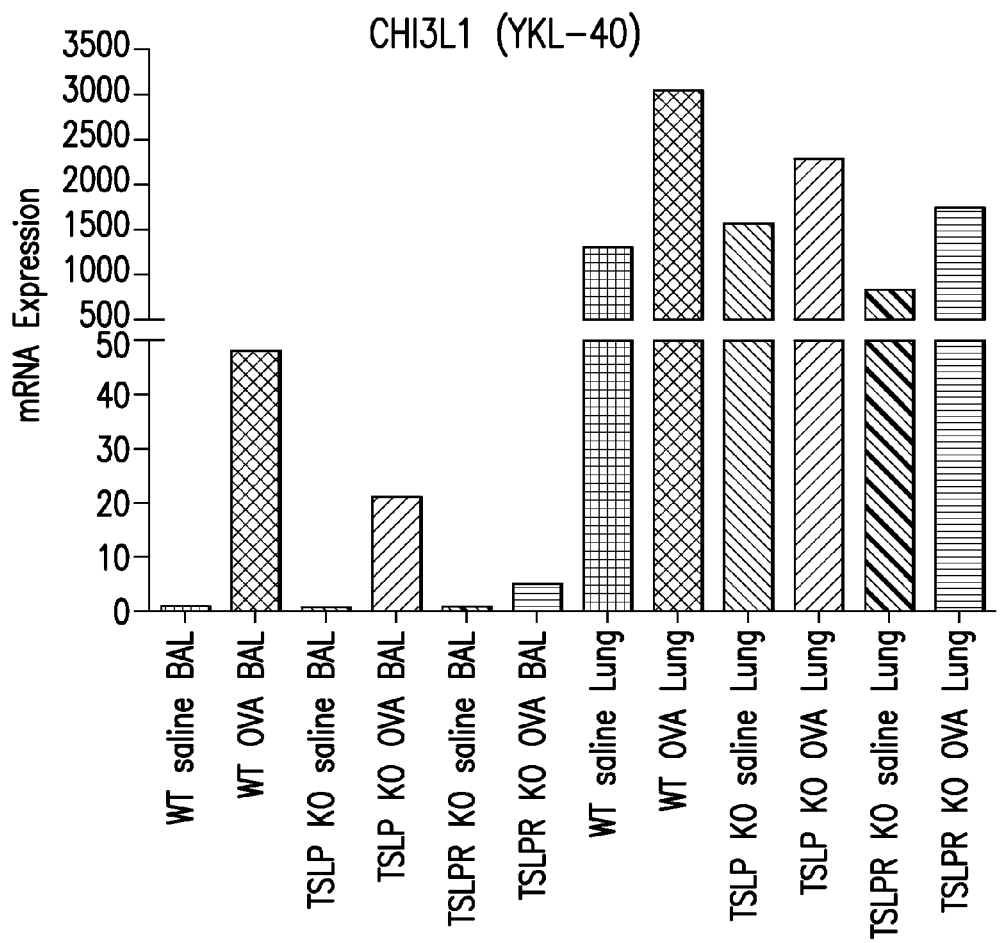
Figure 6D:
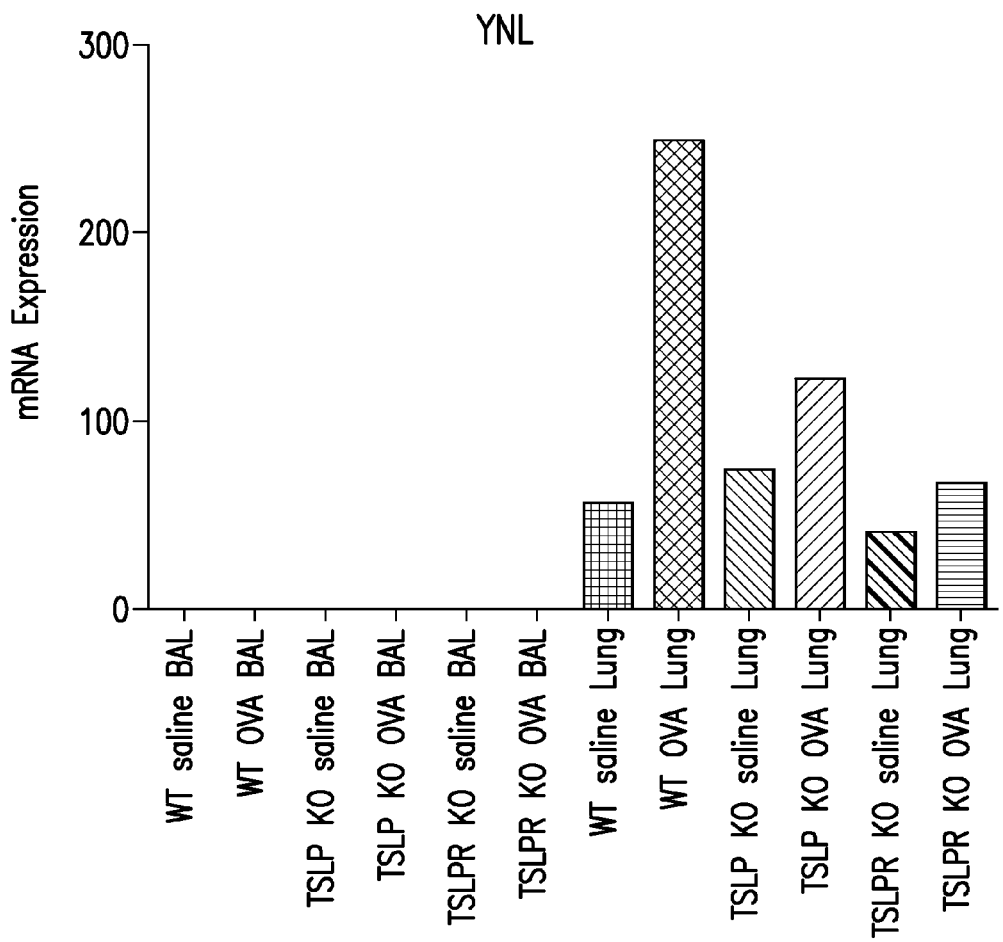
Figure 7B:
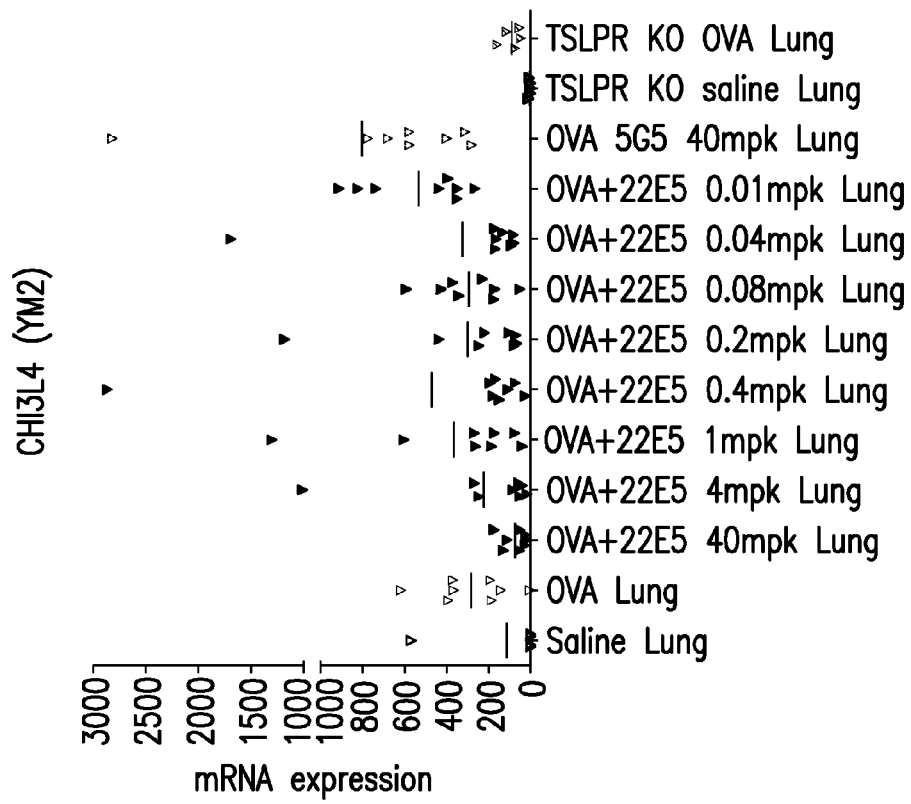
FIG. 7: Downregulation of biomarkers CHI3L3(A), CHI3L4(B), YNL(C), CHI3L1(D), RELMA(E), RELMB (F), EAR 11(G), MMP-12(H), REG3G(I), Tff2(J), CXCL12 (K), IL-19(L), LCN2(M), IL-25(N), IL-17RB(O), EPX(P), PRG2(Q), AIF1(R), PIGR(S) in mice treated with an anti-TSLP antibody.
Figure 7A:
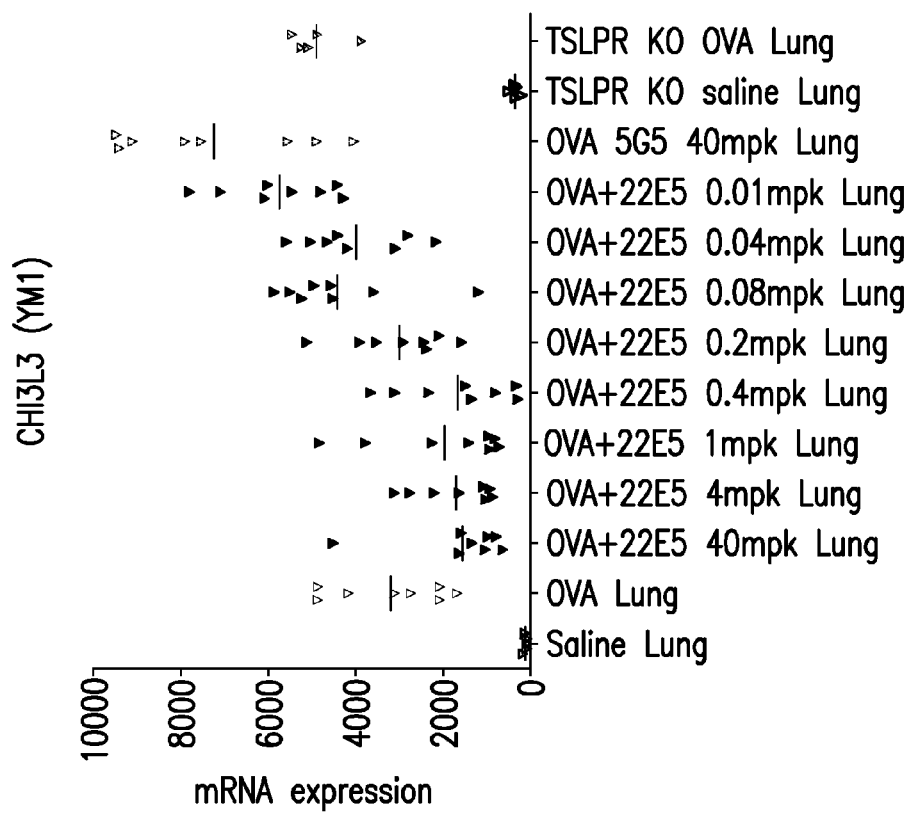
Figure 7D:
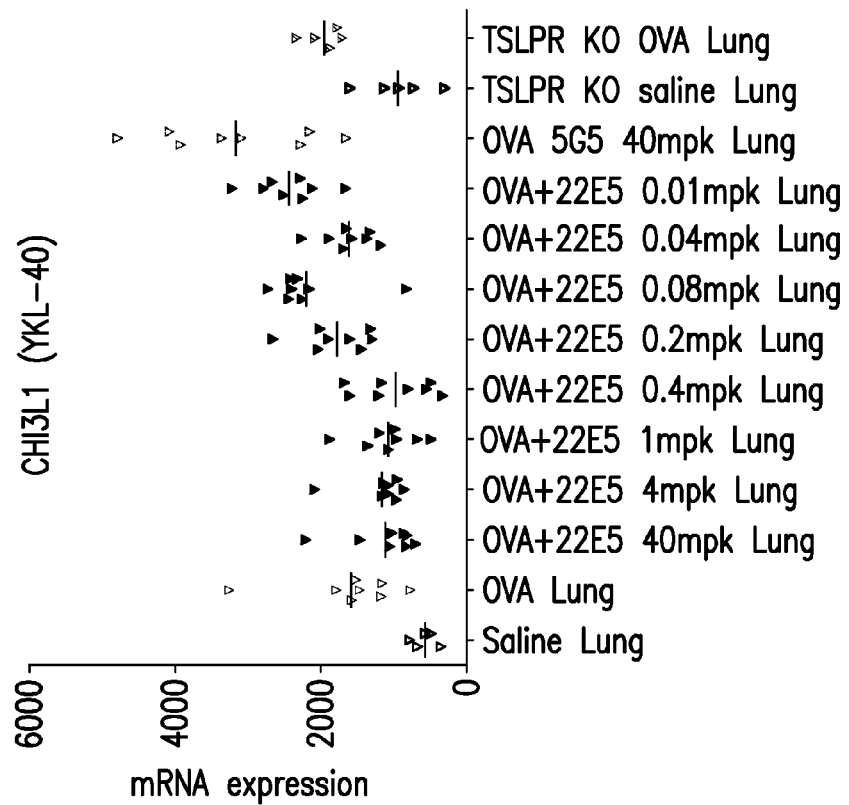
Figure 7C:
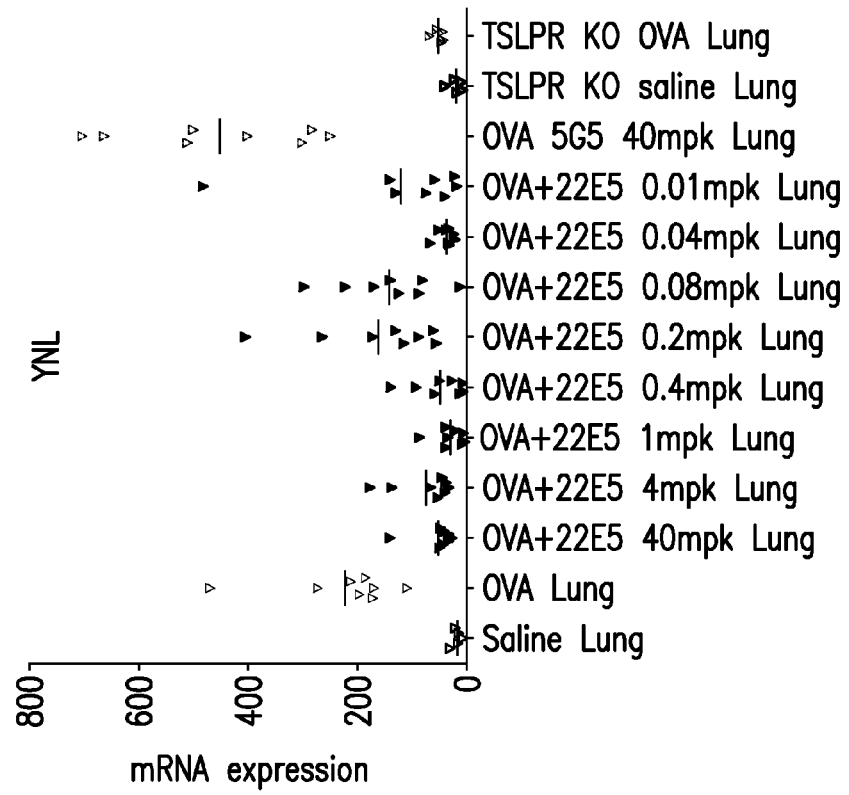
Figure 7F:
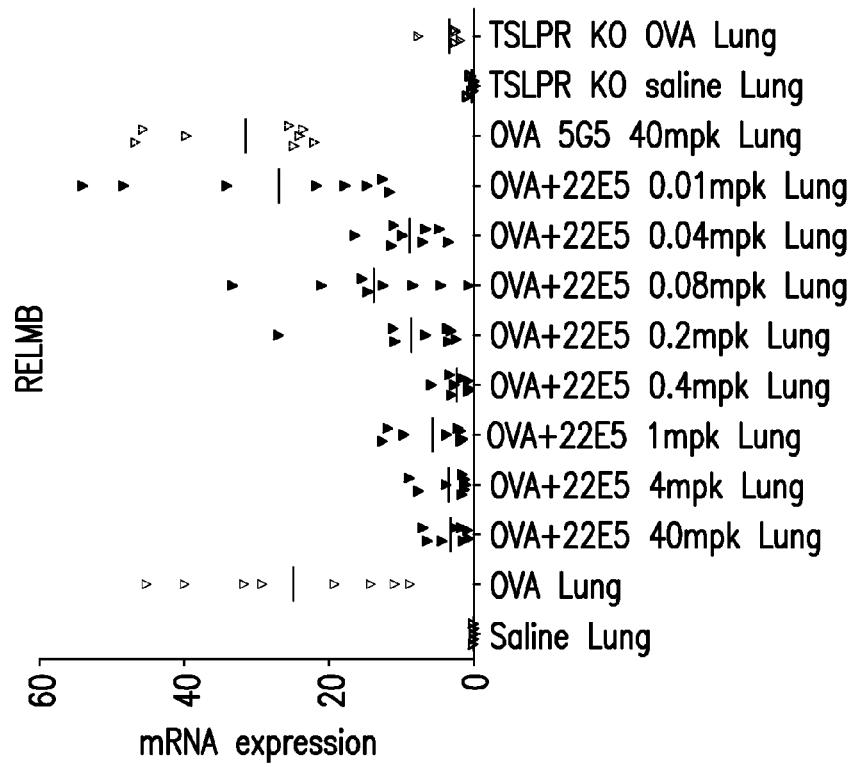
Figure 7E:
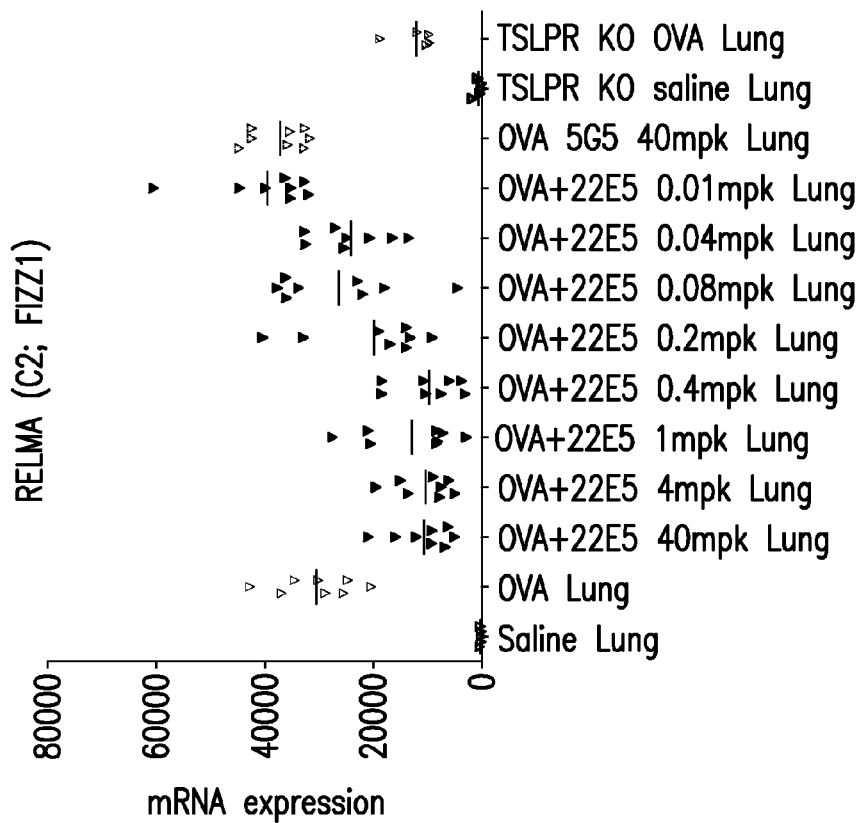
Figure 7H:
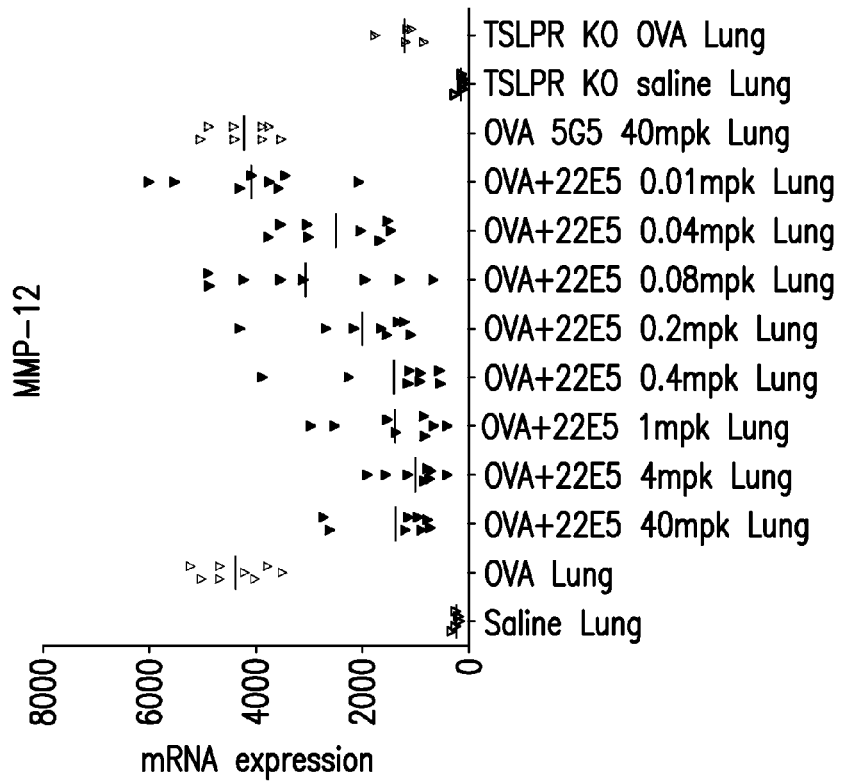
Figure 7G:
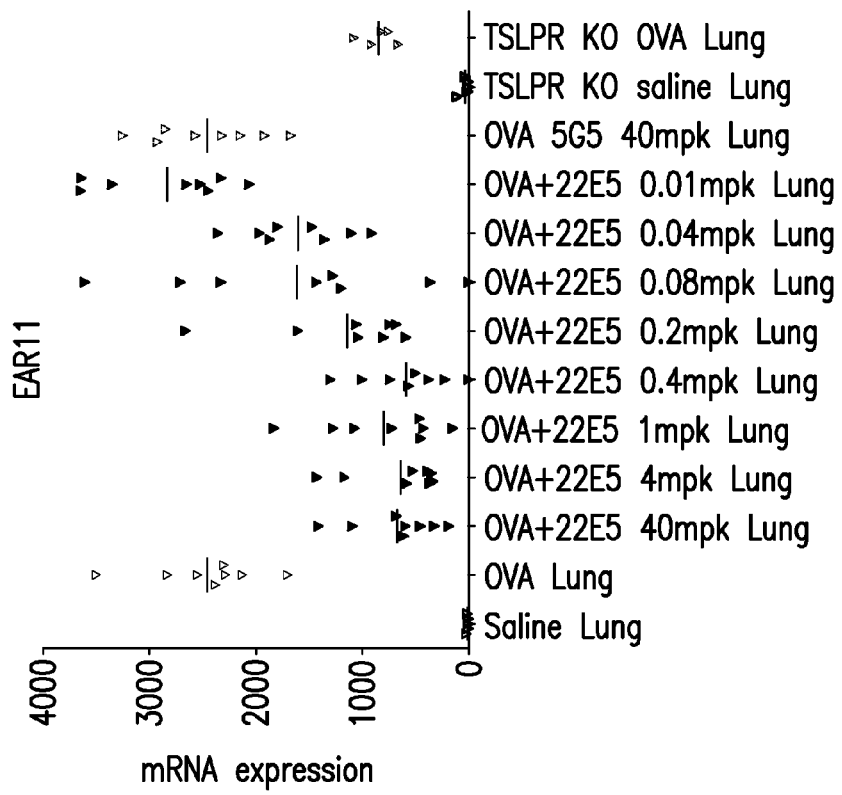
Figure 7J:
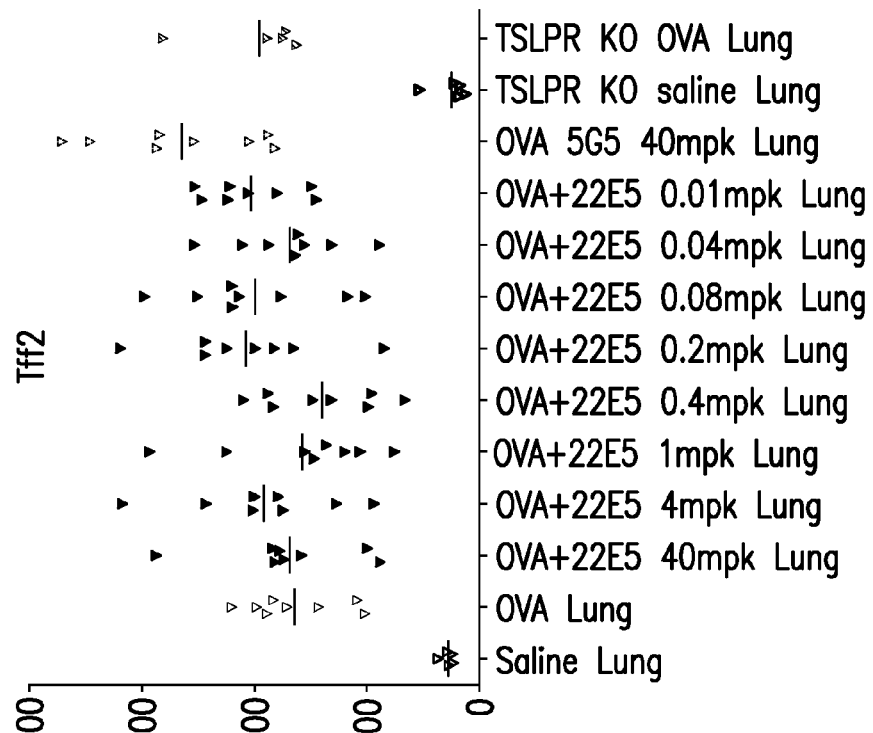
Figure 7I:
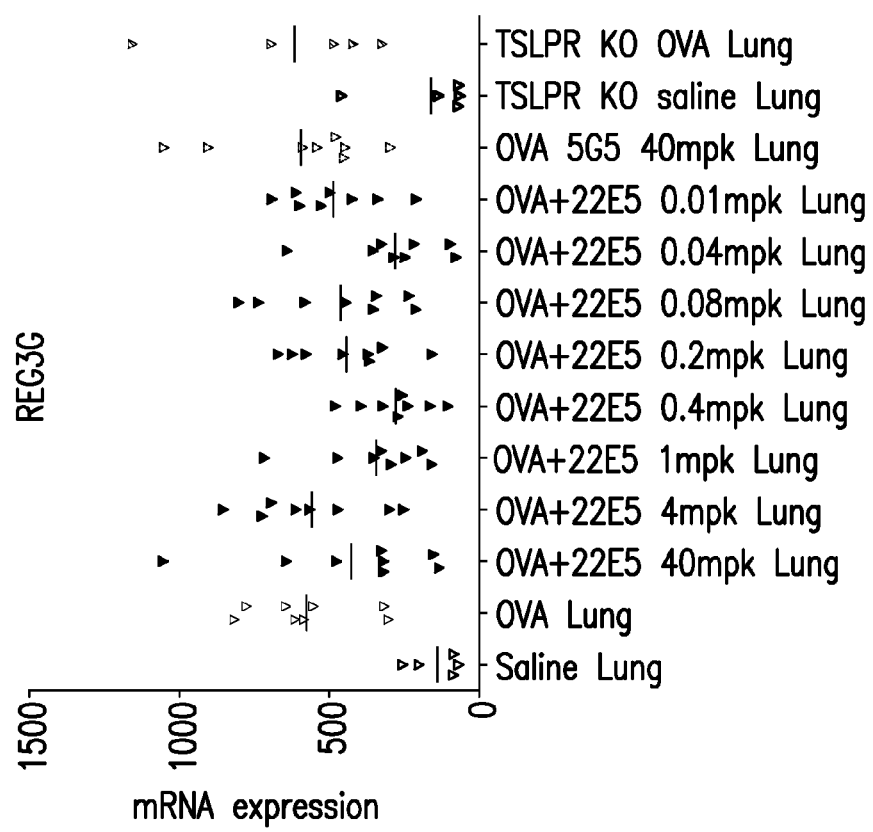
Figure 7K:
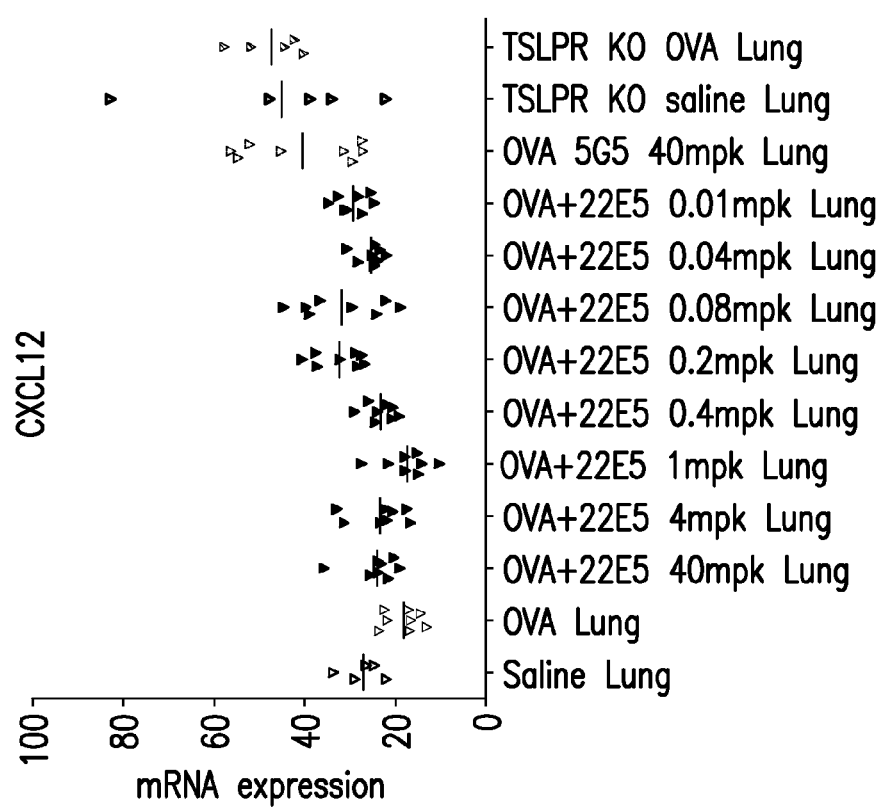
Figure 7M:
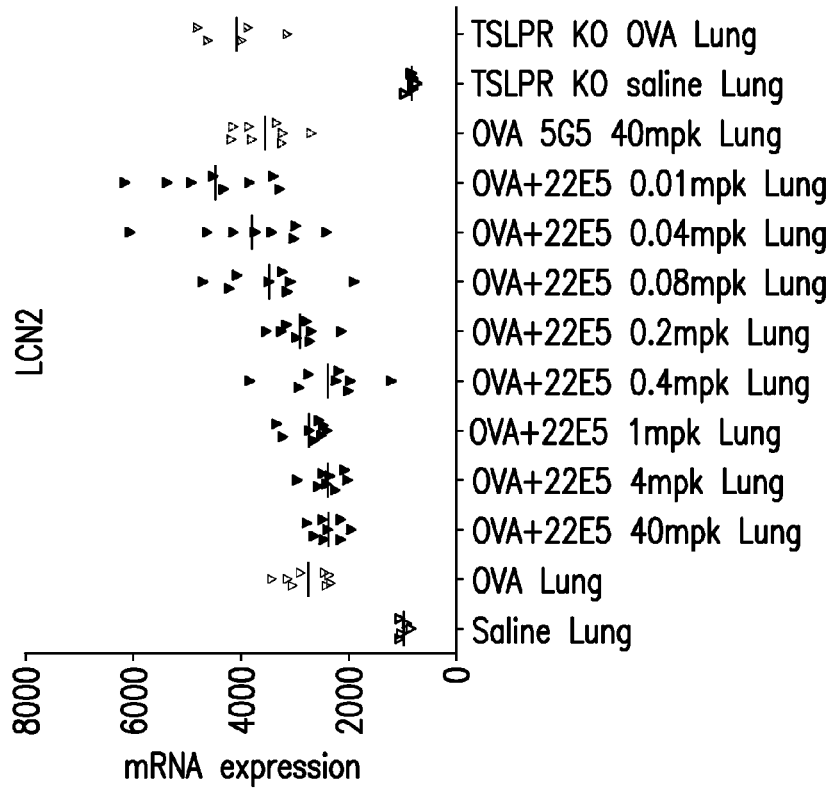
Figure 7L:
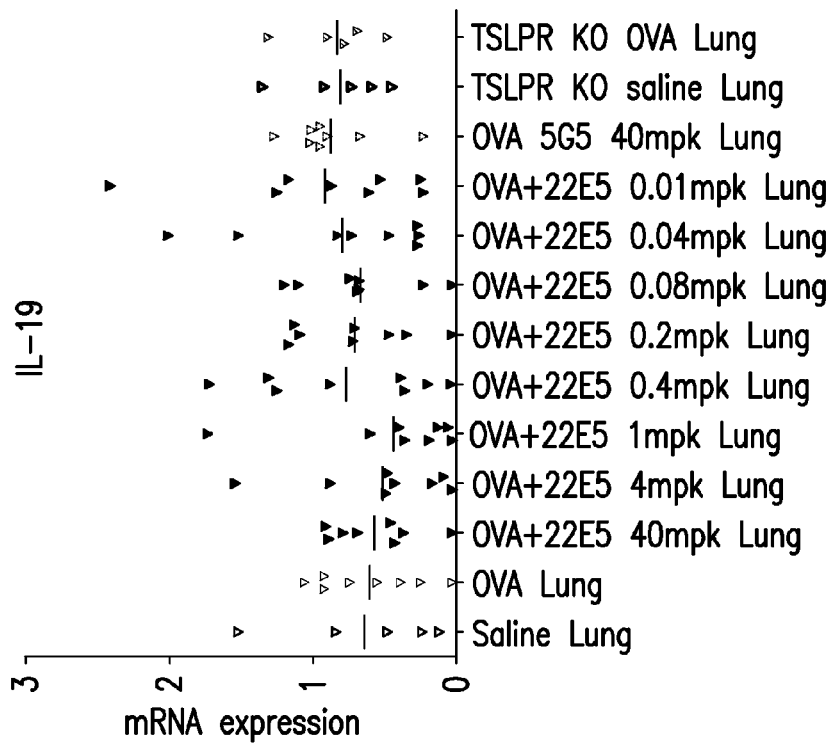
Figure 7O:
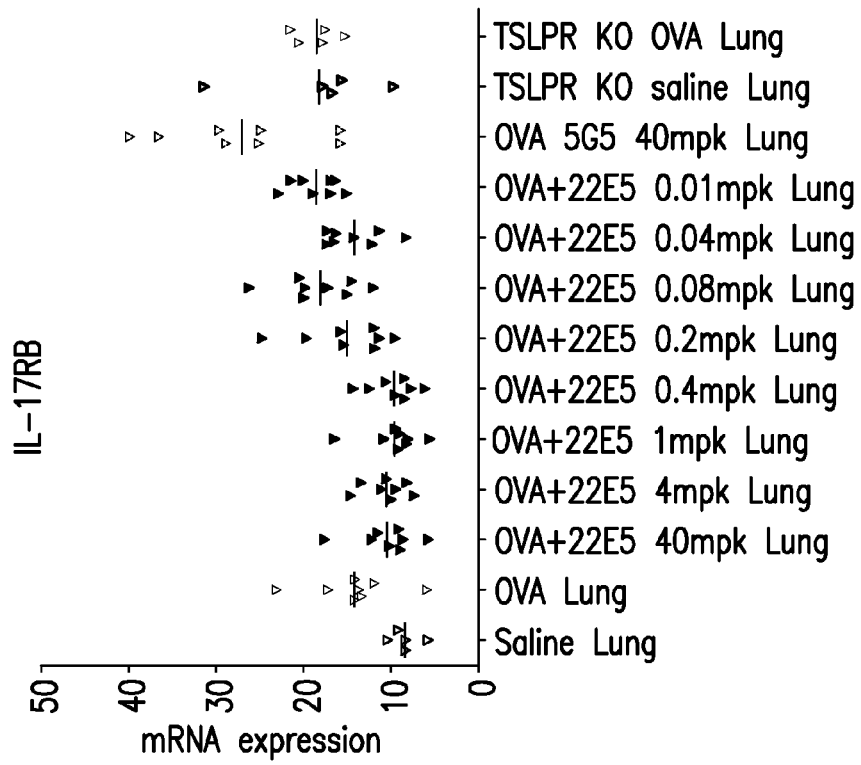
Figure 7N:
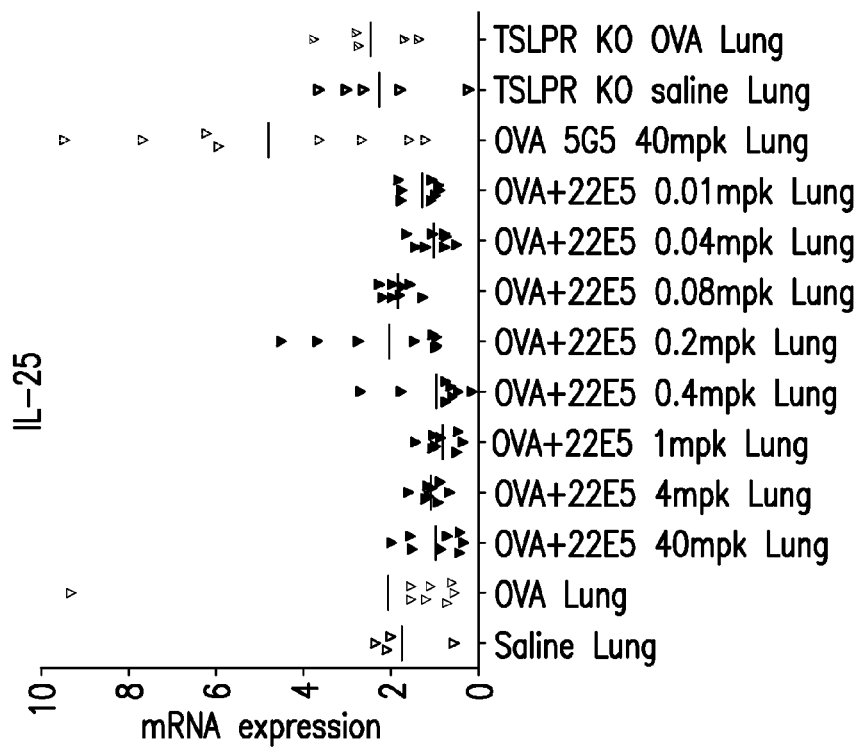
Figure 7Q:
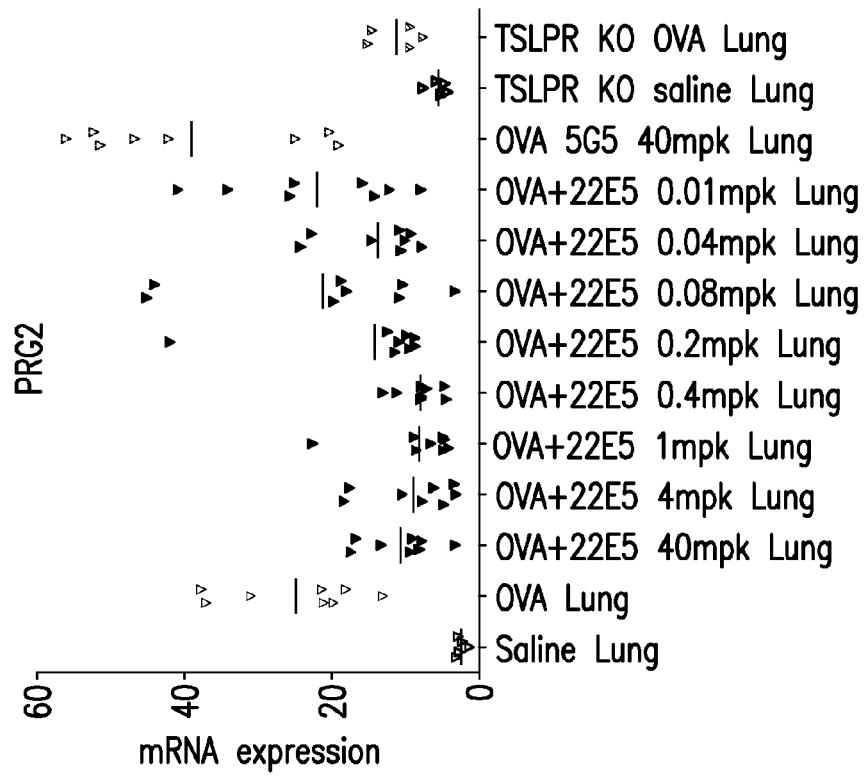
Figure 7P:
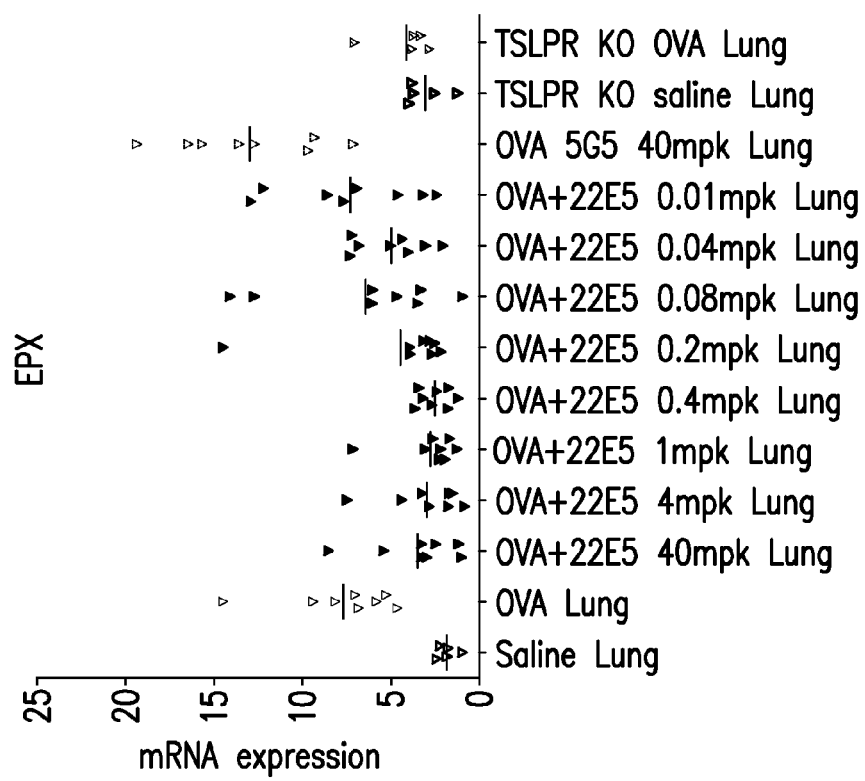
Figure 7S:
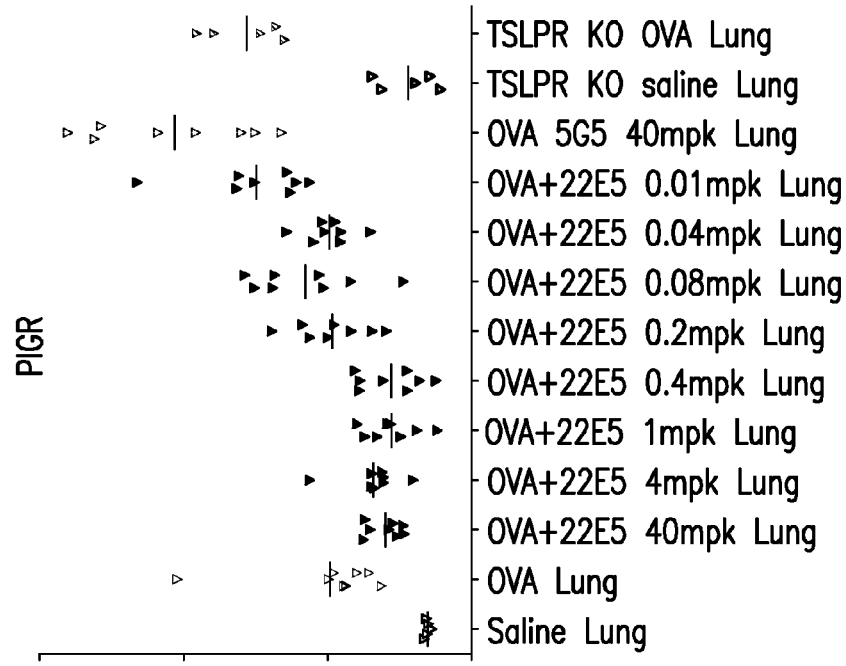
Figure 7R:
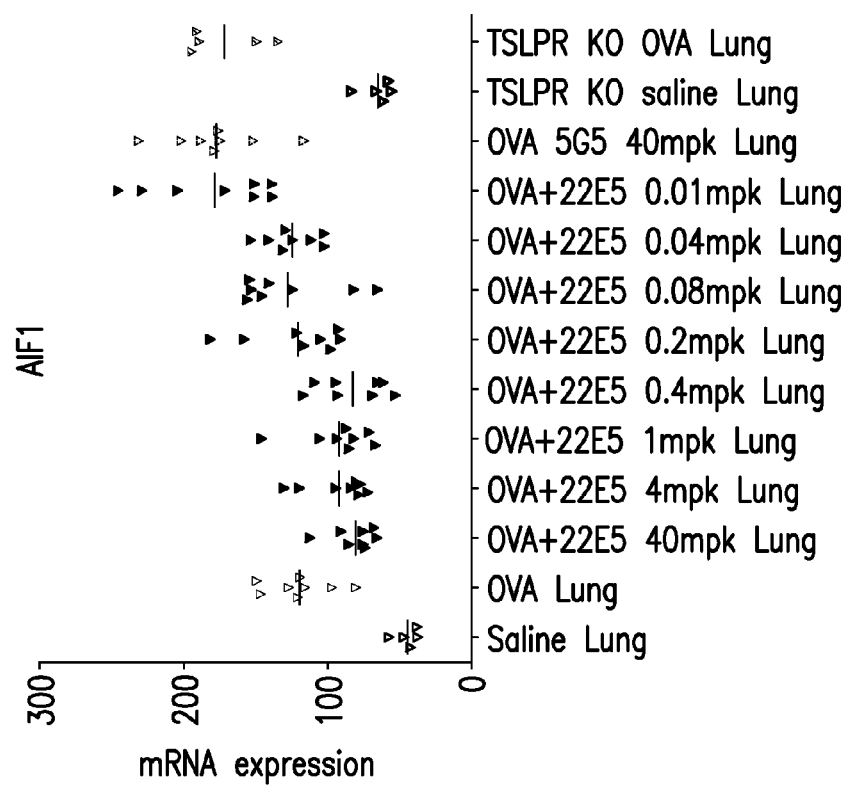

Representative western blot results are also shown. BAL fluid GP-39 was assayed via ELISA (FIG. 4B).

Results

Although several of the biomarkers we verified have been individually documented to be involved in human asthma, we sought to further validate our set of biomarkers in a model of chronic asthma closer to human disease. Towards this goal, we used a house dust mite allergen (HDMA)-induced asthma model in cynomolgus macaques (*Macaca fascicularis*). As previously described, HDMA-sensitized animals present with a Th2 phenotype characterized by airway eosinophilia, bronchial hyperresponsiveness, and goblet cell metaplasia. See Van Scott et al., *J. Appl. Physiol.* 2004; 96:1433-44. Mass spectrometry was performed on BAL fluid from HDMA-sensitized animals 24 hours before or 24 hours following challenge with HDMA. 70 identified proteins were upregulated in the BAL fluid of challenged cynomolgus monkeys (Table VII), eight of which were also identified in the BAL fluid of asthmatic TSLP Tg mice: apoH, CLCA1/3, Factor H, Fibronectin 1, FCGBP, LCN2, pIgR, and S100A9. Although not identical, several upregulated proteins were identified from similar families in monkey and mouse, such as cyclophilin A and cyclophilin B/C or serpin A1 and serpin B6, respectively. Importantly, one also has to bear in mind that several murine proteins are not expressed in higher mammals (e.g. lungkine, YM1, or YM2), and as less information is known at the protein level for *M. fascicularis* than for mouse or human, it is likely that monkey proteins with lesser homology to their human counterparts were not positively identified.

Although many reagents do not exist for the analysis of monkey proteins, antibodies have been made against several of the human orthologs of the murine biomarker proteins that exhibit cross-reactivity with cynomolgus proteins. YKL40 and PAP (the human ortholog of GP-39 and Reg3γ, respectively) (by ELISA) and AMCase, ICAM-1, LCN2, UG, pIgR, and CLCA1 (the human ortholog of murine CLCA3) (by western blot) were all present at very high amounts in the BAL fluid of HDMA-challenged animals (data not shown). As these results were consistent with the studies performed in TSLP Tg mice, we next examined which of these biomarkers were modulated with corticosteroid treatment. Towards this end, HDMA-challenged monkeys ("Pre," taken 24 hours after HDMA challenge) were treated with high-dose corticosteroids for 2 weeks, and BAL fluid was collected 24 hours following a final challenge with HDMA ("Post"). As expected, corticosteroid-treated animals exhibited reduced asthma symptoms characterized by improved lung function and reduced airway eosinophil recruitment (data not shown). Although trending downward, the expression of LCN2, UG, pIgR, PAP, and CLCA1 was not significantly reduced in BAL fluid following corticosteroid treatment (data not shown); however, AMCase, sICAM-1, CLCA1 (all by western blot) and GP-39 (by ELISA) were significantly reduced in corticosteroid-treated challenged animals (FIGS. 4A and B), similar to results obtained in dexamethasone-treated TSLP Tg mice (see FIGS. 3A and B). Taken together, these results indicate that the disease and treatment biomarkers characterized in TSLP Tg mice are also modulated in higher-order primate species.

Table VII: List of proteins identified by mass spectrometry in BAL fluid from HDMA-sensitized cynomolgus monkeys before or after challenge with HDMA. Proteins were classified as being upregulated (VIIA), similarly expressed (VIIB), or downregulated (VIIC) in the BAL fluid of HDMA-challenged animals, compared to HDMA-sensitized, unchallenged animals.

TABLE VII

| Protein | NCBI GI Protein Accession Number |
|---|---|
| A | |
| 14-3-3 beta | 3065925, 4507949, 90076742, 1585294 |
| alcohol dehydrogenase | 114595327 |
| ALDH1A1 | 2183299, 21361176 |
| ALDH3A2 | 124004853, 1666529 |
| alpha-1-microglobulin/bikunin precursor | 579676 |
| apoA1 | 109108768, 178775, 23379764, 23379768, 2914175, 342075, 3915607, 4557321, 73955106 |
| apoA4 | 109108832, 28762, 461521 |
| ApoH | 109116937, 109116939, 11513724, 28810, 543826 |
| C2 | 34628, 14550407 |
| C8 | 109109736, 21730336 |
| C9 | 179726, 2258128 |
| Calcyphosine | 4757908 |
| Calmodulin | 4502549, 640285, 71664 |
| Carbonic anhydrase 1 | 109086845, 4502517, 461679, 515084 |
| carbonic anhydrase 2 | 30466252 |
| Carbonyl reductase 1 | 51830180 |
| Charcot-Leyden crystal protein | 109124714 |
| CLCA1 | 114557513 |
| Clusterin | 32891795, 55846712, 90077304 |
| coagulation factor II | 109106394 |
| cofilin 1 | 5031635, 90075040 |
| copper containing amine oxidase 3 | 109115435, 4502119 |
| cyclophilin A | 114634944, 118098, 13937981, 1431788 |
| cystatin B | 4503117, 109065176 |
| cystatin C | 192912, 74136407 |
| DC48 | 12006209 |
| dopachrome tautomerase | 109094852, 4503291 |
| factor H | 109018998, 109019002, 4504375 |
| factor I | 116133, 182607, 67967767 |
| Fc Gamma BP | 109124740, 4503681, 5080756, 109124740 |
| fibronectin 1 | 109100908, 126337927, 1421281, 149710153, 30722344, 31397, 34364617 |
| GAPDH | 31645, 37730278, 41147378, 7669492 |
| Gelsolin | 109110365, 4504165 |
| GSTm5 | 37748321 |
| Haptoglobin | 109129090, 1212947, 34785974, 466455 |
| haptoglobin-related protein (HPR) | 123510 |
| HLA-E single chain trimer | 33637489 |
| HRG | 109042262, 4504489 |
| HSP90 | 18605741, 55730837 |
| IGF binding protein | 109127203, 2498123, 4826772 |
| IgK-rh | 4105843 |
| ITIH1 subunit 3 | 2851501, 33989 |
| ITIH2 | 109088171, 125000 |
| ITIH4 | 1082547, 109039135, 7770149 |
| Kininogen | 4504893, 386852 |
| lactate dehydrogenase B | 4557032 |
| leukocyte protease inhibitor | 109091820, 4507065 |
| lipocalin 2 | 109112565, 55632379, 631308 |
| lysozyme C | 126608, 229157, 229916, 2497771, 48298997, 67408 |
| mannose BP A | 1449042 |
| NPC2 | 5453678, 62896507 |
| NUDC | 5729953 |
| ovostatin 2 | 109095618 |
| Peroxiredoxin 5 | 6166493, 6912238, 90078122 |
| Peroxiredoxin 6 | 109019544, 3219774, 3318841 |
| phosphoglycerate mutase 1 | 4505753 |
| PIGR | 109018572, 31377806 |
| Prosaposin | 1565529 |
| prostaglandin D synthase | 190444 |
| proteasome subunit 7 | 12314029 |
| retinol BP | 73998292 |
| S100A9 | 109016333, 4506773 |
| S100P | 114593120 |

TABLE VII-continued

| Protein | NCBI GI Protein Accession Number |
|---|---|
| SAP | 109017517 |
| selenium BP1 | 16306550, 73981582 |
| serpinA1 | 6855601, 28637 |
| sex hormone-binding globulin | 67969615 |
| SH3 domain binding glutamic acid-rich protein like | 4506925 |
| SOD3 | 4507151 |
| tetranectin | 267108, 4507557 |
| Transketolase | 12018252, 1729977, 31417921, 346399 |
| triosephosphate isomerase 1 | 136062, 16877874, 41058276, 4507645, 515257 |
| tubulin polymerization-promoting protein | 13385968 |
| UBA-52 (TI-225) | 13786827, 2627129, 4506713 |
| ubiquitin-conjugating enzyme E2 | 1066080 |
| Uteroglobin-related protein 2 precursor | 109080162 |
| X-prolyl aminopeptidase 3-like | 46309521 |

B

| Protein | NCBI GI Protein Accession Number |
|---|---|
| 14-3-3 zeta | 109087133, 114621209, 30354619, 4507953, 71897035 |
| A2M | 112911, 1304084, 157954061, 4557225, 73997689, 75054706 |
| Actin | 1070613, 113218, 113307, 139001520, 148806547, 32186898, 3219772, 47551039, 49868, 55732773, 58258865, 61676567, 71611, 7546413, 90811719, 14278147 |
| actin beta | 14250401, 15825662, 28336, 5107933, 6716561, 71625, 71629 |
| Afamin | 109074517, 114594313, 27229290, 4501987 |
| ALDH3A1 | 109113630, 126314265, 178375, 33871063, 399365 |
| alpha globin | 109129589, 122366, 122407, 122427, 13195586, 22671717, 319896, 75914658 |
| alpha-1-B glycoprotein | 109126335, 114679419, 23503038, 69990 |
| alpha-2 HS glycoprotein | 2116653, 109042277 |
| angiotensinogen | 109020030, 90075392, 4557287, 532198 |
| annexinA1 | 109111790, 113942, 148229927, 4502101, 73946797 |
| beta globin | 1066765, 13273496, 13549112, 1431650, 183857, 223012, 22874, 229149, 29446, 40886941, 4929993, 66473265, 86611 |
| beta-2 microglobulin | 34616, 547299 |
| C3 | 109123141, 114674922, 116597, 125804742, 179665, 284052, 40786791, 4557385, 544053, 557597, 78101267, 78101268 |
| C4a or b | 13936421, 24987346, 4063691, 40737319, 40737466, 40737478, 40737486, 4502501 |
| C5 | 109110418 |
| Ceruloplasmin | 109048806, 110347564, 126031006, 126338232, 126338232, 149408772, 149729967, 1620909, 180249, 1942284, 2493322, 42658910, 6970046 |
| CRB1 | 41327708, 6912322, 34364816 |
| factor B | 109070536, 291922, 4502397, 7145102, 758090 |
| factor D | 109122706, 42544239, 77735465 |
| fetuin B | 109042265 |
| GSTa1 | 109071513, 442977 |
| GSTp1 | 111185949, 494066, 75070646, 87564 |
| Hemopexin | 109107500, 11321561, 1335098 |
| HSP8 | 13938297, 16041102, 5729877 |
| orosomucoid 1 | 109110478 |
| Peroxiredoxin 1 | 109003875, 4505591, 55824562 |
| Peroxiredoxin 2 | 109123565, 32189392, 438069, 90076926, 33188452, 60654143 |
| Plasminogen | 112807252, 2737906, 38051823, 4505881 |
| S100A6 | 1173337, 20664042, 6755392, 7657532 |
| serpinA3 | 109084779 |
| serpinC1 | 114565551, 149708147, 179161, 4502261, 52695711, 576554, 179152 |
| serpinF1 | 189778, 15559258 |
| serpin G1 | 179617 |
| SOD1 | 74136167 |
| SP-D | 18490171, 93352568 |
| Thioredoxin | 1065111, 109002483 |
| Transthyretin | 109121862, 119621670, 219978, 230651, 23574795, 443297, 443297, 57089193, 999643 |
| vitD BP | 109074554, 139641, 18655424, 455970 |

C

| Protein | NCBI GI Protein Accession Number |
|---|---|
| Adiponectin | 4757760, 74136307 |
| ADP-ribosylation factor GTPase activating protein 1 | 8922652 |
| aldo-keto reductase family 1, member B1 | 442618, 90075192 |
| aldo-keto reductase family 1, member B10 | 3493209 |
| aldolase A | 75061505, 16740581, 28614 |
| annexin A2 | 109081460, 18645167, 34364597, 4757756 |
| annexin A5 | 3212603, 4502107, 75075702, 809185 |
| CD44 | 109106764, 29799, 30268334, 3832518, 422780 |
| Chloride intracellular channel protein 1 | 895845 |
| FLJ131659 | 23308541 |
| gamma globin | 15988413, 31725 |
| galectin 3 binding protein | 5031863 |
| HSP70 | 213804 |
| HSPA1L | 2119712, 87626 |
| lymphocyte cytosolic protein 1 | 4504965 |
| profilin 1 | 114665902, 149724221, 157833469, 999511 |
| quiescin 6 | 13325075 |
| SP-A | 109089169, 109089171, 60390965, 71969 |
| transaldolase 1 | 1082840, 109104910 |

Biomarkers of disease and treatment in the various proximal fluids and tissues are summarized in Table VIII. For asthma biomarker categories, large checkmarks indicate a biomarker classified in the "High" expression category (>6-fold increased), small checkmarks indicate a biomarker categorized in the "Intermediate" expression category (1.5- to 6-fold increased), and dashes indicate biomarkers not upregulated in asthmatic mice. In treatment biomarker categories, a checkmark indicates the biomarker was significantly reduced upon corticosteroid treatment; a dash indicates a biomarker not reduced upon treatment. Taken together, the studies presented herein significantly advance the field of asthma disease and treatment biomarkers by providing a comprehensive study of various proximal fluids and tissues in murine and cynomolgus models of chronic asthma.

TABLE VIII

| Potential Biomarker | Up in Chronic Asthma (Lung Tissue) | Up in Chronic Asthma (BAL fluid or cell mRNA) | Up In Developing Asthma (Lung tissue) | Down with Steroids (Lung Tissue) | Down with Steroids (BAL fluid or cell mRNA) |
|---|---|---|---|---|---|
| Chi3l4 (YM2) | ✓ | ✓ | ✓ | — | ✓ |
| ECP (Ear11) | ✓ | ✓ | ✓ | — | — |
| RETNLβ | ✓ | ✓ | ✓ | — | ✓ |
| CLCA3 | ✓ | ✓ | ✓ | — | ✓ |
| Prg2 (EMBP) | ✓ | ✓ | ✓ | ✓ | ✓ |
| EPX | ✓ | ✓ | — | ✓ | ✓ |
| MMP12 | ✓ | ✓ | ✓ | ✓ | — |
| AMCase (Chia) | ✓ | ✓ | — | ✓ | — |
| Chi3l3 (YM1) | ✓ | ✓ | ✓ | ✓ | ✓ |
| FCGBP | ✓ | ✓ | ✓ | — | ✓ |
| Reg3γ | ✓ | ✓ | ✓ | — | — |
| LTF | ✓ | ✓ | ✓ | ✓ | — |
| PGLYRP1 | ✓ | ✓ | — | — | ✓ |
| pIgR | ✓ | ✓ | ✓ | ✓ | ✓ |
| KLK1 | ✓ | ✓ | — | ✓ | ✓ |
| LCN2 | ✓ | ✓ | — | — | ✓ |
| GP-39 (Chi3l1) | ✓ | ✓ | — | ✓ | ✓ |
| ICAM-1 | — | ✓ | — | — | ✓ |

EXAMPLE 3

Expression of Biomakers in Response to Treatment with a TSLP Antagonist in Mice Having VItamin D Induced Skin Inflammation Materials and Methods Mice: Six- to eight-week-old Balb/c were obtained from Jackson Labs (Bar Harbour, Me.). TSLPR KO mice were obtained from Dr. W. Leonard, NIH, Bethesda, Md. (Al Shami et al., *J. Exp. Med.* 200:159-168 (2004). Age-matched males were used for the time-course study and females for two efficacy studies.

Vitamin D Induced Skin Inflammation: The vitamin D analogue, calcipotriol (Tocris, Ellisville, Mo.), was dissolved in ethanol and was applied daily to both sides of the ears at a final concentration of 2 nmol/ear. Control animals were given ethanol only. Ear swelling was measured daily using an engineer's pressure gauge (Peacock, Japan) and blood was collected. The blood was spun at 10.000 rpm for 5 minutes to separate the serum, which was frozen at −80 C. until analyzed by ELISA. Calcipotriol applications were stopped on day 8 (Balb/c mice), ears were harvested and fixed in 10% formalin for pathological evaluation or frozen directly in liquid nitrogen for mRNA extraction.

Neutralization Experiments: mice were treated with 0.1, 0.4, 1, 4, 12, 40 and 120 mgs per kg (mpk) of a rat anti-mouse TSLP antibody (designated "22E5") subcutaneously (s.c.) one day (d−1) prior to VitD3 treatment. Control mice received isotype antibody at 4 and 40 mpk. The mice were sacrificed at day 8.

It has been previously shown that TSLP is induced in keratinocytes after application of calcipotriol, a Vit D3 analogue, to the skin resulting in a disease corresponding to atopic dermatitis. Lie M. et al., *Proc. Natl. Acad. Sci.* 103:11736 (2006); Lie M. et al., *J. Invest. Dermatol.* 129: 498 (2009).

Real-time PCR was conducted on mRNA extracted from skin tissue of mice treated with calcipotriol in the absence or the presence of an antagonistic anti-TSLP antibody or an isotype control As shown in FIG. 5, multiple genes, such as EAR11, MMP12, LCN2, YM1, YM2, YKL-40, Reg3 g, PGLYRP1, CD44 were upregulated 2 fold or greater in calcipotriol treated mice, and then downregulated back to control levels with anti-TSLP treatment. No downregulation was observed with isotype control antibody. Similarly, real-time PCR was conducted on mRNA extracted from skin tissue of TSLPR KO mice treated with either ethanol (vehicle control) or calcipotriol. The data shows that EAR11, MMP12, and YM2 were not upregulated by the calcipotriol treatment, indicating that such genes are TSLP dependent.

EXAMPLE 4

Expression of Biomarkers in an Ova-Model of Lung Inflammation in TSLP KO and TSLPR KO Mice The standard model of OVA-induced asthma described in Example 1 was used for this experiment, using TSLP KO and TSLPR KO mice. Two to three month old female wild type, TSLP KO and TSLPR KO mice on C57BL/6 background were used in groups of six. TSLPR KO (C57BL6) mice were obtained from W. Leonard, NIH, Bethesda. TSLP KO (C57BL6) mice were generated in-house.

Real-time PCR was conducted on mRNA extracted from lung tissue and BAL cells of mice treated with OVA to induce lung inflammation +/−treatment with anti-TSLP. The results are shown in FIG. 6. EAR11 and MMP12 were greatly up-regulated upon OVA challenge, and this up-regulation was significantly reduced in TSLP KO and TSLPR KO in both BAL cells and lung tissue, indicating some TSLP dependence. Chi3l1 was also up-regulated upon OVA challenge, and this up-regulation was significantly reduced in TSLP KO and TSLPR KO in BAL cells only, indicating some TSLP dependence in BAL cells. Conversely, YNL was also up-regulated upon OVA challenge, and this up-regulation was significantly reduced in TSLP KO and TSLPR KO in lung tissue only, indicating some TSLP dependence in lung tissue. YNL showed no detectable expression in BAL cells.

EXAMPLE 5

TSLP Antibody Dose Range Study on Ova-Induced Asthma Model

Anti-mTSLP mAb 22E5 SCH 2487174 has demonstrated efficacy in reducing allergic inflammation, tissue remodeling and disease-related biomarker expression in the murine OVA/Alum induced asthma model. This experiment was carried out to demonstrate an effect of anti-TSLP mAb SCH2487174 on disease parameters and disease related biomarkers in an asthma lung inflammation model.

Materials and Methods

Mice and In Vivo Protocols: BALB/c mice (for ovalbumin (OVA)-induced asthma experiments) were purchased from the Jackson Laboratory. TSLPR KO (BALB/c mice) mice were obtained from W. Leonard, NIH, Bethesda. All of the mice were about 8 week old females weighing around 20 grams. The standard model of OVA-induced asthma described below was used. For the TSLP treated animals, the indicated dose of anti-TSLP antibody (SCH2487174) was injected subcutaneously at the following doses: 40 mpk, 4 mpk, 1 mpk, 0.4 mpk, 0.2 mpk, 0.08 mpk, 0.04 mpk, and 0.01 mpk two days prior to sensitization. A rat IgG2a isotype antibody (5G5) was used as a control at a dose of 40 mpk. Colonies were maintained in a specific pathogen-free environment.

Standard model of OVA-induced asthma in mice: For the standard model of OVA-induced asthma, mice were sensitized i.p. with 50 ug of ovalbumin from chicken egg white (Sigma-Aldrich) complex to 2 mg of IMJECT® (reagents used in connection with enhancing immune responses) Alum (Pierce) in 0.15M saline (Sigma-Aldrich) on day 0 and day 13, and primed 2 times on Day 27 and 28 with saline or nebulized OVA (10 mg/mL) for 45 min per session. Mice were given a final challenge of saline or OVA (25 mg/mL) on day 29, and tissues were harvested 1 day following OVA challenge.

The treatment group were as follows:
Group A OVA/Alum i.p sensitization only
Group B OVA/Alum sensitization, priming & challenge
Group C OVA/Alum sensitization, priming & challenge+ SCH2487174 40 mpk
Group D OVA/Alum sensitization, priming & challenge+ SCH2487174 4 mpk
Group E OVA/Alum sensitization, priming & challenge+ SCH2487174 1 mpk
Group F OVA/Alum sensitization, priming & challenge+ SCH2487174 0.4 mpk
Group G OVA/Alum sensitization, priming & challenge+ SCH2487174 0.2 mpk
Group H OVA/Alum sensitization, priming & challenge+ SCH2487174 0.08 mpk
Group I OVA/Alum sensitization, priming & challenge+ SCH2487174 0.04 mpk
Group J OVA/Alum sensitization, priming & challenge+ SCH2487174 0.01 mpk
Group K OVA/Alum sensitization, priming & challenge+ 5G5 40 mpk
Group L OVA/Alum i.p sensitization only (TSLPR KO)
Group M OVA/Alum sensitization, priming & challenge (TSLPR KO)

Harvest of murine BAL fluid, BAL cells, and lung tissue: BAL fluid was isolated by washing the lung (through the trachea) with 1 mL of PBS. Lavage fluid was kept on ice and centrifuged at 400 g for 5 min. The supernatant was frozen for cytokine analysis, and the cell pellet was resuspended in 1 mL of PBS for total viable cell count by Vi-CELL (Perkin-Elmer) and cell differentials by cytospin. Slides were air-dried, fixed with 95% ethanol, and stained with Wright-Giemsa (Sigma-Aldrich). A minimum of 200 cells were counted under the microscope per slide for cell differentials. The postcaval lung lobe and BAL cells were collected and snap-frozen in liquid nitrogen for qRT-PCR analysis as described previously for tissue (Chan et al., *J. Exp. Med.* 203:2577-87 (2006)) and below for BAL cells. The single left lung lobe was excised for histology and clinical scoring as described below.

mRNA isolation from BAL cells and qRT-PCR: Total RNA was isolated from BAL cells using the RNeasy method (Qiagen, Valencia, Calif.) and reverse-transcribed using WT-OVATION ® (chemicals, assays, and reagents for nucleic acid sequence amplification, sequencing and sequence analysis and detection) Pico System (NuGen Technologies, San Carlos Calif.). Primers were designed using Primer Express software (Applied Biosystem, Foster City, Calif.) or obtained commercially from Applied Biosystems (ABI). qRT-PCR was performed on 10 ng of cDNA from each sample as described previously. Chan et al., *J. Exp. Med.* 203:2577-87 (2006).

The relative mRNA abundance of selected proteins in mice having OVA-induced asthma and treated as described above is shown in FIG. 7. The mRNA expression was measured by real-time PCR in lung.

EXAMPLE 6

Expression of Biomarkers in Patients Subject to Atopy Patch Test

Atopic dermatitis patients were enrolled in a protocol in which lesional and non-lesional skin biopsies were obtained, and atopic patch tests (APT) with biopsy read-outs at 24 and 48 hours were performed. Each biopsy was divided in two parts: one embedded and used for immunohistochemistry and the other was frozen and used for gene expression analyses. Because atopic dermatitis patients have IgE bearing Langerhans cells in the epidermis, application of allergen on non-lesional skin (APT) will typically elicit a macroscopically visible eczematous reaction within 48-72 hours at the site of allergen application. This reaction is microscopically characterized by an influx of inflammatory cells, mainly T cells of the Th2 type. The eczematous reaction vanishes automatically after 72-96 hours.

Figure 8A:
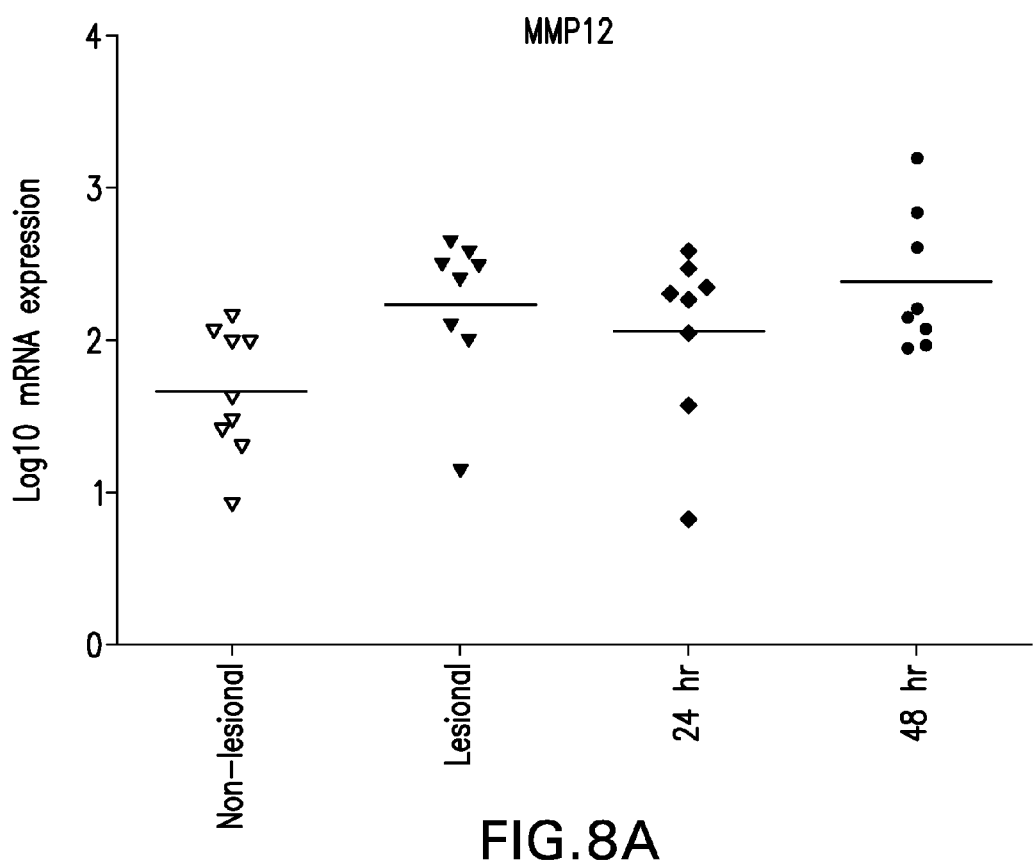
FIG. 8: Expression of selected biomarkers MMP12(A), YKL-40(B), LCN2(C) in patients subject to atopy patch test.
Figure 8B:
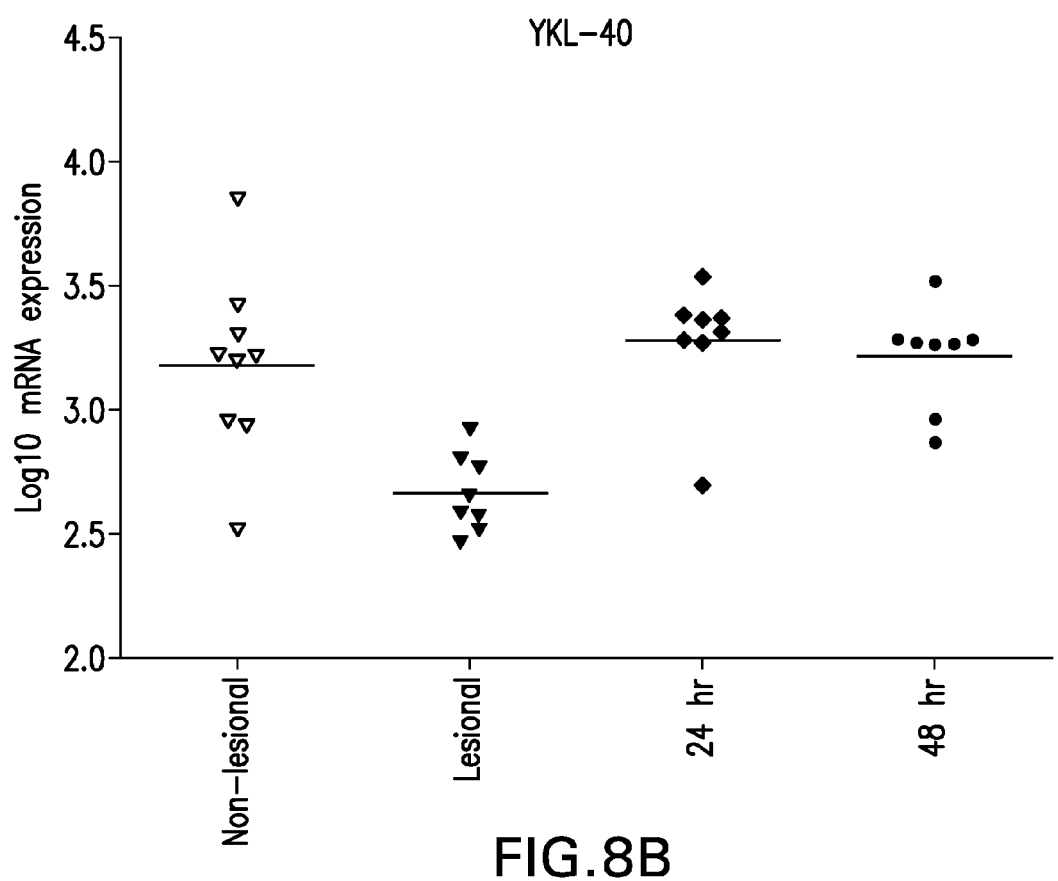
Figure 8C:
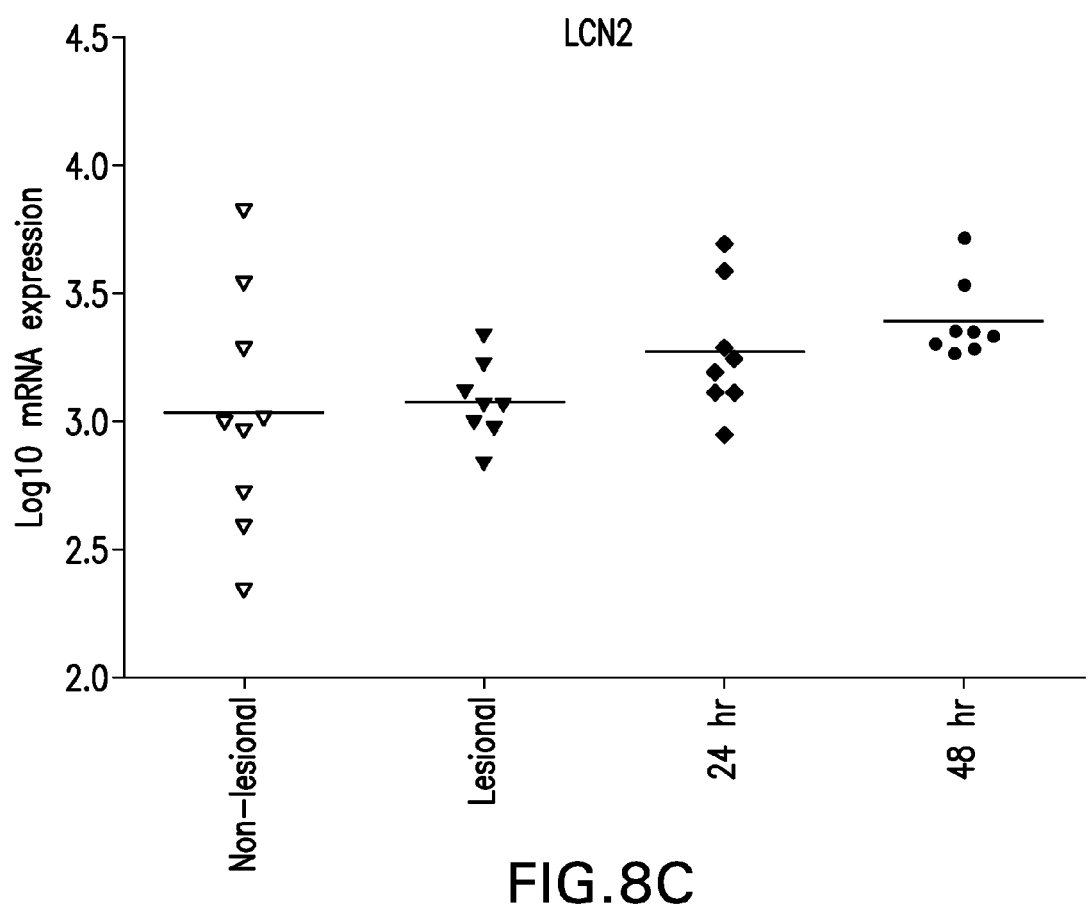

FIG. 8 shows the expression data from 8 patients enrolled in the study as determined by qPCT.

EXAMPLE 7

Expression of Biomarkers in Human Patients with Inflammatory Disease

The biomarkers of the invention are expressed in inflammatory skin samples from human patients. The biomarker levels were quantitated using real time PCR. Real-time quantitative PCR values were normalized to ubiquitin. Kruskal-Wallis statistical analysis was performed on log transformed data (median method). Total RNA was prepared from tissue by standard methodologies and reverse transcribed. Real-time quantitative PCR was performed by standard methodologies.

The human inflammatory skin disease panel included normal skin, non-lesional and lesional skin from psoriatic and atopic dermatitis patients. The panel included 35 normal skin samples (15 from autopsy donors and 20 from normal donors in clinical trial setting see below), 24 non-lesional psoriasis skin samples, 25 lesional psoriasis skin samples, 30 non-lesional atopic dermatitis skin samples, and 30 lesional atopic dermatitis skin samples. Two 4 mm punch biopsies were taken from each patient. Samples were obtained in a clinical trial setting at Stanford University Dermatology Department. Autopsy donor materials were obtained from Zoion.

All non-lesional and lesional patient samples were ranked by severity using either the PASI (psoriasis area and severity index) score or EASI (eczema area and severity index) score. For psoriasis patients, the PASI scores were in the range of 9-20.75. For atopic dermatitis patients, the EASI scores were in the range of 1.85-35.95. These scores reflected the extent and severity of disease over the patient's body. Real time quantitative PCR values were normalized to ubiqutin. Kruskal-Wallis statistical analysis was performed on log transformed data (median method).

The expression level (log transformed) corresponds to the amount of biomarker expressed in the tissue sample, such that the higher the expression level (log transformed), the greater the amount of the biomarker expressed in the tissue sample.

Figure 9B:
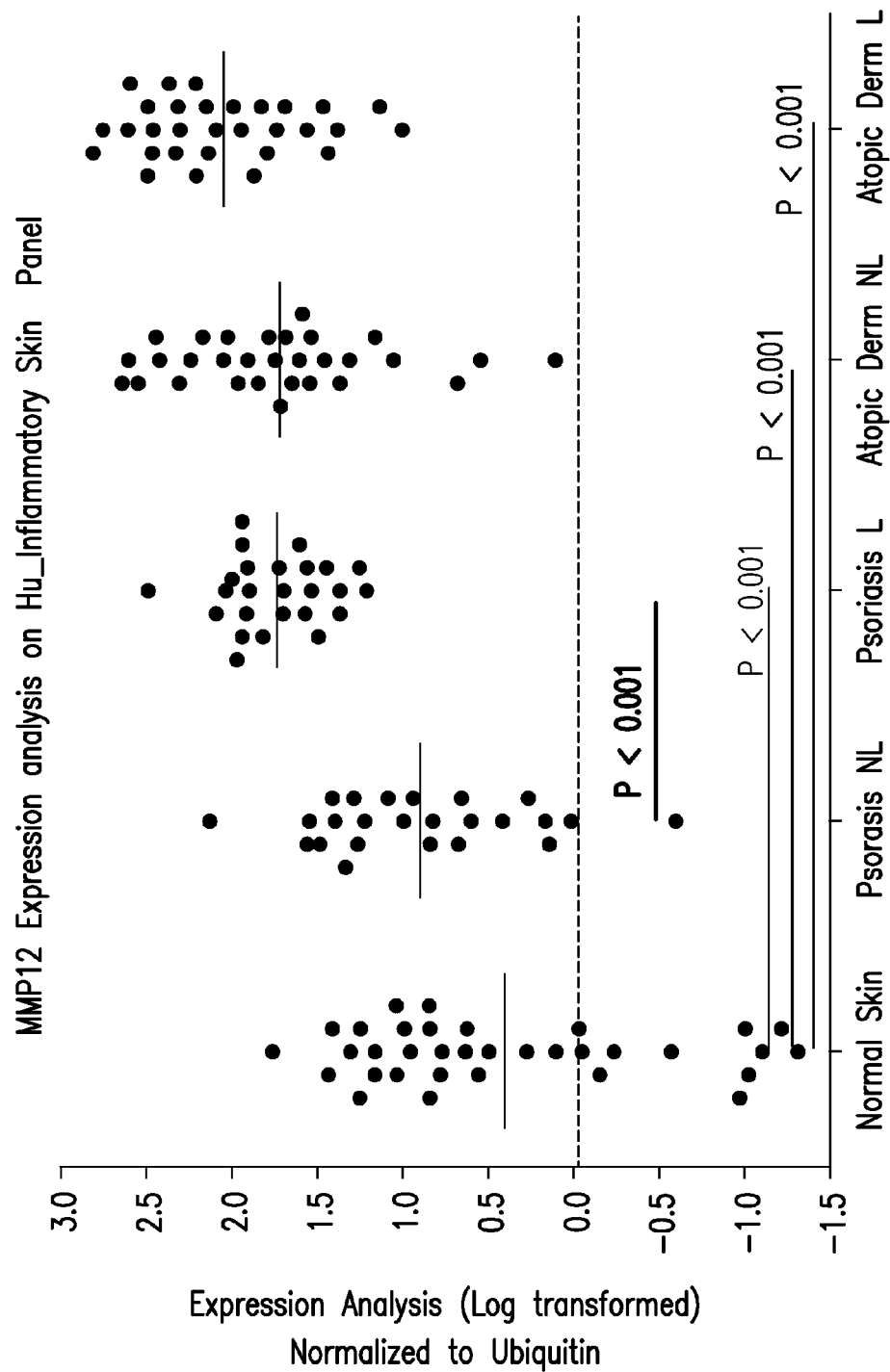
FIG. 9: Expression of selected biomarkers LCN2(A) and MMP12(B) in samples from human patients with inflammatory disease.

FIG. 9 shows the results of this experiment.

What is claimed is:

1. A method of treating a mammalian subject with asthma or atopic dermatitis with an anti-thymic stromal lymphopoietin (TSLP) antibody comprising: measuring expression of biomarkers in a sample from said subject, wherein the biomarkers comprise Lipocalin 2(LCN2), Peptidoglycan Recognition Protein 1(PGLYRP1) and RNASE3; Regenerating Islet-derived 3 gamma (REG3G), CD44, and RNASE7; RNASE2, Acidic Mammalian Chitinase(AMCASE), and Chitinase Acidic Pseudogene 2(CHIAP2); or PGLYRP1, REG3G, and AMCASE, and, if the biomarker levels in the sample are higher than a control, administering a therapeutically effective amount of an anti-TSLP antibody to the subject.

2. A method for treating a subject with asthma or atopic dermatitis with an anti-TSLP antibody comprising:
   a) obtaining a first biological sample from the subject prior to administering a dose of an anti-TSLP antibody;
   b) measuring the expression of biomarkers in the first biological sample, wherein the biomarkers comprise LCN2, PGLYRP1 and RNASE3; REG3G, CD44, and RNASE7; RNASE2, AMCASE, and CHIAP2; or PGLYRP1, REG3G, and AMCASE,
   c) administering the anti-TSLP antibody to the subject;
   d) obtaining from the subject a second biological sample;
   e) measuring the expression of the biomarkers in the second sample;
   f) comparing the expression of the biomarkers in the second biological sample with the expression of the biomarkers in the first biological sample, and, if the biomarker levels are reduced in the second biological sample as compared to the first biological sample, administering a therapeutically effective amount of an anti-TSLP antibody to the subject.

3. A method for selecting a subject with asthma or atopic dermatitis for treatment with an anti-TSLP antibody comprising measuring expression of biomarkers in a sample from said subject, wherein the biomarkers comprise LCN2, PGLYRP1 and RNASE3; REG3G, CD44, and RNASE7; RNASE2, AMCASE, and CHIAP2; or PGLYRP1, REG3G, and AMCASE, and, if the biomarker levels in the sample are higher than the levels of a control, then administering a therapeutically effective amount of an anti-TSLP antibody to the subject.

4. A method for monitoring progress of treatment of a subject with asthma or atopic dermatitis with an anti-TSLP antibody comprising: a) measuring expression of biomarkers in a sample from said subject, wherein the biomarkers comprise LCN2, PGLYRP1 and RNASE3; REG3G, CD44, and RNASE7; RNASE2, AMCASE, and CHIAP2; or PGLYRP1, REG3G, and AMCASE, and, if the biomarker levels in the sample are higher than the levels of a control, then administering a therapeutically effective amount of an anti-TSLP antibody to the subject.

5. The method of any one of claims 1-4, wherein the sample is a tissue sample, a skin biopsy, a blood sample, serum, or sputum.

6. The method of any one of claims 1-4, wherein expression of the biomarkers are determined by gene expression analysis or immunoassay.

7. The method of any one of claims 1 and 3-4, wherein the control is a sample from the subject prior to treatment with an anti-TSLP antibody.

8. The method of any one of claims 1 and 3-4, wherein the control is one or more samples from subjects that do not suffer from asthma or atopic dermatitis.

9. The method of any one of claims 1 and 3-4, wherein the control is one or more samples from subjects that do not suffer from asthma or atopic dermatitis and have not been treated with an anti-TSLP antibody.

\* \* \* \* \*